United States Patent [19]
Baker et al.

[11] Patent Number: 5,494,818
[45] Date of Patent: Feb. 27, 1996

[54] UBIQUITIN-SPECIFIC PROTEASES

[75] Inventors: Rohan T. Baker, Garran, Australia; John W. Tobias, Cambridge; Alexander Varshavsky, Boston, both of Mass.

[73] Assignee: Massachusetts Institute of Technology, Cambridge, Mass.

[21] Appl. No.: 5,002

[22] Filed: Jan. 15, 1993

Related U.S. Application Data

[60] Division of Ser. No. 789,915, Nov. 8, 1991, Pat. No. 5,212,058, which is a continuation-in-part of Ser. No. 573,958, Aug. 28, 1990, abandoned, which is a continuation-in-part of Ser. No. 521,089, May 9, 1990, abandoned.

[51] Int. Cl.$^6$ .............................. C12N 9/50; C12N 9/58; C12N 9/64
[52] U.S. Cl. .......................... 435/219; 435/223; 435/226
[58] Field of Search ..................................... 435/219, 224

[56] References Cited

U.S. PATENT DOCUMENTS

| | | | |
|---|---|---|---|
| 5,132,213 | 7/1992 | Bachmair et al. | 435/69.7 |
| 5,156,968 | 10/1992 | Liu | 435/224 |
| 5,212,058 | 5/1993 | Baker et al. | 435/252.33 |
| 5,391,490 | 2/1995 | Varshausky et al. | 435/224 |

FOREIGN PATENT DOCUMENTS

| | | |
|---|---|---|
| WO88/02406 | 4/1988 | WIPO. |
| WO89/12678 | 6/1989 | WIPO. |
| 91/17245 | 11/1991 | WIPO. |

OTHER PUBLICATIONS

Rohan T. Baker et al., "Ubiquitin–Specific Processing Proteases of the Yeast Saccharomyces Cerevisiae", CH200, Abstracts, 20th Annual Meetings *Journal of Cellular Biochemistry*, Keystone Symposia on Molecular & Cellular Biology, Supplement 15G, 1991, Apr. 6–Apr. 25, 1991, Wiley–Liss.

K. Nagai and H. C. Thogersen, "Generation of β–globin by sequence–specific Proteolysis of a hybrid protein produced in *Escherichia coli*," *Nature* 309:810–812 (1984).

Hershko et al., "Role of the α–amino group of protein in ubiquitin–mediated protein breakdown," *Pro. Natl. Acad. Sci. USA* 81:7021–7025 (1985).

Tsunasawa et al., "Amino–terminal Processing of Mutant Forms of Yeast Iso–1–cytochrome c," *J. Biol. Chem.* 260:5382–5391 (1985).

Boissel et al., "Amino–terminal processing of proteins: Hemoglobin South Florida, a variant with retention of initiator methionine and $N^\alpha$–acetylation," *Proc. Natl. Acad. Sci. USA* 82:8448–8452 (1985).

Thornton et al., "Amino and Carboxy–terminal regions in globular proteins," *J. Mol. Biol.* 167:443–460 (1983).

Ferber et al., "Transfer RNA is Required for Conjugation of Ubiquitin to Selective Substrates of the Ubiquitin– and ATP–dependent Proteolytic System," *J. Biol. Chem.* 261:3128–3134 (1986).

Bachmair et al., "In Vivo Half–Life of a Protein is a Function of its Amino–Terminal Residue," *Science* 234:179–186 (1986).

Ferber et al., "Role of arginine–tRNA in protein degradation by the ubiquitin pathway," *Nature* 326:808–811 (1988).

Reiss et al., "Specificity of Binding of $NH_2$–terminal Residue of Proteins to Ubiquitin–Protein Ligase," *J. Biol. Chem.* 263:2693–2698 (1988).

(List continued on next page.)

*Primary Examiner*—Robert A. Wax
*Assistant Examiner*—Eric Grimes
*Attorney, Agent, or Firm*—Kevin M. Farrell

[57] ABSTRACT

The disclosure relates to a generic class of ubiquitin-specific proteases which specifically cleave at the C-terminus of the ubiquitin moiety in a ubiquitin fusion protein irrespective of the size of the ubiquitin fusion protein. More specifically, the disclosure relates to ubiquitin-specific proteases of this class which have been isolated from a cell. The disclosure also relates to isolated DNA sequences encoding the proteases of this class.

5 Claims, 4 Drawing Sheets

OTHER PUBLICATIONS

Townsend et al., "Defective Presentation to Class I–Restricted Cytotoxic T Lymphocytes in Vaccinia–Infected Cells is Overcome by Enhanced Degradation of Antigen," *J. Exp. Med.* 168:1211–1224 (1988).

A. Bachmair and A. Varshavsky, "The Degradation Signal in a Short–Lived Protein," *Cell* 56:1019–1032 (1989).

Chau et al., "A Multiubiquitin Chain is Confined to Specific Lysine in a Targeted Short–Lived Protein," *Science* 243:1576–1583 (1989).

Gonda et al., "Universality and Structure of the N–end Rule," *J. Biol. Chem.* 264:16700–16712 (1989).

Miller et al., "Cloning and Expression of a Yeast Ubiquitin–Protein Cleaving Activity in *Escherichia Coli*," *Biotechnology* 7:698–704 (1989).

Helmut M. Sassenfeld, "Engineering Proteins for Purification," *Trends in Biotechnology* 8:88–93 (1990).

Wilkinson et al., "The Neuron–Specific Protein PGP 9.5 is a Ubiquitin Carboxyl–Terminal Hydrolase," *Science* 246:670–675 (1989).

Ohmen et al., "Divergent Overlapping Transcripts at the PET122 Locus in *Saccharomyces cerevisiae*," *Mol. Cell. Biol.* 10:3027–3035, (1990).

Ohmen et al., "Molecular Cloning and Nucleotide Sequence of the Nuclear PET122 Gene Required for Expression of the Mitochondrial COX3 Gene in *S. cerevisiae*," *Nucleic Acids Research* 16:10783–10803 (1988).

Tobias et al., J. Biol. Chem. 266:12021–12028 (1991).

Agell et al., Biochem J. 273:615–620 (1991).

Baker et al., J. Biol. Chem. 267:23364–23375 (1992).

Sullivan et al., Plant Physiol. 94:710–716 (1990).

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3365 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..3363

( x i ) SEQUENCE DESCRIPTION: SEQ ID NO:1:

```
ATG  CAG  ATT  TTC  GTC  AAG  ACT  TTG  ACC  GGT  AAA  ACC  ATA  ACA  TTG  GAA        48
Met  Gln  Ile  Phe  Val  Lys  Thr  Leu  Thr  Gly  Lys  Thr  Ile  Thr  Leu  Glu
 1              5                        10                       15

GTT  GAA  TCT  TCC  GAT  ACC  ATC  GAC  AAC  GTT  AAG  TCG  AAA  ATT  CAA  GAC        96
Val  Glu  Ser  Ser  Asp  Thr  Ile  Asp  Asn  Val  Lys  Ser  Lys  Ile  Gln  Asp
              20                       25                       30

AAG  GAA  GGT  ATC  CCT  CCA  GAT  CAA  CAA  AGA  TTG  ATC  TTT  GCC  GGT  AAG       144
Lys  Glu  Gly  Ile  Pro  Pro  Asp  Gln  Gln  Arg  Leu  Ile  Phe  Ala  Gly  Lys
         35                       40                       45

CAG  CTA  GAA  GAC  GGT  AGA  ACG  CTG  TCT  GAT  TAC  AAC  ATT  CAG  AAG  GAG       192
Gln  Leu  Glu  Asp  Gly  Arg  Thr  Leu  Ser  Asp  Tyr  Asn  Ile  Gln  Lys  Glu
     50                       55                       60

TCC  ACC  TTA  CAT  CTT  GTG  CTA  AGG  CTA  AGA  GGT  GGT  ATG  CAC  GGA  TCC       240
Ser  Thr  Leu  His  Leu  Val  Leu  Arg  Leu  Arg  Gly  Gly  Met  His  Gly  Ser
 65                       70                       75                       80

GGA  GCT  TGG  CTG  TTG  CCC  GTC  TCA  CTG  GTG  AAA  AGA  AAA  ACC  ACC  CTG       288
Gly  Ala  Trp  Leu  Leu  Pro  Val  Ser  Leu  Val  Lys  Arg  Lys  Thr  Thr  Leu
                         85                       90                       95

GCG  CCC  AAT  ACG  CAA  ACC  GCC  TCT  CCC  CGC  GCG  TTG  GCC  GAT  TCA  TTA       336
Ala  Pro  Asn  Thr  Gln  Thr  Ala  Ser  Pro  Arg  Ala  Leu  Ala  Asp  Ser  Leu
                    100                      105                      110

ATG  CAG  CTG  GCA  CGA  CAG  GTT  TCC  CGA  CTT  AAT  CGC  CTT  GCA  GCA  CAT       384
Met  Gln  Leu  Ala  Arg  Gln  Val  Ser  Arg  Leu  Asn  Arg  Leu  Ala  Ala  His
               115                      120                      125

CCC  CCT  TTC  GCC  AGC  TGG  CGT  AAT  AGC  GAA  GAG  GCC  CGC  ACC  GAT  CGC       432
Pro  Pro  Phe  Ala  Ser  Trp  Arg  Asn  Ser  Glu  Glu  Ala  Arg  Thr  Asp  Arg
          130                      135                      140

CCT  TCC  CAA  CAG  TTG  CGC  AGC  CTG  AAT  GGC  GAA  TGG  CGC  TTT  GCC  TGG       480
Pro  Ser  Gln  Gln  Leu  Arg  Ser  Leu  Asn  Gly  Glu  Trp  Arg  Phe  Ala  Trp
145                      150                      155                      160

TTT  CCG  GCA  CCA  GAA  GCG  GTG  CCG  GAA  AGC  TGG  CTG  GAG  TGC  GAT  CTT       528
Phe  Pro  Ala  Pro  Glu  Ala  Val  Pro  Glu  Ser  Trp  Leu  Glu  Cys  Asp  Leu
                    165                      170                      175
```

| | | | | | | | | | | | | | | | | |
|---|---|---|---|---|---|---|---|---|---|---|---|---|---|---|---|---|
| CCT | GAG | GCC | GAT | ACT | GTC | GTC | GTC | CCC | TCA | AAC | TGG | CAG | ATG | CAC | GGT | 576 |
| Pro | Glu | Ala | Asp<br>180 | Thr | Val | Val | Val | Pro<br>185 | Ser | Asn | Trp | Gln | Met<br>190 | His | Gly | |
| TAC | GAT | GCG | CCC | ATC | TAC | ACC | AAC | GTA | ACC | TAT | CCC | ATT | ACG | GTC | AAT | 624 |
| Tyr | Asp | Ala<br>195 | Pro | Ile | Tyr | Thr | Asn<br>200 | Val | Thr | Tyr | Pro | Ile<br>205 | Thr | Val | Asn | |
| CCG | CCG | TTT | GTT | CCC | ACG | GAG | AAT | CCG | ACG | GGT | TGT | TAC | TCG | CTC | ACA | 672 |
| Pro | Pro<br>210 | Phe | Val | Pro | Thr | Glu | Asn<br>215 | Pro | Thr | Gly | Cys | Tyr<br>220 | Ser | Leu | Thr | |
| TTT | AAT | GTT | GAT | GAA | AGC | TGG | CTA | CAG | GAA | GGC | CAG | ACG | CGA | ATT | ATT | 720 |
| Phe<br>225 | Asn | Val | Asp | Glu | Ser<br>230 | Trp | Leu | Gln | Glu | Gly<br>235 | Gln | Thr | Arg | Ile | Ile<br>240 | |
| TTT | GAT | GGC | GTT | AAC | TCG | GCG | TTT | CAT | CTG | TGG | TGC | AAC | GGG | CGC | TGG | 768 |
| Phe | Asp | Gly | Val | Asn<br>245 | Ser | Ala | Phe | His | Leu<br>250 | Trp | Cys | Asn | Gly | Arg<br>255 | Trp | |
| GTC | GGT | TAC | GGC | CAG | GAC | AGT | CGT | TTG | CCG | TCT | GAA | TTT | GAC | CTG | AGC | 816 |
| Val | Gly | Tyr | Gly<br>260 | Gln | Asp | Ser | Arg | Leu<br>265 | Pro | Ser | Glu | Phe | Asp<br>270 | Leu | Ser | |
| GCA | TTT | TTA | CGC | GCC | GGA | GAA | AAC | CGC | CTC | GCG | GTG | ATG | GTG | CTG | CGT | 864 |
| Ala | Phe | Leu<br>275 | Arg | Ala | Gly | Glu | Asn<br>280 | Arg | Leu | Ala | Val | Met<br>285 | Val | Leu | Arg | |
| TGG | AGT | GAC | GGC | AGT | TAT | CTG | GAA | GAT | CAG | GAT | ATG | TGG | CGG | ATG | AGC | 912 |
| Trp | Ser | Asp<br>290 | Gly | Ser | Tyr | Leu | Glu<br>295 | Asp | Gln | Asp | Met | Trp<br>300 | Arg | Met | Ser | |
| GGC | ATT | TTC | CGT | GAC | GTC | TCG | TTG | CTG | CAT | AAA | CCG | ACT | ACA | CAA | ATC | 960 |
| Gly<br>305 | Ile | Phe | Arg | Asp | Val<br>310 | Ser | Leu | Leu | His | Lys<br>315 | Pro | Thr | Thr | Gln | Ile<br>320 | |
| AGC | GAT | TTC | CAT | GTT | GCC | ACT | CGC | TTT | AAT | GAT | GAT | TTC | AGC | CGC | GCT | 1008 |
| Ser | Asp | Phe | His | Val<br>325 | Ala | Thr | Arg | Phe | Asn<br>330 | Asp | Asp | Phe | Ser | Arg<br>335 | Ala | |
| GTA | CTG | GAG | GCT | GAA | GTT | CAG | ATG | TGC | GGC | GAG | TTG | CGT | GAC | TAC | CTA | 1056 |
| Val | Leu | Glu | Ala<br>340 | Glu | Val | Gln | Met | Cys<br>345 | Gly | Glu | Leu | Arg | Asp<br>350 | Tyr | Leu | |
| CGG | GTA | ACA | GTT | TCT | TTA | TGG | CAG | GGT | GAA | ACG | CAG | GTC | GCC | AGC | GGC | 1104 |
| Arg | Val | Thr<br>355 | Val | Ser | Leu | Trp | Gln<br>360 | Gly | Glu | Thr | Gln | Val<br>365 | Ala | Ser | Gly | |
| ACC | GCG | CCT | TTC | GGC | GGT | GAA | ATT | ATC | GAT | GAG | CGT | GGT | GGT | TAT | GCC | 1152 |
| Thr | Ala<br>370 | Pro | Phe | Gly | Gly | Glu<br>375 | Ile | Ile | Asp | Glu | Arg<br>380 | Gly | Gly | Tyr | Ala | |
| GAT | CGC | GTC | ACA | CTA | CGT | CTG | AAC | GTC | GAA | AAC | CCG | AAA | CTG | TGG | AGC | 1200 |
| Asp<br>385 | Arg | Val | Thr | Leu | Arg<br>390 | Leu | Asn | Val | Glu | Asn<br>395 | Pro | Lys | Leu | Trp | Ser<br>400 | |
| GCC | GAA | ATC | CCG | AAT | CTC | TAT | CGT | GCG | GTG | GTT | GAA | CTG | CAC | ACC | GCC | 1248 |
| Ala | Glu | Ile | Pro | Asn<br>405 | Leu | Tyr | Arg | Ala | Val<br>410 | Val | Glu | Leu | His | Thr<br>415 | Ala | |
| GAC | GGC | ACG | CTG | ATT | GAA | GCA | GAA | GCC | TGC | GAT | GTC | GGT | TTC | CGC | GAG | 1296 |
| Asp | Gly | Thr | Leu<br>420 | Ile | Glu | Ala | Glu | Ala<br>425 | Cys | Asp | Val | Gly | Phe<br>430 | Arg | Glu | |
| GTG | CGG | ATT | GAA | AAT | GGT | CTG | CTG | CTG | CTG | AAC | GGC | AAG | CCG | TTG | CTG | 1344 |
| Val | Arg | Ile<br>435 | Glu | Asn | Gly | Leu | Leu<br>440 | Leu | Leu | Asn | Gly | Lys<br>445 | Pro | Leu | Leu | |
| ATT | CGA | GGC | GTT | AAC | CGT | CAC | GAG | CAT | CAT | CCT | CTG | CAT | GGT | CAG | GTC | 1392 |
| Ile | Arg<br>450 | Gly | Val | Asn | Arg | His<br>455 | Glu | His | His | Pro | Leu<br>460 | His | Gly | Gln | Val | |
| ATG | GAT | GAG | CAG | ACG | ATG | GTG | CAG | GAT | ATC | CTG | CTG | ATG | AAG | CAG | AAC | 1440 |
| Met<br>465 | Asp | Glu | Gln | Thr | Met<br>470 | Val | Gln | Asp | Ile | Leu<br>475 | Leu | Met | Lys | Gln | Asn<br>480 | |
| AAC | TTT | AAC | GCC | GTG | CGC | TGT | TCG | CAT | TAT | CCG | AAC | CAT | CCG | CTG | TGG | 1488 |
| Asn | Phe | Asn | Ala | Val<br>485 | Arg | Cys | Ser | His | Tyr<br>490 | Pro | Asn | His | Pro | Leu<br>495 | Trp | |

| | | | | | | | | | | | | | | | | |
|---|---|---|---|---|---|---|---|---|---|---|---|---|---|---|---|---|
| TAC | ACG | CTG | TGC | GAC | CGC | TAC | GGC | CTG | TAT | GTG | GTG | GAT | GAA | GCC | AAT | 1536 |
| Tyr | Thr | Leu | Cys | Asp | Arg | Tyr | Gly | Leu | Tyr | Val | Val | Asp | Glu | Ala | Asn | |
| | | | 500 | | | | | 505 | | | | | 510 | | | |
| ATT | GAA | ACC | CAC | GGC | ATG | GTG | CCA | ATG | AAT | CGT | CTG | ACC | GAT | GAT | CCG | 1584 |
| Ile | Glu | Thr | His | Gly | Met | Val | Pro | Met | Asn | Arg | Leu | Thr | Asp | Asp | Pro | |
| | | | 515 | | | | 520 | | | | | 525 | | | | |
| CGC | TGG | CTA | CCG | GCG | ATG | AGC | GAA | CGC | GTA | ACG | CGA | ATG | GTG | CAG | CGC | 1632 |
| Arg | Trp | Leu | Pro | Ala | Met | Ser | Glu | Arg | Val | Thr | Arg | Met | Val | Gln | Arg | |
| | 530 | | | | | 535 | | | | | 540 | | | | | |
| GAT | CGT | AAT | CAC | CCG | AGT | GTG | ATC | ATC | TGG | TCG | CTG | GGG | AAT | GAA | TCA | 1680 |
| Asp | Arg | Asn | His | Pro | Ser | Val | Ile | Ile | Trp | Ser | Leu | Gly | Asn | Glu | Ser | |
| 545 | | | | | 550 | | | | | 555 | | | | | 560 | |
| GGC | CAC | GGC | GCT | AAT | CAC | GAC | GCG | CTG | TAT | CGC | TGG | ATC | AAA | TCT | GTC | 1728 |
| Gly | His | Gly | Ala | Asn | His | Asp | Ala | Leu | Tyr | Arg | Trp | Ile | Lys | Ser | Val | |
| | | | | 565 | | | | | 570 | | | | | 575 | | |
| GAT | CCT | TCC | CGC | CCG | GTG | CAG | TAT | GAA | GGC | GGC | GGA | GCC | GAC | ACC | ACG | 1776 |
| Asp | Pro | Ser | Arg | Pro | Val | Gln | Tyr | Glu | Gly | Gly | Gly | Ala | Asp | Thr | Thr | |
| | | | 580 | | | | | 585 | | | | | 590 | | | |
| GCC | ACC | GAT | ATT | ATT | TGC | CCG | ATG | TAC | GCG | CGC | GTG | GAT | GAA | GAC | CAG | 1824 |
| Ala | Thr | Asp | Ile | Ile | Cys | Pro | Met | Tyr | Ala | Arg | Val | Asp | Glu | Asp | Gln | |
| | | 595 | | | | | 600 | | | | | 605 | | | | |
| CCC | TTC | CCG | GCT | GTG | CCG | AAA | TGG | TCC | ATC | AAA | AAA | TGG | CTT | TCG | CTA | 1872 |
| Pro | Phe | Pro | Ala | Val | Pro | Lys | Trp | Ser | Ile | Lys | Lys | Trp | Leu | Ser | Leu | |
| 610 | | | | | 615 | | | | | 620 | | | | | | |
| CCT | GGA | GAG | ACG | CGC | CCG | CTG | ATC | CTT | TGC | GAA | TAC | GCC | CAC | GCG | ATG | 1920 |
| Pro | Gly | Glu | Thr | Arg | Pro | Leu | Ile | Leu | Cys | Glu | Tyr | Ala | His | Ala | Met | |
| 625 | | | | | 630 | | | | | 635 | | | | | 640 | |
| GGT | AAC | AGT | CTT | GGC | GGT | TTC | GCT | AAA | TAC | TGG | CAG | GCG | TTT | CGT | CAG | 1968 |
| Gly | Asn | Ser | Leu | Gly | Gly | Phe | Ala | Lys | Tyr | Trp | Gln | Ala | Phe | Arg | Gln | |
| | | | | 645 | | | | | 650 | | | | | 655 | | |
| TAT | CCC | CGT | TTA | CAG | GGC | GGC | TTC | GTC | TGG | GAC | TGG | GTG | GAT | CAG | TCG | 2016 |
| Tyr | Pro | Arg | Leu | Gln | Gly | Gly | Phe | Val | Trp | Asp | Trp | Val | Asp | Gln | Ser | |
| | | | 660 | | | | | 665 | | | | | 670 | | | |
| CTG | ATT | AAA | TAT | GAT | GAA | AAC | GGC | AAC | CCG | TGG | TCG | GCT | TAC | GGC | GGT | 2064 |
| Leu | Ile | Lys | Tyr | Asp | Glu | Asn | Gly | Asn | Pro | Trp | Ser | Ala | Tyr | Gly | Gly | |
| | | 675 | | | | | 680 | | | | | 685 | | | | |
| GAT | TTT | GGC | GAT | ACG | CCG | AAC | GAT | CGC | CAG | TTC | TGT | ATG | AAC | GGT | CTG | 2112 |
| Asp | Phe | Gly | Asp | Thr | Pro | Asn | Asp | Arg | Gln | Phe | Cys | Met | Asn | Gly | Leu | |
| 690 | | | | | 695 | | | | | 700 | | | | | | |
| GTC | TTT | GCC | GAC | CGC | ACG | CCG | CAT | CCA | GCG | CTG | ACG | GAA | GCA | AAA | CAC | 2160 |
| Val | Phe | Ala | Asp | Arg | Thr | Pro | His | Pro | Ala | Leu | Thr | Glu | Ala | Lys | His | |
| 705 | | | | | 710 | | | | | 715 | | | | | 720 | |
| CAG | CAG | CAG | TTT | TTC | CAG | TTC | CGT | TTA | TCC | GGG | CAA | ACC | ATC | GAA | GTG | 2208 |
| Gln | Gln | Gln | Phe | Phe | Gln | Phe | Arg | Leu | Ser | Gly | Gln | Thr | Ile | Glu | Val | |
| | | | | 725 | | | | | 730 | | | | | 735 | | |
| ACC | AGC | GAA | TAC | CTG | TTC | CGT | CAT | AGC | GAT | AAC | GAG | CTC | CTG | CAC | TGG | 2256 |
| Thr | Ser | Glu | Tyr | Leu | Phe | Arg | His | Ser | Asp | Asn | Glu | Leu | Leu | His | Trp | |
| | | | 740 | | | | | 745 | | | | | 750 | | | |
| ATG | GTG | GCG | CTG | GAT | GGT | AAG | CCG | CTG | GCA | AGC | GGT | GAA | GTG | CCT | CTG | 2304 |
| Met | Val | Ala | Leu | Asp | Gly | Lys | Pro | Leu | Ala | Ser | Gly | Glu | Val | Pro | Leu | |
| | | | 755 | | | | 760 | | | | | 765 | | | | |
| GAT | GTC | GCT | CCA | CAA | GGT | AAA | CAG | TTG | ATT | GAA | CTG | CCT | GAA | CTA | CCG | 2352 |
| Asp | Val | Ala | Pro | Gln | Gly | Lys | Gln | Leu | Ile | Glu | Leu | Pro | Glu | Leu | Pro | |
| 770 | | | | | 775 | | | | | 780 | | | | | | |
| CAG | CCG | GAG | AGC | GCC | GGG | CAA | CTC | TGG | CTC | ACA | GTA | CGC | GTA | GTG | CAA | 2400 |
| Gln | Pro | Glu | Ser | Ala | Gly | Gln | Leu | Trp | Leu | Thr | Val | Arg | Val | Val | Gln | |
| 785 | | | | | 790 | | | | | 795 | | | | | 800 | |
| CCG | AAC | GCG | ACC | GCA | TGG | TCA | GAA | GCC | GGG | CAC | ATC | AGC | GCC | TGG | CAG | 2448 |
| Pro | Asn | Ala | Thr | Ala | Trp | Ser | Glu | Ala | Gly | His | Ile | Ser | Ala | Trp | Gln | |
| | | | | 805 | | | | | 810 | | | | | 815 | | |

-continued

| | | | | | | | | | | | | | | | | |
|---|---|---|---|---|---|---|---|---|---|---|---|---|---|---|---|---|
| CAG | TGG | CGT | CTG | GCG | GAA | AAC | CTC | AGT | GTG | ACG | CTC | CCC | GCC | GCG | TCC | 2496 |
| Gln | Trp | Arg | Leu<br>820 | Ala | Glu | Asn | Leu | Ser<br>825 | Val | Thr | Leu | Pro | Ala<br>830 | Ala | Ser | |
| CAC | GCC | ATC | CCG | CAT | CTG | ACC | ACC | AGC | GAA | ATG | GAT | TTT | TGC | ATC | GAG | 2544 |
| His | Ala | Ile<br>835 | Pro | His | Leu | Thr | Thr<br>840 | Ser | Glu | Met | Asp | Phe<br>845 | Cys | Ile | Glu | |
| CTG | GGT | AAT | AAG | CGT | TGG | CAA | TTT | AAC | CGC | CAG | TCA | GGC | TTT | CTT | TCA | 2592 |
| Leu | Gly | Asn<br>850 | Lys | Arg | Trp | Gln | Phe<br>855 | Asn | Arg | Gln | Ser | Gly<br>860 | Phe | Leu | Ser | |
| CAG | ATG | TGG | ATT | GGC | GAT | AAA | AAA | CAA | CTG | CTG | ACG | CCG | CTG | CGC | GAT | 2640 |
| Gln | Met | Trp<br>865 | Ile | Gly | Asp | Lys<br>870 | Lys | Gln | Leu | Leu<br>875 | Thr | Pro | Leu | Arg | Asp<br>880 | |
| CAG | TTC | ACC | CGT | GCA | CCG | CTG | GAT | AAC | GAC | ATT | GGC | GTA | AGT | GAA | GCG | 2688 |
| Gln | Phe | Thr | Arg | Ala<br>885 | Pro | Leu | Asp | Asn | Asp<br>890 | Ile | Gly | Val | Ser | Glu<br>895 | Ala | |
| ACC | CGC | ATT | GAC | CCT | AAC | GCC | TGG | GTC | GAA | CGC | TGG | AAG | GCG | GCG | GGC | 2736 |
| Thr | Arg | Ile | Asp<br>900 | Pro | Asn | Ala | Trp | Val<br>905 | Glu | Arg | Trp | Lys | Ala<br>910 | Ala | Gly | |
| CAT | TAC | CAG | GCC | GAA | GCA | GCG | TTG | TTG | CAG | TGC | ACG | GCA | GAT | ACA | CTT | 2784 |
| His | Tyr | Gln<br>915 | Ala | Glu | Ala | Ala | Leu<br>920 | Leu | Gln | Cys | Thr | Ala<br>925 | Asp | Thr | Leu | |
| GCT | GAT | GCG | GTG | CTG | ATT | ACG | ACC | GCT | CAC | GCG | TGG | CAG | CAT | CAG | GGG | 2832 |
| Ala | Asp<br>930 | Ala | Val | Leu | Ile | Thr<br>935 | Thr | Ala | His | Ala | Trp<br>940 | Gln | His | Gln | Gly | |
| AAA | ACC | TTA | TTT | ATC | AGC | CGG | AAA | ACC | TAC | CGG | ATT | GAT | GGT | AGT | GGT | 2880 |
| Lys<br>945 | Thr | Leu | Phe | Ile | Ser<br>950 | Arg | Lys | Thr | Tyr | Arg<br>955 | Ile | Asp | Gly | Ser | Gly<br>960 | |
| CAA | ATG | GCG | ATT | ACC | GTT | GAT | GTT | GAA | GTG | GCG | AGC | GAT | ACA | CCG | CAT | 2928 |
| Gln | Met | Ala | Ile | Thr<br>965 | Val | Asp | Val | Glu | Val<br>970 | Ala | Ser | Asp | Thr | Pro<br>975 | His | |
| CCG | GCG | CGG | ATT | GGC | CTG | AAC | TGC | CAG | CTG | GCG | CAG | GTA | GCA | GAG | CGG | 2976 |
| Pro | Ala | Arg | Ile<br>980 | Gly | Leu | Asn | Cys | Gln<br>985 | Leu | Ala | Gln | Val | Ala<br>990 | Glu | Arg | |
| GTA | AAC | TGG | CTC | GGA | TTA | GGG | CCG | CAA | GAA | AAC | TAT | CCC | GAC | CGC | CTT | 3024 |
| Val | Asn | Trp<br>995 | Leu | Gly | Leu | Gly | Pro<br>1000 | Gln | Glu | Asn | Tyr | Pro<br>1005 | Asp | Arg | Leu | |
| ACT | GCC | GCC | TGT | TTT | GAC | CGC | TGG | GAT | CTG | CCA | TTG | TCA | GAC | ATG | TAT | 3072 |
| Thr | Ala | Ala<br>1010 | Cys | Phe | Asp | Arg | Trp<br>1015 | Asp | Leu | Pro | Leu | Ser<br>1020 | Asp | Met | Tyr | |
| ACC | CCG | TAC | GTC | TTC | CCG | AGC | GAA | AAC | GGT | CTG | CGC | TGC | GGG | ACG | CGC | 3120 |
| Thr | Pro<br>1025 | Tyr | Val | Phe | Pro<br>1030 | Ser | Glu | Asn | Gly | Leu<br>1035 | Arg | Cys | Gly | Thr | Arg<br>1040 | |
| GAA | TTG | AAT | TAT | GGC | CCA | CAC | CAG | TGG | CGC | GGC | GAC | TTC | CAG | TTC | AAC | 3168 |
| Glu | Leu | Asn | Tyr | Gly<br>1045 | Pro | His | Gln | Trp | Arg<br>1050 | Gly | Asp | Phe | Gln | Phe<br>1055 | Asn | |
| ATC | AGC | CGC | TAC | AGT | CAA | CAG | CAA | CTG | ATG | GAA | ACC | AGC | CAT | CGC | CAT | 3216 |
| Ile | Ser | Arg | Tyr | Ser<br>1060 | Gln | Gln | Gln | Leu | Met<br>1065 | Glu | Thr | Ser | His | Arg<br>1070 | His | |
| CTG | CTG | CAC | GCG | GAA | GAA | GGC | ACA | TGG | CTG | AAT | ATC | GAC | GGT | TTC | CAT | 3264 |
| Leu | Leu | His<br>1075 | Ala | Glu | Glu | Gly | Thr<br>1080 | Trp | Leu | Asn | Ile | Asp<br>1085 | Gly | Phe | His | |
| ATG | GGG | ATT | GGT | GGC | GAC | GAC | TCC | TGG | AGC | CCG | TCA | GTA | TCG | GCG | GAA | 3312 |
| Met | Gly<br>1090 | Ile | Gly | Gly | Asp | Asp<br>1095 | Ser | Trp | Ser | Pro | Ser<br>1100 | Val | Ser | Ala | Glu | |
| TTC | CAG | CTG | AGC | GCC | GGT | CGC | TAC | CAT | TAC | CAG | TTG | GTC | TGG | TGT | CAA | 3360 |
| Phe | Gln<br>1105 | Leu | Ser | Ala | Gly<br>1110 | Arg | Tyr | His | Tyr | Gln<br>1115 | Leu | Val | Trp | Cys | Gln<br>1120 | |
| AAA | TA | | | | | | | | | | | | | | | 3365 |
| Lys | | | | | | | | | | | | | | | | |

( 2 ) INFORMATION FOR SEQ ID NO:2:

( i ) SEQUENCE CHARACTERISTICS:
        ( A ) LENGTH: 1121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ser Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly Met His Gly Ser
 65                  70                  75                  80

Gly Ala Trp Leu Leu Pro Val Ser Leu Val Lys Arg Lys Thr Thr Leu
                 85                  90                  95

Ala Pro Asn Thr Gln Thr Ala Ser Pro Arg Ala Leu Ala Asp Ser Leu
            100                 105                 110

Met Gln Leu Ala Arg Gln Val Ser Arg Leu Asn Arg Leu Ala Ala His
        115                 120                 125

Pro Pro Phe Ala Ser Trp Arg Asn Ser Glu Glu Ala Arg Thr Asp Arg
    130                 135                 140

Pro Ser Gln Gln Leu Arg Ser Leu Asn Gly Glu Trp Arg Phe Ala Trp
145                 150                 155                 160

Phe Pro Ala Pro Glu Ala Val Pro Glu Ser Trp Leu Glu Cys Asp Leu
                165                 170                 175

Pro Glu Ala Asp Thr Val Val Val Pro Ser Asn Trp Gln Met His Gly
            180                 185                 190

Tyr Asp Ala Pro Ile Tyr Thr Asn Val Thr Tyr Pro Ile Thr Val Asn
        195                 200                 205

Pro Pro Phe Val Pro Thr Glu Asn Pro Thr Gly Cys Tyr Ser Leu Thr
    210                 215                 220

Phe Asn Val Asp Glu Ser Trp Leu Gln Glu Gly Gln Thr Arg Ile Ile
225                 230                 235                 240

Phe Asp Gly Val Asn Ser Ala Phe His Leu Trp Cys Asn Gly Arg Trp
                245                 250                 255

Val Gly Tyr Gly Gln Asp Ser Arg Leu Pro Ser Glu Phe Asp Leu Ser
            260                 265                 270

Ala Phe Leu Arg Ala Gly Glu Asn Arg Leu Ala Val Met Val Leu Arg
        275                 280                 285

Trp Ser Asp Gly Ser Tyr Leu Glu Asp Gln Asp Met Trp Arg Met Ser
    290                 295                 300

Gly Ile Phe Arg Asp Val Ser Leu Leu His Lys Pro Thr Thr Gln Ile
305                 310                 315                 320

Ser Asp Phe His Val Ala Thr Arg Phe Asn Asp Asp Phe Ser Arg Ala
                325                 330                 335

Val Leu Glu Ala Glu Val Gln Met Cys Gly Glu Leu Arg Asp Tyr Leu
            340                 345                 350

Arg Val Thr Val Ser Leu Trp Gln Gly Glu Thr Gln Val Ala Ser Gly
        355                 360                 365
```

-continued

| | | | | | | | | | | | | | | |
|---|---|---|---|---|---|---|---|---|---|---|---|---|---|---|
| Thr | Ala | Pro | Phe | Gly | Gly | Glu | Ile | Ile | Asp | Glu | Arg | Gly | Gly | Tyr | Ala |
| 370 | | | | | 375 | | | | | 380 | | | | |
| Asp | Arg | Val | Thr | Leu | Arg | Leu | Asn | Val | Glu | Asn | Pro | Lys | Leu | Trp | Ser |
| 385 | | | | 390 | | | | | 395 | | | | | 400 |
| Ala | Glu | Ile | Pro | Asn | Leu | Tyr | Arg | Ala | Val | Glu | Leu | His | Thr | Ala |
| | | | | 405 | | | | 410 | | | | | 415 | |
| Asp | Gly | Thr | Leu | Ile | Glu | Ala | Glu | Ala | Cys | Asp | Val | Gly | Phe | Arg | Glu |
| | | | 420 | | | | 425 | | | | | 430 | | |
| Val | Arg | Ile | Glu | Asn | Gly | Leu | Leu | Leu | Leu | Asn | Gly | Lys | Pro | Leu | Leu |
| | | 435 | | | | | 440 | | | | | 445 | | |
| Ile | Arg | Gly | Val | Asn | Arg | His | Glu | His | His | Pro | Leu | His | Gly | Gln | Val |
| | 450 | | | | | 455 | | | | 460 | | | | | |
| Met | Asp | Glu | Gln | Thr | Met | Val | Gln | Asp | Ile | Leu | Leu | Met | Lys | Gln | Asn |
| 465 | | | | | 470 | | | | | 475 | | | | | 480 |
| Asn | Phe | Asn | Ala | Val | Arg | Cys | Ser | His | Tyr | Pro | Asn | His | Pro | Leu | Trp |
| | | | | 485 | | | | 490 | | | | | 495 | | |
| Tyr | Thr | Leu | Cys | Asp | Arg | Tyr | Gly | Leu | Tyr | Val | Val | Asp | Glu | Ala | Asn |
| | | | 500 | | | | 505 | | | | | 510 | | | |
| Ile | Glu | Thr | His | Gly | Met | Val | Pro | Met | Asn | Arg | Leu | Thr | Asp | Asp | Pro |
| | | 515 | | | | 520 | | | | | 525 | | | | |
| Arg | Trp | Leu | Pro | Ala | Met | Ser | Glu | Arg | Val | Thr | Arg | Met | Val | Gln | Arg |
| | 530 | | | | 535 | | | | | 540 | | | | | |
| Asp | Arg | Asn | His | Pro | Ser | Val | Ile | Ile | Trp | Ser | Leu | Gly | Asn | Glu | Ser |
| 545 | | | | 550 | | | | | 555 | | | | | | 560 |
| Gly | His | Gly | Ala | Asn | His | Asp | Ala | Leu | Tyr | Arg | Trp | Ile | Lys | Ser | Val |
| | | | 565 | | | | 570 | | | | | 575 | | | |
| Asp | Pro | Ser | Arg | Pro | Val | Gln | Tyr | Glu | Gly | Gly | Gly | Ala | Asp | Thr | Thr |
| | | | 580 | | | | 585 | | | | | 590 | | | |
| Ala | Thr | Asp | Ile | Ile | Cys | Pro | Met | Tyr | Ala | Arg | Val | Asp | Glu | Asp | Gln |
| | | 595 | | | | 600 | | | | | 605 | | | | |
| Pro | Phe | Pro | Ala | Val | Pro | Lys | Trp | Ser | Ile | Lys | Lys | Trp | Leu | Ser | Leu |
| | 610 | | | | | 615 | | | | | 620 | | | | |
| Pro | Gly | Glu | Thr | Arg | Pro | Leu | Ile | Leu | Cys | Glu | Tyr | Ala | His | Ala | Met |
| 625 | | | | | 630 | | | | | 635 | | | | | 640 |
| Gly | Asn | Ser | Leu | Gly | Gly | Phe | Ala | Lys | Tyr | Trp | Gln | Ala | Phe | Arg | Gln |
| | | | | 645 | | | | | 650 | | | | | 655 | |
| Tyr | Pro | Arg | Leu | Gln | Gly | Gly | Phe | Val | Trp | Asp | Trp | Val | Asp | Gln | Ser |
| | | | 660 | | | | | 665 | | | | | 670 | | |
| Leu | Ile | Lys | Tyr | Asp | Glu | Asn | Gly | Asn | Pro | Trp | Ser | Ala | Tyr | Gly | Gly |
| | | 675 | | | | | 680 | | | | | 685 | | | |
| Asp | Phe | Gly | Asp | Thr | Pro | Asn | Asp | Arg | Gln | Phe | Cys | Met | Asn | Gly | Leu |
| | 690 | | | | | 695 | | | | | 700 | | | | |
| Val | Phe | Ala | Asp | Arg | Thr | Pro | His | Pro | Ala | Leu | Thr | Glu | Ala | Lys | His |
| 705 | | | | | 710 | | | | | 715 | | | | | 720 |
| Gln | Gln | Gln | Phe | Phe | Gln | Phe | Arg | Leu | Ser | Gly | Gln | Thr | Ile | Glu | Val |
| | | | | 725 | | | | | 730 | | | | | 735 | |
| Thr | Ser | Glu | Tyr | Leu | Phe | Arg | His | Ser | Asp | Asn | Glu | Leu | Leu | His | Trp |
| | | | 740 | | | | | 745 | | | | | 750 | | |
| Met | Val | Ala | Leu | Asp | Gly | Lys | Pro | Leu | Ala | Ser | Gly | Glu | Val | Pro | Leu |
| | | 755 | | | | | 760 | | | | | 765 | | | |
| Asp | Val | Ala | Pro | Gln | Gly | Lys | Gln | Leu | Ile | Glu | Leu | Pro | Glu | Leu | Pro |
| | 770 | | | | | 775 | | | | | 780 | | | | |
| Gln | Pro | Glu | Ser | Ala | Gly | Gln | Leu | Trp | Leu | Thr | Val | Arg | Val | Val | Gln |
| 785 | | | | | 790 | | | | | 795 | | | | | 800 |

Pro Asn Ala Thr Ala Trp Ser Glu Ala Gly His Ile Ser Ala Trp Gln
            805                 810                 815

Gln Trp Arg Leu Ala Glu Asn Leu Ser Val Thr Leu Pro Ala Ala Ser
        820                 825                 830

His Ala Ile Pro His Leu Thr Thr Ser Glu Met Asp Phe Cys Ile Glu
        835                 840                 845

Leu Gly Asn Lys Arg Trp Gln Phe Asn Arg Gln Ser Gly Phe Leu Ser
    850                 855                 860

Gln Met Trp Ile Gly Asp Lys Lys Gln Leu Leu Thr Pro Leu Arg Asp
865                 870                 875                 880

Gln Phe Thr Arg Ala Pro Leu Asp Asn Asp Ile Gly Val Ser Glu Ala
            885                 890                 895

Thr Arg Ile Asp Pro Asn Ala Trp Val Glu Arg Trp Lys Ala Ala Gly
                900                 905                 910

His Tyr Gln Ala Glu Ala Ala Leu Leu Gln Cys Thr Ala Asp Thr Leu
        915                 920                 925

Ala Asp Ala Val Leu Ile Thr Thr Ala His Ala Trp Gln His Gln Gly
    930                 935                 940

Lys Thr Leu Phe Ile Ser Arg Lys Thr Tyr Arg Ile Asp Gly Ser Gly
945                 950                 955                 960

Gln Met Ala Ile Thr Val Asp Val Glu Val Ala Ser Asp Thr Pro His
                965                 970                 975

Pro Ala Arg Ile Gly Leu Asn Cys Gln Leu Ala Gln Val Ala Glu Arg
            980                 985                 990

Val Asn Trp Leu Gly Leu Gly Pro Gln Glu Asn Tyr Pro Asp Arg Leu
        995                 1000                1005

Thr Ala Ala Cys Phe Asp Arg Trp Asp Leu Pro Leu Ser Asp Met Tyr
    1010                1015                1020

Thr Pro Tyr Val Phe Pro Ser Glu Asn Gly Leu Arg Cys Gly Thr Arg
1025                1030                1035                1040

Glu Leu Asn Tyr Gly Pro His Gln Trp Arg Gly Asp Phe Gln Phe Asn
                1045                1050                1055

Ile Ser Arg Tyr Ser Gln Gln Gln Leu Met Glu Thr Ser His Arg His
            1060                1065                1070

Leu Leu His Ala Glu Glu Gly Thr Trp Leu Asn Ile Asp Gly Phe His
        1075                1080                1085

Met Gly Ile Gly Gly Asp Asp Ser Trp Ser Pro Ser Val Ser Ala Glu
    1090                1095                1100

Phe Gln Leu Ser Ala Gly Arg Tyr His Tyr Gln Leu Val Trp Cys Gln
1105                1110                1115                1120

Lys ( 2 ) INFORMATION FOR SEQ ID NO:3:

( i ) SEQUENCE CHARACTERISTICS:
        ( A ) LENGTH: 2845 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 193..2619

( x i ) SEQUENCE DESCRIPTION: SEQ ID NO:3:

TGTGATCTGC GTCCTTTTTT TCTCAGGAAA AAAAAATTTT ATAGACATTC AAAGAATAGA    60

```
AGCGATTGTC AAAATTCGCT TCTCCTTTCT TTTCCATTAT AACGTCTGAT CATTTTACGT        120

CTTCAGTGCC CTCCCTTGTT CGAAACTAGA TACTTTCGAA CACTTCTCCC CTTTTAATCT

ACAAAATTTT GT ATG GAT TTG TTT ATT GAA AGC AAG ATA AAC AGT TTA           180
              Met Asp Leu Phe Ile Glu Ser Lys Ile Asn Ser Leu
               1               5                   10
                                                                         228

TTA CAA TTT TTA TTT GGT TCC CGA CAG GAT TTT TTG AGA AAT TTT AAA
Leu Gln Phe Leu Phe Gly Ser Arg Gln Asp Phe Leu Arg Asn Phe Lys
         15              20                  25
                                                                         276

ACT TGG AGT AAC AAC AAT AAC AAT CTA TCG ATT TAT TTA TTA ATT TTT
Thr Trp Ser Asn Asn Asn Asn Asn Leu Ser Ile Tyr Leu Leu Ile Phe
         30              35                  40
                                                                         324

GGC ATA GTA GTA TTT TTT TAT AAA AAA CCA GAC CAT CTA AAC TAC ATT
Gly Ile Val Val Phe Phe Tyr Lys Lys Pro Asp His Leu Asn Tyr Ile
 45              50                  55                          60
                                                                         372

GTT GAG AGC GTT AGT GAA ATG ACA ACA AAC TTC AGA AAT AAT AAT AGC
Val Glu Ser Val Ser Glu Met Thr Thr Asn Phe Arg Asn Asn Asn Ser
                 65              70                  75
                                                                         420

CTT AGC CGT TGG TTG CCC AGA AGT AAG TTT ACC CAC TTA GAC GAA GAG
Leu Ser Arg Trp Leu Pro Arg Ser Lys Phe Thr His Leu Asp Glu Glu
         80              85                  90
                                                                         468

ATC TTG AAA AGA GGT GGT TTC ATT GCT GGT TTA GTT AAT GAT GGT AAC
Ile Leu Lys Arg Gly Gly Phe Ile Ala Gly Leu Val Asn Asp Gly Asn
         95              100                 105
                                                                         516

ACT TGT TTT ATG AAC TCT GTT TTG CAA TCA TTG GCA TCA TCC AGA GAA
Thr Cys Phe Met Asn Ser Val Leu Gln Ser Leu Ala Ser Ser Arg Glu
 110             115                 120
                                                                         564

TTA ATG GAG TTC TTG GAC AAT AAT GTC ATA AGG ACC TAT GAG GAG ATA
Leu Met Glu Phe Leu Asp Asn Asn Val Ile Arg Thr Tyr Glu Glu Ile
125                  130                 135                 140
                                                                         612

GAA CAA AAT GAA CAC AAT GAA GAA GGA AAC GGG CAA GAA TCT GCT CAA
Glu Gln Asn Glu His Asn Glu Glu Gly Asn Gly Gln Glu Ser Ala Gln
                 145                 150                 155
                                                                         660

GAT GAA GCC ACT CAT AAG AAA AAC ACT CGT AAG GGT GGC AAA GTT TAT
Asp Glu Ala Thr His Lys Lys Asn Thr Arg Lys Gly Gly Lys Val Tyr
             160                 165                 170
                                                                         708

GGT AAG CAT AAG AAG AAA TTG AAT AGG AAG TCA AGT TCG AAA GAA GAC
Gly Lys His Lys Lys Lys Leu Asn Arg Lys Ser Ser Ser Lys Glu Asp
         175                 180                 185
                                                                         756

GAA GAA AAG AGC CAG GAG CCA GAT ATC ACT TTC AGT GTC GCC TTA AGG
Glu Glu Lys Ser Gln Glu Pro Asp Ile Thr Phe Ser Val Ala Leu Arg
     190                 195                 200
                                                                         804

GAT CTA CTT TCT GCC TTA AAT GCG AAG TAT TAT CGG GAT AAA CCC TAT
Asp Leu Leu Ser Ala Leu Asn Ala Lys Tyr Tyr Arg Asp Lys Pro Tyr
205                 210                 215                 220
                                                                         852

TTC AAA ACC AAT AGT TTA TTG AAA GCA ATG TCC AAA TCT CCA AGA AAA
Phe Lys Thr Asn Ser Leu Leu Lys Ala Met Ser Lys Ser Pro Arg Lys
                 225                 230                 235
                                                                         900

AAT ATT CTT CTT GGC TAC GAC CAA GAG GAC GCG CAA GAA TTC TTC CAG
Asn Ile Leu Leu Gly Tyr Asp Gln Glu Asp Ala Gln Glu Phe Phe Gln
             240                 245                 250
                                                                         948

AAC ATA CTA GCC GAG TTG GAA AGT AAC GTT AAA TCA TTG AAT ACT GAA
Asn Ile Leu Ala Glu Leu Glu Ser Asn Val Lys Ser Leu Asn Thr Glu
         255                 260                 265
                                                                         996

AAA CTA GAT ACC ACT CCA GTT GCG AAA TCA GAA TTA CCC GAT GAT GCT        1044
Lys Leu Asp Thr Thr Pro Val Ala Lys Ser Glu Leu Pro Asp Asp Ala
     270                 275                 280

TTA GTA GGT CAA CTT AAC CTT GGT GAA GTT GGC ACT GTT TAC ATT CCA        1092
Leu Val Gly Gln Leu Asn Leu Gly Glu Val Gly Thr Val Tyr Ile Pro
285                 290                 295                 300
```

| | | | | | | | | | | | | | | | | |
|---|---|---|---|---|---|---|---|---|---|---|---|---|---|---|---|---|
| ACT | GAA | CAG | ATT | GAT | CCT | AAC | TCT | ATA | CTA | CAT | GAC | AAG | TCC | ATT | CAA | 1140 |
| Thr | Glu | Gln | Ile | Asp | Pro | Asn | Ser | Ile | Leu | His | Asp | Lys | Ser | Ile | Gln | |
| | | | | 305 | | | | | 310 | | | | | 315 | | |
| AAT | TTC | ACA | CCT | TTC | AAA | CTA | ATG | ACT | CCT | TTA | GAT | GGT | ATC | ACG | GCA | 1188 |
| Asn | Phe | Thr | Pro | Phe | Lys | Leu | Met | Thr | Pro | Leu | Asp | Gly | Ile | Thr | Ala | |
| | | 320 | | | | | 325 | | | | | 330 | | | | |
| GAA | AGA | ATT | GGT | TGT | TTA | CAG | TGT | GGT | GAG | AAC | GGT | GGC | ATA | AGA | TAT | 1236 |
| Glu | Arg | Ile | Gly | Cys | Leu | Gln | Cys | Gly | Glu | Asn | Gly | Gly | Ile | Arg | Tyr | |
| | | 335 | | | | | 340 | | | | | 345 | | | | |
| TCC | GTA | TTT | TCG | GGA | TTA | AGC | TTA | AAT | TTA | CCG | AAC | GAG | AAT | ATT | GGT | 1284 |
| Ser | Val | Phe | Ser | Gly | Leu | Ser | Leu | Asn | Leu | Pro | Asn | Glu | Asn | Ile | Gly | |
| | 350 | | | | | 355 | | | | | 360 | | | | | |
| TCC | ACT | TTA | AAA | TTA | TCT | CAG | TTA | TTA | AGC | GAC | TGG | AGT | AAA | CCT | GAA | 1332 |
| Ser | Thr | Leu | Lys | Leu | Ser | Gln | Leu | Leu | Ser | Asp | Trp | Ser | Lys | Pro | Glu | |
| 365 | | | | | 370 | | | | | 375 | | | | | 380 | |
| ATC | ATC | GAA | GGC | GTA | GAA | TGT | AAC | CGT | TGT | GCC | CTC | ACA | GCA | GCG | CAC | 1380 |
| Ile | Ile | Glu | Gly | Val | Glu | Cys | Asn | Arg | Cys | Ala | Leu | Thr | Ala | Ala | His | |
| | | | | 385 | | | | | 390 | | | | | 395 | | |
| TCT | CAT | TTA | TTT | GGT | CAG | TTG | AAA | GAA | TTT | GAA | AAA | AAA | CCT | GAG | GGT | 1428 |
| Ser | His | Leu | Phe | Gly | Gln | Leu | Lys | Glu | Phe | Glu | Lys | Lys | Pro | Glu | Gly | |
| | | | 400 | | | | | 405 | | | | | 410 | | | |
| TCG | ATC | CCA | GAA | AAG | CCA | ATT | AAC | GCT | GTA | AAA | GAT | AGG | GTC | CAT | CAA | 1476 |
| Ser | Ile | Pro | Glu | Lys | Pro | Ile | Asn | Ala | Val | Lys | Asp | Arg | Val | His | Gln | |
| | | 415 | | | | | 420 | | | | | 425 | | | | |
| ATC | GAA | GAA | GTT | CTT | GCC | AAA | CCA | GTT | ATT | GAC | GAT | GAA | GAT | TAT | AAG | 1524 |
| Ile | Glu | Glu | Val | Leu | Ala | Lys | Pro | Val | Ile | Asp | Asp | Glu | Asp | Tyr | Lys | |
| | 430 | | | | | 435 | | | | | 440 | | | | | |
| AAG | TTG | CAT | ACA | GCA | AAT | ATG | GTA | CGT | AAA | TGC | TCT | AAA | TCT | AAG | CAG | 1572 |
| Lys | Leu | His | Thr | Ala | Asn | Met | Val | Arg | Lys | Cys | Ser | Lys | Ser | Lys | Gln | |
| 445 | | | | | 450 | | | | | 455 | | | | | 460 | |
| ATT | TTA | ATA | TCA | AGA | CCT | CCA | CCA | TTA | TTA | TCC | ATT | CAT | ATC | AAC | AGA | 1620 |
| Ile | Leu | Ile | Ser | Arg | Pro | Pro | Pro | Leu | Leu | Ser | Ile | His | Ile | Asn | Arg | |
| | | | | 465 | | | | | 470 | | | | | 475 | | |
| TCC | GTA | TTT | GAT | CCA | AGA | ACG | TAC | ATG | ATT | AGA | AAA | AAT | AAC | TCG | AAA | 1668 |
| Ser | Val | Phe | Asp | Pro | Arg | Thr | Tyr | Met | Ile | Arg | Lys | Asn | Asn | Ser | Lys | |
| | | | 480 | | | | | 485 | | | | | 490 | | | |
| GTA | TTG | TTT | AAG | TCA | AGG | TTG | AAT | CTT | GCC | CCA | TGG | TGT | TGT | GAT | ATT | 1716 |
| Val | Leu | Phe | Lys | Ser | Arg | Leu | Asn | Leu | Ala | Pro | Trp | Cys | Cys | Asp | Ile | |
| | | 495 | | | | | 500 | | | | | 505 | | | | |
| AAT | GAA | ATC | AAT | TTG | GAT | GCT | CGT | TTG | CCA | ATG | TCA | AAA | AAG | GAA | AAA | 1764 |
| Asn | Glu | Ile | Asn | Leu | Asp | Ala | Arg | Leu | Pro | Met | Ser | Lys | Lys | Glu | Lys | |
| | 510 | | | | | 515 | | | | | 520 | | | | | |
| GCT | GCG | CAA | CAA | GAT | TCA | AGT | GAA | GAT | GAA | AAC | ATT | GGC | GGT | GAA | TAC | 1812 |
| Ala | Ala | Gln | Gln | Asp | Ser | Ser | Glu | Asp | Glu | Asn | Ile | Gly | Gly | Glu | Tyr | |
| 525 | | | | | 530 | | | | | 535 | | | | | 540 | |
| TAT | ACG | AAA | TTA | CAT | GAA | CGC | TTC | GAG | CAG | GAA | TTT | GAA | GAC | AGC | GAG | 1860 |
| Tyr | Thr | Lys | Leu | His | Glu | Arg | Phe | Glu | Gln | Glu | Phe | Glu | Asp | Ser | Glu | |
| | | | | 545 | | | | | 550 | | | | | 555 | | |
| GAA | GAA | AAA | GAA | TAC | GAT | GAC | GCA | GAG | GGG | AAC | TAT | GCG | TCT | CAT | TAC | 1908 |
| Glu | Glu | Lys | Glu | Tyr | Asp | Asp | Ala | Glu | Gly | Asn | Tyr | Ala | Ser | His | Tyr | |
| | | | 560 | | | | | 565 | | | | | 570 | | | |
| AAT | CAT | ACC | AAG | GAT | ATC | AGT | AAC | TAT | GAT | CCC | CTA | AAC | GGT | GAA | GTC | 1956 |
| Asn | His | Thr | Lys | Asp | Ile | Ser | Asn | Tyr | Asp | Pro | Leu | Asn | Gly | Glu | Val | |
| | | 575 | | | | | 580 | | | | | 585 | | | | |
| GAT | GGC | GTG | ACA | TCC | GAT | GAT | GAA | GAT | GAG | TAC | ATT | GAA | GAA | ACC | GAT | 2004 |
| Asp | Gly | Val | Thr | Ser | Asp | Asp | Glu | Asp | Glu | Tyr | Ile | Glu | Glu | Thr | Asp | |
| | 590 | | | | | 595 | | | | | 600 | | | | | |
| GCT | TTA | GGG | AAT | ACA | ATC | AAA | AAA | AGG | ATC | ATA | GAA | CAT | TCT | GAT | GTT | 2052 |
| Ala | Leu | Gly | Asn | Thr | Ile | Lys | Lys | Arg | Ile | Ile | Glu | His | Ser | Asp | Val | |
| 605 | | | | | 610 | | | | | 615 | | | | | 620 | |

| | | | | | | | | | | | | | | | | |
|---|---|---|---|---|---|---|---|---|---|---|---|---|---|---|---|---|
| GAA | AAC | GAG | AAT | GTA | AAA | GAT | AAT | GAA | GAA | CTG | CAA | GAA | ATC | GAC | AAT | 2100 |
| Glu | Asn | Glu | Asn | Val 625 | Lys | Asp | Asn | Glu 630 | Glu | Leu | Gln | Glu | Ile 635 | Asp | Asn | |
| GTG | AGC | CTT | GAC | GAA | CCA | AAG | ATC | AAT | GTT | GAA | GAT | CAA | CTA | GAA | ACA | 2148 |
| Val | Ser | Leu | Asp 640 | Glu | Pro | Lys | Ile | Asn 645 | Val | Glu | Asp | Gln | Leu 650 | Glu | Thr | |
| TCA | TCT | GAT | GAG | GAA | GAT | GTT | ATA | CCA | GCT | CCA | CCT | ATC | AAT | TAT | GCT | 2196 |
| Ser | Ser | Asp 655 | Glu | Glu | Asp | Val | Ile 660 | Pro | Ala | Pro | Pro | Ile 665 | Asn | Tyr | Ala | |
| AGG | TCA | TTT | TCC | ACA | GTT | CCA | GCC | ACT | CCA | TTG | ACA | TAT | TCA | TTG | CGC | 2244 |
| Arg | Ser 670 | Phe | Ser | Thr | Val | Pro 675 | Ala | Thr | Pro | Leu | Thr 680 | Tyr | Ser | Leu | Arg | |
| TCT | GTC | ATT | GTT | CAC | TAC | GGT | ACC | CAT | AAT | TAT | GGT | CAT | TAC | ATT | GCA | 2292 |
| Ser 685 | Val | Ile | Val | His | Tyr 690 | Gly | Thr | His | Asn | Tyr 695 | Gly | His | Tyr | Ile | Ala 700 | |
| TTT | AGA | AAA | TAC | AGG | GGT | TGT | TGG | TGG | AGA | ATA | TCT | GAT | GAG | ACT | GTG | 2340 |
| Phe | Arg | Lys | Tyr | Arg 705 | Gly | Cys | Trp | Trp | Arg 710 | Ile | Ser | Asp | Glu | Thr 715 | Val | |
| TAC | GTT | GTG | GAC | GAA | GCT | GAA | GTC | CTT | TCA | ACA | CCC | GGT | GTA | TTT | ATG | 2388 |
| Tyr | Val | Val | Asp 720 | Glu | Ala | Glu | Val | Leu 725 | Ser | Thr | Pro | Gly | Val 730 | Phe | Met | |
| TTA | TTT | TAC | GAA | TAT | GAC | TTT | GAT | GAA | GAA | ACT | GGG | AAG | ATG | AAG | GAT | 2436 |
| Leu | Phe | Tyr 735 | Glu | Tyr | Asp | Phe | Asp 740 | Glu | Glu | Thr | Gly | Lys 745 | Met | Lys | Asp | |
| GAT | TTG | GAA | GCT | ATT | CAG | AGT | AAT | AAT | GAA | GAA | GAT | GAT | GAA | AAA | GAG | 2484 |
| Asp | Leu 750 | Glu | Ala | Ile | Gln | Ser 755 | Asn | Asn | Glu | Glu | Asp 760 | Asp | Glu | Lys | Glu | |
| CAG | GAG | CAA | AAA | GGA | GTC | CAG | GAG | CCA | AAG | GAA | AGC | CAA | GAG | CAA | GGA | 2532 |
| Gln 765 | Glu | Gln | Lys | Gly | Val 770 | Gln | Glu | Pro | Lys | Glu 775 | Ser | Gln | Glu | Gln | Gly 780 | |
| GAA | GGT | GAA | GAG | CAA | GAG | GAA | GGT | CAA | GAG | CAG | ATG | AAG | TTC | GAG | AGA | 2580 |
| Glu | Gly | Glu | Glu | Gln 785 | Glu | Glu | Gly | Gln | Glu 790 | Gln | Met | Lys | Phe | Glu 795 | Arg | |
| ACA | GAA | GAC | CAT | AGA | GAT | ATT | TCT | GGT | AAA | GAT | GTA | AAC | TAAGTTATAA | | | 2629 |
| Thr | Glu | Asp | His 800 | Arg | Asp | Ile | Ser | Gly 805 | Lys | Asp | Val | Asn | | | | |

ATACGATATC CGTAATTGTG TAAATAACAA TAACTATAAT TAAATTGAAT AATTAAAAG     2689

CTACGTTATT CGTTAAATCA ATTGTTTAGC TAGTTACGAA TGTCTAAAGT TTTTGTAGG     2749

CAATTGCAAA AATCACTTCC ATTATTATAC AAATCCTTCT AAGCTTCATT TTTCTTACC     2809

TTGTACTTCT TCAACTTTTT CTCTTCTCTT CTCTCC     2845

( 2 ) INFORMATION FOR SEQ ID NO:4:

( i ) SEQUENCE CHARACTERISTICS:
        ( A ) LENGTH: 809 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met 1 | Asp | Leu | Phe | Ile 5 | Glu | Ser | Lys | Ile | Asn 10 | Ser | Leu | Leu | Gln | Phe 15 | Leu |
| Phe | Gly | Ser | Arg 20 | Gln | Asp | Phe | Leu | Arg 25 | Asn | Phe | Lys | Thr | Trp 30 | Ser | Asn |
| Asn | Asn | Asn 35 | Asn | Leu | Ser | Ile | Tyr 40 | Leu | Leu | Ile | Phe | Gly 45 | Ile | Val | Val |
| Phe | Phe 50 | Tyr | Lys | Lys | Pro | Asp 55 | His | Leu | Asn | Tyr | Ile 60 | Val | Glu | Ser | Val |

-continued

| | | | | | | | | | | | | | | | |
|---|---|---|---|---|---|---|---|---|---|---|---|---|---|---|---|
| Ser | Glu | Met | Thr | Thr | Asn | Phe | Arg | Asn | Asn | Asn | Ser | Leu | Ser | Arg | Trp |
| 65 | | | | | 70 | | | | 75 | | | | | | 80 |
| Leu | Pro | Arg | Ser | Lys | Phe | Thr | His | Leu | Asp | Glu | Glu | Ile | Leu | Lys | Arg |
| | | | | 85 | | | | | 90 | | | | | 95 | |
| Gly | Gly | Phe | Ile | Ala | Gly | Leu | Val | Asn | Asp | Gly | Asn | Thr | Cys | Phe | Met |
| | | | 100 | | | | | 105 | | | | | 110 | | |
| Asn | Ser | Val | Leu | Gln | Ser | Leu | Ala | Ser | Ser | Arg | Glu | Leu | Met | Glu | Phe |
| | | | 115 | | | | 120 | | | | | 125 | | | |
| Leu | Asp | Asn | Asn | Val | Ile | Arg | Thr | Tyr | Glu | Glu | Ile | Glu | Gln | Asn | Glu |
| | 130 | | | | | 135 | | | | | 140 | | | | |
| His | Asn | Glu | Glu | Gly | Asn | Gly | Gln | Glu | Ser | Ala | Gln | Asp | Glu | Ala | Thr |
| 145 | | | | | 150 | | | | | 155 | | | | | 160 |
| His | Lys | Lys | Asn | Thr | Arg | Lys | Gly | Gly | Lys | Val | Tyr | Gly | Lys | His | Lys |
| | | | | 165 | | | | | 170 | | | | | 175 | |
| Lys | Lys | Leu | Asn | Arg | Lys | Ser | Ser | Ser | Lys | Glu | Asp | Glu | Glu | Lys | Ser |
| | | | | 180 | | | | | 185 | | | | | 190 | |
| Gln | Glu | Pro | Asp | Ile | Thr | Phe | Ser | Val | Ala | Leu | Arg | Asp | Leu | Leu | Ser |
| | | | 195 | | | | 200 | | | | | 205 | | | |
| Ala | Leu | Asn | Ala | Lys | Tyr | Tyr | Arg | Asp | Lys | Pro | Tyr | Phe | Lys | Thr | Asn |
| | 210 | | | | | 215 | | | | | 220 | | | | |
| Ser | Leu | Leu | Lys | Ala | Met | Ser | Lys | Ser | Pro | Arg | Lys | Asn | Ile | Leu | Leu |
| 225 | | | | | 230 | | | | | 235 | | | | | 240 |
| Gly | Tyr | Asp | Gln | Glu | Asp | Ala | Gln | Glu | Phe | Phe | Gln | Asn | Ile | Leu | Ala |
| | | | | 245 | | | | | 250 | | | | | 255 | |
| Glu | Leu | Glu | Ser | Asn | Val | Lys | Ser | Leu | Asn | Thr | Glu | Lys | Leu | Asp | Thr |
| | | | | 260 | | | | | 265 | | | | | 270 | |
| Thr | Pro | Val | Ala | Lys | Ser | Glu | Leu | Pro | Asp | Asp | Ala | Leu | Val | Gly | Gln |
| | | | 275 | | | | | 280 | | | | | 285 | | |
| Leu | Asn | Leu | Gly | Glu | Val | Gly | Thr | Val | Tyr | Ile | Pro | Thr | Glu | Gln | Ile |
| | 290 | | | | | 295 | | | | | 300 | | | | |
| Asp | Pro | Asn | Ser | Ile | Leu | His | Asp | Lys | Ser | Ile | Gln | Asn | Phe | Thr | Pro |
| 305 | | | | | 310 | | | | | 315 | | | | | 320 |
| Phe | Lys | Leu | Met | Thr | Pro | Leu | Asp | Gly | Ile | Thr | Ala | Glu | Arg | Ile | Gly |
| | | | | 325 | | | | | 330 | | | | | 335 | |
| Cys | Leu | Gln | Cys | Gly | Glu | Asn | Gly | Gly | Ile | Arg | Tyr | Ser | Val | Phe | Ser |
| | | | 340 | | | | | 345 | | | | | 350 | | |
| Gly | Leu | Ser | Leu | Asn | Leu | Pro | Asn | Glu | Asn | Ile | Gly | Ser | Thr | Leu | Lys |
| | | | 355 | | | | | 360 | | | | | 365 | | |
| Leu | Ser | Gln | Leu | Leu | Ser | Asp | Trp | Ser | Lys | Pro | Glu | Ile | Ile | Glu | Gly |
| | 370 | | | | | 375 | | | | | 380 | | | | |
| Val | Glu | Cys | Asn | Arg | Cys | Ala | Leu | Thr | Ala | Ala | His | Ser | His | Leu | Phe |
| 385 | | | | | 390 | | | | | 395 | | | | | 400 |
| Gly | Gln | Leu | Lys | Glu | Phe | Glu | Lys | Lys | Pro | Glu | Gly | Ser | Ile | Pro | Glu |
| | | | | 405 | | | | | 410 | | | | | 415 | |
| Lys | Pro | Ile | Asn | Ala | Val | Lys | Asp | Arg | Val | His | Gln | Ile | Glu | Glu | Val |
| | | | 420 | | | | | 425 | | | | | 430 | | |
| Leu | Ala | Lys | Pro | Val | Ile | Asp | Asp | Glu | Asp | Tyr | Lys | Lys | Leu | His | Thr |
| | | 435 | | | | | 440 | | | | | 445 | | | |
| Ala | Asn | Met | Val | Arg | Lys | Cys | Ser | Lys | Ser | Lys | Gln | Ile | Leu | Ile | Ser |
| | 450 | | | | | 455 | | | | | 460 | | | | |
| Arg | Pro | Pro | Pro | Leu | Leu | Ser | Ile | His | Ile | Asn | Arg | Ser | Val | Phe | Asp |
| 465 | | | | | 470 | | | | | 475 | | | | | 480 |
| Pro | Arg | Thr | Tyr | Met | Ile | Arg | Lys | Asn | Asn | Ser | Lys | Val | Leu | Phe | Lys |
| | | | | 485 | | | | | 490 | | | | | 495 | |

| | | | | | | | | | | | | | | |
|---|---|---|---|---|---|---|---|---|---|---|---|---|---|---|
| Ser | Arg | Leu | Asn | Leu | Ala | Pro | Trp | Cys | Cys | Asp | Ile | Asn | Glu | Ile | Asn |
| | | | 500 | | | | | 505 | | | | 510 | | | |
| Leu | Asp | Ala | Arg | Leu | Pro | Met | Ser | Lys | Lys | Glu | Lys | Ala | Ala | Gln | Gln |
| | | 515 | | | | | 520 | | | | | 525 | | | |
| Asp | Ser | Ser | Glu | Asp | Glu | Asn | Ile | Gly | Gly | Glu | Tyr | Tyr | Thr | Lys | Leu |
| | 530 | | | | | 535 | | | | | 540 | | | | |
| His | Glu | Arg | Phe | Glu | Gln | Glu | Phe | Glu | Asp | Ser | Glu | Glu | Lys | Glu |
| 545 | | | | | 550 | | | | | 555 | | | | 560 |
| Tyr | Asp | Asp | Ala | Glu | Gly | Asn | Tyr | Ala | Ser | His | Tyr | Asn | His | Thr | Lys |
| | | | | 565 | | | | | 570 | | | | | 575 | |
| Asp | Ile | Ser | Asn | Tyr | Asp | Pro | Leu | Asn | Gly | Glu | Val | Asp | Gly | Val | Thr |
| | | | 580 | | | | | 585 | | | | | 590 | | |
| Ser | Asp | Asp | Glu | Asp | Glu | Tyr | Ile | Glu | Glu | Thr | Asp | Ala | Leu | Gly | Asn |
| | | 595 | | | | | 600 | | | | | 605 | | | |
| Thr | Ile | Lys | Lys | Arg | Ile | Ile | Glu | His | Ser | Asp | Val | Glu | Asn | Glu | Asn |
| | 610 | | | | | 615 | | | | | 620 | | | | |
| Val | Lys | Asp | Asn | Glu | Glu | Leu | Gln | Glu | Ile | Asp | Asn | Val | Ser | Leu | Asp |
| 625 | | | | | 630 | | | | | 635 | | | | | 640 |
| Glu | Pro | Lys | Ile | Asn | Val | Glu | Asp | Gln | Leu | Glu | Thr | Ser | Ser | Asp | Glu |
| | | | | 645 | | | | | 650 | | | | | 655 | |
| Glu | Asp | Val | Ile | Pro | Ala | Pro | Pro | Ile | Asn | Tyr | Ala | Arg | Ser | Phe | Ser |
| | | | 660 | | | | | 665 | | | | | 670 | | |
| Thr | Val | Pro | Ala | Thr | Pro | Leu | Thr | Tyr | Ser | Leu | Arg | Ser | Val | Ile | Val |
| | | 675 | | | | | 680 | | | | | 685 | | | |
| His | Tyr | Gly | Thr | His | Asn | Tyr | Gly | His | Tyr | Ile | Ala | Phe | Arg | Lys | Tyr |
| | 690 | | | | | 695 | | | | | 700 | | | | |
| Arg | Gly | Cys | Trp | Trp | Arg | Ile | Ser | Asp | Glu | Thr | Val | Tyr | Val | Val | Asp |
| 705 | | | | | 710 | | | | | 715 | | | | | 720 |
| Glu | Ala | Glu | Val | Leu | Ser | Thr | Pro | Gly | Val | Phe | Met | Leu | Phe | Tyr | Glu |
| | | | | 725 | | | | | 730 | | | | | 735 | |
| Tyr | Asp | Phe | Asp | Glu | Glu | Thr | Gly | Lys | Met | Lys | Asp | Asp | Leu | Glu | Ala |
| | | | 740 | | | | | 745 | | | | | 750 | | |
| Ile | Gln | Ser | Asn | Asn | Glu | Glu | Asp | Asp | Glu | Lys | Glu | Gln | Glu | Gln | Lys |
| | | 755 | | | | | 760 | | | | | 765 | | | |
| Gly | Val | Gln | Glu | Pro | Lys | Glu | Ser | Gln | Glu | Gln | Gly | Glu | Gly | Glu | Glu |
| | 770 | | | | | 775 | | | | | 780 | | | | |
| Gln | Glu | Glu | Gly | Gln | Glu | Gln | Met | Lys | Phe | Glu | Arg | Thr | Glu | Asp | His |
| 785 | | | | | 790 | | | | | 795 | | | | | 800 |
| Arg | Asp | Ile | Ser | Gly | Lys | Asp | Val | Asn |
| | | | | | 805 | | | |

(2) INFORMATION FOR SEQ ID NO:5:

(i) SEQUENCE CHARACTERISTICS:
    (A) LENGTH: 6008 base pairs
    (B) TYPE: nucleic acid
    (C) STRANDEDNESS: double
    (D) TOPOLOGY: linear (ix) FEATURE:
    (A) NAME/KEY: CDS
    (B) LOCATION: 983..4774

(xi) SEQUENCE DESCRIPTION: SEQ ID NO:5:

| | | | | | |
|---|---|---|---|---|---|
| GCATGCTCCC | AAGTGTCAGA | ATTTATCAGA | TGCTCAGGCT | GCATTTTTGG | ACCGTGTTAT | 60 |
| TCGTGTAGAT | CAAGCTGGCG | AATTAGGTGC | AGACTACATC | TACGCTGGCC | AGTACTTCGT | 120 |

| | |
|---|---|
| GTTGGCTCAT AGGTACCCTC ACTTGAAACC TGTGCTAAAG CACATATGGG ACCAGGAGAT | 180 |
| ACATCATCAT AATACTTTTA ACAATTTGCA ATTGAAAAGG AGAGTCAGGC CTTCCTTATT | 240 |
| AACGCCTTTG TGGAAGGCAG GAGCCTTTGC AATGGGGGCT GGTACCGCAT TGATTTCTCC | 300 |
| AGAAGCAGCT ATGGCTTGTA CTGAAGCTGT CGAGACAGTA ATCGGAGGGC ACTACAATGG | 360 |
| CCAATTGCGA AACTTGGCCA ATCAATTCAA TTTAGAAAGA ACAGATGGAA CAAAGGGTCC | 420 |
| AAGTGAGGAA ATCAAATCCT TAACTTCTAC TATCCAACAG TTCAGGGATG ACGAGCTAGA | 480 |
| GCATCTAGAC ACCGCTATCA AGCATGATTC GTATATGGCA GTTCCATATA CAGTTATCAC | 540 |
| TGAAGGTATT AAAACGATTT GCAGAGTAGC TATATGGAGT GCCGAAAGAA TTTAACCACC | 600 |
| AGAAGTGGC ATACATCAGT CGCGTTATGC CAGAAAAGGA GAATTGAAAG GAAAACGGTT | 660 |
| TGATAAATGT CCTAATTAAA CTATCATGTA TAAAATTATG TATCATCCTT ACGCATTTTA | 720 |
| ACGCTATATG ACCAATATGA CAGGAATAGA TACACTGTCT ATAATTATGT AAATGGGGTA | 780 |
| TGGGTTCATA GTCTAAGGGT GAGTACAAAC TGGATCTTTA ACAAGAGTAA CAGTTAATTA | 840 |
| GAGCAAAACT ATAGTACATA TAGCTTGAAA AAAACAAGCG GCTTGCCATT GGAAGAACAT | 900 |
| TGCATAAAAA CGGGGCCACT GCTAATAATA AAGTGGTAAT TAAAAAGAAA GCTTTGTTC | 960 |

```
AAGGTTAAGA AGGTATAAGG AA ATG CCG AAC GAA GAT AAT GAA CTT CAA AAA         1012
                         Met Pro Asn Glu Asp Asn Glu Leu Gln Lys
                          1           5                      10

GCA ATT GAG AAC CAT CAT AAT CAA CTA CTA AAC CAG GAT AAA GAA AAT          1060
Ala Ile Glu Asn His His Asn Gln Leu Leu Asn Gln Asp Lys Glu Asn
             15                  20                  25

GCT GAC AGA AAT GGG TCT GTT ATA GAA GAC CTC CCA TTA TAC GGG ACA          1108
Ala Asp Arg Asn Gly Ser Val Ile Glu Asp Leu Pro Leu Tyr Gly Thr
                 30                  35                  40

AGT ATA AAC CAG CAG TCT ACC CCT GGA GAT GTT GAC GAT GGA AAA CAC          1156
Ser Ile Asn Gln Gln Ser Thr Pro Gly Asp Val Asp Asp Gly Lys His
             45                  50                  55

TTA CTG TAT CCA GAT ATT GCC ACC AAC CTA CCA CTG AAG ACT TCT GAC          1204
Leu Leu Tyr Pro Asp Ile Ala Thr Asn Leu Pro Leu Lys Thr Ser Asp
         60                  65                  70

AGA CTT TTG GAC GAT ATA CTT TGC GAT ACT ATT TTT CTC AAT TCT ACA          1252
Arg Leu Leu Asp Asp Ile Leu Cys Asp Thr Ile Phe Leu Asn Ser Thr
 75                  80                  85                  90

GAC CCG AAG GTC ATG CAA AAG GGC CTG CAA TCG AGG GGT ATT TTA AAA          1300
Asp Pro Lys Val Met Gln Lys Gly Leu Gln Ser Arg Gly Ile Leu Lys
                 95                 100                 105

GAG TCT ATG CTT TCT TAC TCA ACT TTC AGA AGT AGT ATT CGC CCT AAC          1348
Glu Ser Met Leu Ser Tyr Ser Thr Phe Arg Ser Ser Ile Arg Pro Asn
             110                 115                 120

TGC TTG GGT TCA TTA ACT GAT CAA GTG GTT TTT CAA ACA AAA TCC GAG          1396
Cys Leu Gly Ser Leu Thr Asp Gln Val Val Phe Gln Thr Lys Ser Glu
         125                 130                 135

TAT GAT TCC ATT TCA TGC CCA AAA TAT AAT AAA ATA CAT GTA TTT CAG          1444
Tyr Asp Ser Ile Ser Cys Pro Lys Tyr Asn Lys Ile His Val Phe Gln
 140                 145                 150

GCG GTC ATC TTT AAT CCA TCA CTG GCA GAA CAG CAA ATT TCA ACT TTT          1492
Ala Val Ile Phe Asn Pro Ser Leu Ala Glu Gln Gln Ile Ser Thr Phe
155                 160                 165                 170

GAT GAT ATT GTT AAA ATT CCT ATT TAT CAT CTT AAG GTT AGC GTA AAA          1540
Asp Asp Ile Val Lys Ile Pro Ile Tyr His Leu Lys Val Ser Val Lys
                 175                 180                 185

GTC CGC CAA GAA CTG GAG CGG TTG AAG AAG CAT GTC GGT GTT ACT CAA          1588
Val Arg Gln Glu Leu Glu Arg Leu Lys Lys His Val Gly Val Thr Gln
             190                 195                 200
```

-continued

| | | | | | | | | | | | | | | | | |
|---|---|---|---|---|---|---|---|---|---|---|---|---|---|---|---|---|
| TTC | CAC | TCA | CTA | GAT | CAT | TTG | CAC | GAA | TAC | GAT | CGA | GTA | GAC | CTT | TCG | 1636 |
| Phe | His | Ser | Leu | Asp | His | Leu | His | Glu | Tyr | Asp | Arg | Val | Asp | Leu | Ser | |
| | | 205 | | | | | 210 | | | | | 215 | | | | |
| ACT | TTT | GAT | TCT | TCC | GAT | CCT | AAT | TTG | TTG | GAT | TAC | GGT | ATT | TAC | GTT | 1684 |
| Thr | Phe | Asp | Ser | Ser | Asp | Pro | Asn | Leu | Leu | Asp | Tyr | Gly | Ile | Tyr | Val | |
| | 220 | | | | | 225 | | | | | 230 | | | | | |
| TCT | GAT | GAT | ACT | AAC | AAA | CTG | ATC | TTG | ATT | GAA | ATT | TTT | AAA | CCC | GAG | 1732 |
| Ser | Asp | Asp | Thr | Asn | Lys | Leu | Ile | Leu | Ile | Glu | Ile | Phe | Lys | Pro | Glu | |
| 235 | | | | | 240 | | | | | 245 | | | | | 250 | |
| TTT | AAT | TCA | CCT | GAA | GAG | CAT | GAG | AGT | TTT | ACT | GCC | GAC | GCA | ATT | AAG | 1780 |
| Phe | Asn | Ser | Pro | Glu | Glu | His | Glu | Ser | Phe | Thr | Ala | Asp | Ala | Ile | Lys | |
| | | | | 255 | | | | | 260 | | | | | 265 | | |
| AAG | AGA | TAC | AAT | GCT | ATG | TGT | GTA | AAA | AAT | GAA | TCA | CTA | GAT | AAA | AGC | 1828 |
| Lys | Arg | Tyr | Asn | Ala | Met | Cys | Val | Lys | Asn | Glu | Ser | Leu | Asp | Lys | Ser | |
| | | | 270 | | | | | 275 | | | | | 280 | | | |
| GAG | ACG | CCA | TCT | CAA | GTT | GAC | TGT | TTT | TAC | ACA | CTT | TTT | AAA | ATT | TTT | 1876 |
| Glu | Thr | Pro | Ser | Gln | Val | Asp | Cys | Phe | Tyr | Thr | Leu | Phe | Lys | Ile | Phe | |
| | | 285 | | | | | 290 | | | | | 295 | | | | |
| AAA | GGG | CCT | TTG | ACG | AGG | AAA | AGT | AAA | GCG | GAA | CCT | ACA | AAG | ACA | ATT | 1924 |
| Lys | Gly | Pro | Leu | Thr | Arg | Lys | Ser | Lys | Ala | Glu | Pro | Thr | Lys | Thr | Ile | |
| | 300 | | | | | 305 | | | | | 310 | | | | | |
| GAT | TCT | GGA | AAT | TTG | GCC | CTT | AAC | ACT | CAC | CTG | AAT | CCT | GAA | TGG | TTA | 1972 |
| Asp | Ser | Gly | Asn | Leu | Ala | Leu | Asn | Thr | His | Leu | Asn | Pro | Glu | Trp | Leu | |
| 315 | | | | | 320 | | | | | 325 | | | | | 330 | |
| ACG | TCC | AAG | TAT | GGA | TTT | CAA | GCA | AGC | TCA | GAA | ATC | GAT | GAG | GAA | ACT | 2020 |
| Thr | Ser | Lys | Tyr | Gly | Phe | Gln | Ala | Ser | Ser | Glu | Ile | Asp | Glu | Glu | Thr | |
| | | | | 335 | | | | | 340 | | | | | 345 | | |
| AAT | GAG | ATA | TTT | ACT | GAA | TAC | GTC | CCT | CCA | GAT | ATG | GTG | GAC | TAT | GTA | 2068 |
| Asn | Glu | Ile | Phe | Thr | Glu | Tyr | Val | Pro | Pro | Asp | Met | Val | Asp | Tyr | Val | |
| | | | 350 | | | | | 355 | | | | | 360 | | | |
| AAC | GAT | TTG | GAG | ACA | AGA | AAA | ATT | CGA | GAA | TCG | TTT | GTG | AGG | AAG | TGT | 2116 |
| Asn | Asp | Leu | Glu | Thr | Arg | Lys | Ile | Arg | Glu | Ser | Phe | Val | Arg | Lys | Cys | |
| | | 365 | | | | | 370 | | | | | 375 | | | | |
| TTA | CAA | CTG | ATA | TTT | TGG | GGT | CAA | CTA | TCT | ACC | TCA | TTA | CTG | GCA | CCT | 2164 |
| Leu | Gln | Leu | Ile | Phe | Trp | Gly | Gln | Leu | Ser | Thr | Ser | Leu | Leu | Ala | Pro | |
| | 380 | | | | | 385 | | | | | 390 | | | | | |
| AAT | TCT | CCC | TTG | AAA | AAT | ACG | AAA | AGC | GTA | AAG | GGA | ATG | TCT | TCA | TTA | 2212 |
| Asn | Ser | Pro | Leu | Lys | Asn | Thr | Lys | Ser | Val | Lys | Gly | Met | Ser | Ser | Leu | |
| 395 | | | | | 400 | | | | | 405 | | | | | 410 | |
| CAA | ACT | TCT | TTC | TCA | ACA | CTA | CCT | TGG | TTC | CAT | TTA | TTG | GGA | GAA | TCC | 2260 |
| Gln | Thr | Ser | Phe | Ser | Thr | Leu | Pro | Trp | Phe | His | Leu | Leu | Gly | Glu | Ser | |
| | | | | 415 | | | | | 420 | | | | | 425 | | |
| AGA | GCA | AGG | ATT | CTA | TTA | AAT | TCC | AAT | GAG | CAA | ACT | CAT | TCT | CCT | TTG | 2308 |
| Arg | Ala | Arg | Ile | Leu | Leu | Asn | Ser | Asn | Glu | Gln | Thr | His | Ser | Pro | Leu | |
| | | | 430 | | | | | 435 | | | | | 440 | | | |
| GAC | GCA | GAA | CCT | CAT | TTT | ATT | AAT | CTT | TCC | GTT | TCG | CAT | TAT | TAT | ACC | 2356 |
| Asp | Ala | Glu | Pro | His | Phe | Ile | Asn | Leu | Ser | Val | Ser | His | Tyr | Tyr | Thr | |
| | | 445 | | | | | 450 | | | | | 455 | | | | |
| GAT | AGA | GAT | ATA | ATC | AGA | AAC | TAC | GAA | TCT | TTG | TCT | TCT | TTG | GAT | CCT | 2404 |
| Asp | Arg | Asp | Ile | Ile | Arg | Asn | Tyr | Glu | Ser | Leu | Ser | Ser | Leu | Asp | Pro | |
| | 460 | | | | | 465 | | | | | 470 | | | | | |
| GAA | AAT | ATT | GGG | CTG | TAT | TTT | GAC | GCA | CTG | ACA | TAC | ATT | GCA | AAT | AGG | 2452 |
| Glu | Asn | Ile | Gly | Leu | Tyr | Phe | Asp | Ala | Leu | Thr | Tyr | Ile | Ala | Asn | Arg | |
| 475 | | | | | 480 | | | | | 485 | | | | | 490 | |
| AAG | GGG | GCA | TAT | CAA | TTG | ATT | GCT | TAC | TGT | GGA | AAA | CAG | GAC | ATT | ATA | 2500 |
| Lys | Gly | Ala | Tyr | Gln | Leu | Ile | Ala | Tyr | Cys | Gly | Lys | Gln | Asp | Ile | Ile | |
| | | | | 495 | | | | | 500 | | | | | 505 | | |
| GGC | CAA | GAA | GCT | CTA | GAA | AAT | GCT | TTG | TTA | ATG | TTT | AAA | ATT | AAC | CCT | 2548 |
| Gly | Gln | Glu | Ala | Leu | Glu | Asn | Ala | Leu | Leu | Met | Phe | Lys | Ile | Asn | Pro | |
| | | | 510 | | | | | 515 | | | | | 520 | | | |

| | | | | | | | | | | | | | | | | |
|---|---|---|---|---|---|---|---|---|---|---|---|---|---|---|---|---|
| AAA | GAG | TGT | AAC | ATC | TCC | GAA | TTA | AAT | GAG | GCG | ACT | TTG | CTA | TCT | ATT | 2596 |
| Lys | Glu | Cys 525 | Asn | Ile | Ser | Glu | Leu 530 | Asn | Glu | Ala | Thr | Leu 535 | Leu | Ser | Ile | |
| TAC | AAA | TAT | GAA | ACA | TCA | AAT | AAG | AGC | CAA | GTA | ACC | TCT | AAT | CAC | CTA | 2644 |
| Tyr | Lys 540 | Tyr | Glu | Thr | Ser | Asn | Lys 545 | Ser | Gln | Val | Thr | Ser 550 | Asn | His | Leu | |
| ACA | AAT | TTG | AAA | AAT | GCT | CTA | AGA | TTG | TTG | GCC | AAA | TAT | ACC | AAA | TCT | 2692 |
| Thr 555 | Asn | Leu | Lys | Asn | Ala | Leu 560 | Arg | Leu | Leu | Ala | Lys 565 | Tyr | Thr | Lys | Ser 570 | |
| GAC | AAA | CTA | AAA | TTT | TAC | GTC | GAT | CAT | GAG | CCC | TAC | AGA | GCT | TTA | TCC | 2740 |
| Asp | Lys | Leu | Lys | Phe 575 | Tyr | Val | Asp | His | Glu 580 | Pro | Tyr | Arg | Ala | Leu 585 | Ser | |
| CAG | GCA | TAC | GAC | ACA | CTT | TCA | ATT | GAC | GAG | TCT | GTT | GAT | GAA | GAC | ATT | 2788 |
| Gln | Ala | Tyr | Asp | Thr 590 | Leu | Ser | Ile | Asp | Glu 595 | Ser | Val | Asp | Glu | Asp 600 | Ile | |
| ATA | AAA | ACT | GCA | TAT | TCG | GTC | AAG | ATT | AAC | GAC | TCT | CCC | GGA | TTA | AAG | 2836 |
| Ile | Lys | Thr 605 | Ala | Tyr | Ser | Val | Lys 610 | Ile | Asn | Asp | Ser | Pro 615 | Gly | Leu | Lys | |
| TTG | GAT | TGT | GAT | AGA | GCA | CTT | TAC | ACC | ATT | GCT | ATC | AGT | AAA | AGA | AGC | 2884 |
| Leu | Asp | Cys 620 | Asp | Arg | Ala | Leu | Tyr 625 | Thr | Ile | Ala | Ile | Ser 630 | Lys | Arg | Ser | |
| CTT | GAT | TTG | TTC | AAT | TTT | TTA | ACA | GAG | GAA | TGC | CCA | CAG | TTT | TCC | AAC | 2932 |
| Leu 635 | Asp | Leu | Phe | Asn | Phe 640 | Leu | Thr | Glu | Glu | Cys 645 | Pro | Gln | Phe | Ser | Asn 650 | |
| TAT | TAT | GGT | CCA | GAG | AAG | CTT | CTT | CAA | GTG | AAT | GAA | AAT | GCC | TCT | GAC | 2980 |
| Tyr | Tyr | Gly | Pro | Glu 655 | Lys | Leu | Leu | Gln | Val 660 | Asn | Glu | Asn | Ala | Ser 665 | Asp | |
| GAA | ACC | ATT | TTG | AAA | ATC | TTT | AAA | CAA | AAG | TGG | TTT | GAT | GAA | AAC | GTT | 3028 |
| Glu | Thr | Ile | Leu 670 | Lys | Ile | Phe | Lys | Gln 675 | Lys | Trp | Phe | Asp | Glu 680 | Asn | Val | |
| TAT | GAG | CCT | GAC | CAA | TTT | CTT | ATT | TTG | AGG | GCA | GCA | TTG | ACC | AAA | ATC | 3076 |
| Tyr | Glu | Pro 685 | Asp | Gln | Phe | Leu | Ile 690 | Leu | Arg | Ala | Ala | Leu 695 | Thr | Lys | Ile | |
| AGT | ATA | GAA | AGA | AAT | TCA | ACT | TTA | ATC | ACC | AAC | TTC | TTA | CTA | ACT | GGT | 3124 |
| Ser | Ile | Glu 700 | Arg | Asn | Ser | Thr | Leu 705 | Ile | Thr | Asn | Phe | Leu 710 | Leu | Thr | Gly | |
| ACG | ATA | GAT | CCA | AAT | TCC | TTG | CCG | CCA | GAA | AAT | TGG | CCA | ACT | GGC | ATT | 3172 |
| Thr 715 | Ile | Asp | Pro | Asn | Ser 720 | Leu | Pro | Pro | Glu | Asn 725 | Trp | Pro | Thr | Gly | Ile 730 | |
| AAT | AAT | ATC | GGG | AAC | ACC | TGT | TAC | CTA | AAT | TCT | TTA | TTA | CAA | TAT | TAC | 3220 |
| Asn | Asn | Ile | Gly | Asn 735 | Thr | Cys | Tyr | Leu | Asn 740 | Ser | Leu | Leu | Gln | Tyr 745 | Tyr | |
| TTT | TCC | ATT | GCG | CCA | CTA | AGA | AGA | TAT | GTA | TTG | GAA | TAT | CAA | AAA | ACG | 3268 |
| Phe | Ser | Ile | Ala | Pro 750 | Leu | Arg | Arg | Tyr | Val 755 | Leu | Glu | Tyr | Gln | Lys 760 | Thr | |
| GTA | GAA | AAT | TTC | AAT | GAC | CAC | CTC | TCT | AAT | AGT | GGG | CAT | ATT | AGA | AGA | 3316 |
| Val | Glu | Asn | Phe 765 | Asn | Asp | His | Leu | Ser 770 | Asn | Ser | Gly | His | Ile 775 | Arg | Arg | |
| ATT | GGT | GGA | AGA | GAA | ATT | AGT | AGA | GGC | GAA | GTG | GAA | AGA | TCT | ATT | CAA | 3364 |
| Ile | Gly | Gly 780 | Arg | Glu | Ile | Ser | Arg 785 | Gly | Glu | Val | Glu | Arg 790 | Ser | Ile | Gln | |
| TTC | ATA | TAC | CAA | CTT | CGC | AAC | CTT | TTC | TAT | GCG | ATG | GTT | CAT | ACA | AGA | 3412 |
| Phe 795 | Ile | Tyr | Gln | Leu | Arg 800 | Asn | Leu | Phe | Tyr | Ala 805 | Met | Val | His | Thr | Arg 810 | |
| GAA | AGA | TGT | GTA | ACA | CCC | TCA | AAA | GAG | CTA | GCA | TAT | TTG | GCA | TTT | GCT | 3460 |
| Glu | Arg | Cys | Val | Thr 815 | Pro | Ser | Lys | Glu | Leu 820 | Ala | Tyr | Leu | Ala | Phe 825 | Ala | |
| CCA | AGT | AAT | GTT | GAA | GTA | GAA | TTT | GAA | GTG | GAA | GGC | AAT | AAA | GTA | GTT | 3508 |
| Pro | Ser | Asn | Val | Glu 830 | Val | Glu | Phe | Glu | Val 835 | Glu | Gly | Asn | Lys | Val 840 | Val | |

| | | | | | | | | | | | | | | | | |
|---|---|---|---|---|---|---|---|---|---|---|---|---|---|---|---|---|
| GAT | CAA | ACA | GGA | GTT | CTT | TCG | GAT | TCA | AAG | AAG | GAA | ACA | ACG | GAT | GAC | 3556 |
| Asp | Gln | Thr | Gly | Val | Leu | Ser | Asp | Ser | Lys | Lys | Glu | Thr | Thr | Asp | Asp | |
| | | 845 | | | | | 850 | | | | | 855 | | | | |
| GCA | TTT | ACT | ACA | AAA | ATA | AAG | GAT | ACA | AGC | CTG | ATT | GAT | TTA | GAA | ATG | 3604 |
| Ala | Phe | Thr | Thr | Lys | Ile | Lys | Asp | Thr | Ser | Leu | Ile | Asp | Leu | Glu | Met | |
| | | 860 | | | | 865 | | | | | 870 | | | | | |
| GAA | GAT | GGC | CTT | AAT | GGC | GAT | GTT | GGT | ACA | GAT | GCG | AAC | AGA | AAA | AAA | 3652 |
| Glu | Asp | Gly | Leu | Asn | Gly | Asp | Val | Gly | Thr | Asp | Ala | Asn | Arg | Lys | Lys | |
| 875 | | | | 880 | | | | | 885 | | | | | 890 | | |
| AAT | GAA | TCG | AAT | GAT | GCT | GAA | GTA | AGT | GAG | AAC | GAA | GAT | ACA | ACA | GGA | 3700 |
| Asn | Glu | Ser | Asn | Asp | Ala | Glu | Val | Ser | Glu | Asn | Glu | Asp | Thr | Thr | Gly | |
| | | | | 895 | | | | | 900 | | | | | 905 | | |
| TTA | ACT | TCA | CCT | ACG | CGT | GTG | GCA | AAA | ATC | AGT | TCT | GAT | CAA | TTA | GAA | 3748 |
| Leu | Thr | Ser | Pro | Thr | Arg | Val | Ala | Lys | Ile | Ser | Ser | Asp | Gln | Leu | Glu | |
| | | | 910 | | | | | 915 | | | | | 920 | | | |
| AAT | GCT | TTG | GAA | ATG | GGT | AGG | CAA | CAA | GAT | GTT | ACT | GAA | TGC | ATA | GGA | 3796 |
| Asn | Ala | Leu | Glu | Met | Gly | Arg | Gln | Gln | Asp | Val | Thr | Glu | Cys | Ile | Gly | |
| | | | | 925 | | | | | 930 | | | | | 935 | | |
| AAC | GTG | TTA | TTT | CAG | ATA | GAA | AGC | GGT | TCA | GAG | CCT | ATC | CGA | TAT | GAT | 3844 |
| Asn | Val | Leu | Phe | Gln | Ile | Glu | Ser | Gly | Ser | Glu | Pro | Ile | Arg | Tyr | Asp | |
| | | | | 940 | | | | | 945 | | | | | 950 | | |
| GAA | GAC | AAC | GAG | CAA | TAT | GAC | TTG | GTT | AAG | CAA | CTA | TTT | TAT | GGT | ACT | 3892 |
| Glu | Asp | Asn | Glu | Gln | Tyr | Asp | Leu | Val | Lys | Gln | Leu | Phe | Tyr | Gly | Thr | |
| 955 | | | | | 960 | | | | | 965 | | | | | 970 | |
| ACT | AAA | CAA | AGT | ATT | GTT | CCT | TTG | TCC | GCA | ACA | AAT | AAA | GTC | CGT | ACG | 3940 |
| Thr | Lys | Gln | Ser | Ile | Val | Pro | Leu | Ser | Ala | Thr | Asn | Lys | Val | Arg | Thr | |
| | | | | 975 | | | | | 980 | | | | | 985 | | |
| AAA | GTT | GAA | AGA | TTC | CTA | TCG | TTA | CTG | ATA | AAT | ATT | GGC | GAT | CAT | CCT | 3988 |
| Lys | Val | Glu | Arg | Phe | Leu | Ser | Leu | Leu | Ile | Asn | Ile | Gly | Asp | His | Pro | |
| | | | 990 | | | | | 995 | | | | | 1000 | | | |
| AAA | GAT | ATT | TAT | GAT | GCG | TTT | GAT | TCT | TAT | TTT | AAA | GAC | GAA | TAT | CTG | 4036 |
| Lys | Asp | Ile | Tyr | Asp | Ala | Phe | Asp | Ser | Tyr | Phe | Lys | Asp | Glu | Tyr | Leu | |
| | | | 1005 | | | | | 1010 | | | | | 1015 | | | |
| ACA | ATG | GAA | GAG | TAT | GGT | GAT | GTT | ATA | CGT | ACC | GTT | GCT | GTT | ACA | ACT | 4084 |
| Thr | Met | Glu | Glu | Tyr | Gly | Asp | Val | Ile | Arg | Thr | Val | Ala | Val | Thr | Thr | |
| | | 1020 | | | | | 1025 | | | | | 1030 | | | | |
| TTT | CCT | ACT | ATT | TTG | CAG | GTA | CAA | ATC | CAA | AGA | GTT | TAT | TAC | GAT | CGT | 4132 |
| Phe | Pro | Thr | Ile | Leu | Gln | Val | Gln | Ile | Gln | Arg | Val | Tyr | Tyr | Asp | Arg | |
| 1035 | | | | | 1040 | | | | | 1045 | | | | | 1050 | |
| GAA | AGA | TTA | ATG | CCG | TTT | AAA | TCC | ATT | GAG | CCC | TTA | CCA | TTC | AAA | GAA | 4180 |
| Glu | Arg | Leu | Met | Pro | Phe | Lys | Ser | Ile | Glu | Pro | Leu | Pro | Phe | Lys | Glu | |
| | | | | 1055 | | | | | 1060 | | | | | 1065 | | |
| GTT | ATT | TAC | ATG | GAC | AGA | TAC | GCG | GAT | ACA | GAG | AAC | CCT | TTA | TTG | TTG | 4228 |
| Val | Ile | Tyr | Met | Asp | Arg | Tyr | Ala | Asp | Thr | Glu | Asn | Pro | Leu | Leu | Leu | |
| | | | 1070 | | | | | 1075 | | | | | 1080 | | | |
| GCA | AAA | AAG | AAA | GAA | ACA | GAA | GAA | ATG | AAG | CAA | AAG | TTG | AAG | GTA | ATG | 4276 |
| Ala | Lys | Lys | Lys | Glu | Thr | Glu | Glu | Met | Lys | Gln | Lys | Leu | Lys | Val | Met | |
| | | | 1085 | | | | | 1090 | | | | | 1095 | | | |
| AAA | AAT | AGA | CAA | AGA | GAG | CTT | TTG | AGT | CGT | GAT | GAT | TCA | GGG | CTT | ACA | 4324 |
| Lys | Asn | Arg | Gln | Arg | Glu | Leu | Leu | Ser | Arg | Asp | Asp | Ser | Gly | Leu | Thr | |
| | | 1100 | | | | | 1105 | | | | | 1110 | | | | |
| AGG | AAG | GAT | GCA | TTT | TTG | GAG | AGT | ATC | AAG | CTA | TTG | GAA | TCG | GAT | ACC | 4372 |
| Arg | Lys | Asp | Ala | Phe | Leu | Glu | Ser | Ile | Lys | Leu | Leu | Glu | Ser | Asp | Thr | |
| 1115 | | | | | 1120 | | | | | 1125 | | | | | 1130 | |
| ATA | AAG | AAA | ACT | CCT | TTA | AAA | ATT | GAG | GCT | GCT | AAT | GAT | GTG | ATA | AAG | 4420 |
| Ile | Lys | Lys | Thr | Pro | Leu | Lys | Ile | Glu | Ala | Ala | Asn | Asp | Val | Ile | Lys | |
| | | | | 1135 | | | | | 1140 | | | | | 1145 | | |
| ACG | CTG | AGA | AAC | AAC | GTT | CAA | AAT | ATC | GAT | AAT | GAA | TTG | ATG | AAA | TTA | 4468 |
| Thr | Leu | Arg | Asn | Asn | Val | Gln | Asn | Ile | Asp | Asn | Glu | Leu | Met | Lys | Leu | |
| | | | | 1150 | | | | | 1155 | | | | | 1160 | | |

| | | | | | | | | | | | | | | | | |
|---|---|---|---|---|---|---|---|---|---|---|---|---|---|---|---|---|
| TAC | AAT | GAT | ATC | AAC | AGT | TTG | GAA | GAG | AAA | ATA | AGC | CAT | CAA | TTT | GAC | 4516 |
| Tyr | Asn | Asp | Ile | Asn | Ser | Leu | Glu | Glu | Lys | Ile | Ser | His | Gln | Phe | Asp | |
| | | | 1165 | | | | 1170 | | | | | 1175 | | | | |
| GAT | TTC | AAG | GAA | TAT | GGT | TAC | TCA | CTG | TTT | TCG | GTT | TTT | ATT | CAT | CGC | 4564 |
| Asp | Phe | Lys | Glu | Tyr | Gly | Tyr | Ser | Leu | Phe | Ser | Val | Phe | Ile | His | Arg | |
| | | 1180 | | | | | 1185 | | | | | 1190 | | | | |
| GGC | GAG | GCC | AGT | TAT | GGT | CAC | TAT | TGG | ATA | TAT | ATC | AAG | GAC | AGA | AAT | 4612 |
| Gly | Glu | Ala | Ser | Tyr | Gly | His | Tyr | Trp | Ile | Tyr | Ile | Lys | Asp | Arg | Asn | |
| 1195 | | | | | 1200 | | | | 1205 | | | | | 1210 | | |
| CGC | AAT | GGA | ATT | TGG | AGG | AAG | TAC | AAT | GAT | GAA | ACC | ATC | AGC | GAG | GTC | 4660 |
| Arg | Asn | Gly | Ile | Trp | Arg | Lys | Tyr | Asn | Asp | Glu | Thr | Ile | Ser | Glu | Val | |
| | | | | 1215 | | | | | 1220 | | | | | 1225 | | |
| CAG | GAA | GAG | GAG | GTC | TTC | AAT | TTC | AAT | GAG | GGT | AAC | ACT | GCA | ACT | CCA | 4708 |
| Gln | Glu | Glu | Glu | Val | Phe | Asn | Phe | Asn | Glu | Gly | Asn | Thr | Ala | Thr | Pro | |
| | | | 1230 | | | | | 1235 | | | | | 1240 | | | |
| TAT | TTC | CTA | GTA | TAT | GTC | AAA | CAA | GGA | CAA | GAA | GGT | GAT | ATT | GAG | CCA | 4756 |
| Tyr | Phe | Leu | Val | Tyr | Val | Lys | Gln | Gly | Gln | Glu | Gly | Asp | Ile | Glu | Pro | |
| | | 1245 | | | | | 1250 | | | | | 1255 | | | | |
| TTG | AAA | AGA | ATT | CTA | AAG | TAGTCTTAGT | CAATGAAGAG | TTTATGTAAA | | | | | | | | 4804 |
| Leu | Lys | Arg | Ile | Leu | Lys | | | | | | | | | | | |
| | | 1260 | | | | | | | | | | | | | | |

| | | | | | |
|---|---|---|---|---|---|
| ATGTCACTAT | TGCCATAAGT | ACCATTATTA | TGTAAAAAGC | TTTGCCATAT | TCAATGTTA | 4864 |
| GGGTGACTAT | CTGCTACGTA | AAGAAAAACG | AAAAACAAA | AAAAAAAGA | ACAAGCTCA | 4924 |
| AGAAGTGAAT | ACGAAAGCTG | AAGAAAGTCG | TTAAGTAGAT | AGGTTGCGTA | AACTAGGTG | 4984 |
| GTCCAATCAA | AGTAATCCAA | TTAGATATAC | TGGACTATAA | TTAAGATGTC | ATCTGAAAG | 5044 |
| CCACAGGATC | AACCACAGAA | GGAGCAAATC | AGCAATAACG | TCGGCGTTAC | CACCAATAG | 5104 |
| ACAAGCAATG | AGGAAACAAG | CCGCTCTCAA | GATGATAATG | TCAAGGAAGT | CAATGGAAA | 5164 |
| GATGATACTA | AAGAAGAGGA | ACAAGAAGAA | GACGCAGAAC | TAGATGATTT | ATTTGGAGA | 5224 |
| GACAATGATG | ACGATGATGA | TGATGATGTT | AAAAAATCGG | AGACTGAAAA | AAGTGATAG | 5284 |
| GATAGTGATG | AAGACGACGA | GGGAGAGAAT | ATCAACCATA | GAAGTCGTCA | TAGAGAAAG | 5344 |
| CTCGGGTTAG | ATGATGATGA | AGCAGAGGAG | CAAGCCATGT | ACACCCGAAA | ATTTTATGG | 5404 |
| GAGGATGCTA | ATAACTTTTC | TGATCTTGAT | GAGACTACTC | ACACTTTTAA | AGAGGAAAA | 5464 |
| GTAGAGCTTG | TCAGACATAT | TATTCCAAGT | AAAGCTAATG | TGAATGAAAC | GGCGTCTCA | 5524 |
| AACGAAATTT | TCTATGCTAG | AATTCCCAAC | TTTTTAACTA | TCGATCCAAT | TCCTTTCGA | 5584 |
| CCTCCAAGTT | TTGAGGCCAA | AGTAAACGAA | AGGGCAAGCA | ATTCAGCTTC | TAGGGAGGA | 5644 |
| CAACTGGACG | ACCGCCTGAT | TGATGAAAAC | ACTGTTAGAT | GGAGATACTC | TCGTGACAA | 5704 |
| GACCAACATG | TCTTTAAAGA | ATCAAATACA | CAAATAGTGC | AGTGGTCAGA | CGGTACATA | 5764 |
| TCGCTAAAAG | TTGGTGAAGA | GTGTACAGAT | ATATTGGTCA | ACGATACGAG | CAACACTTT | 5824 |
| TTGACAGTAT | CGCATGACCA | ACAAGAGTTG | ATCCAGTGTT | ACGAAGGGGG | TGAAATAAA | 5884 |
| AAGACGTTGA | TGTTTATTCC | AACTTCGACG | AATTCAAAAA | TACATCAAAA | ACTAAGTAA | 5944 |
| GCTGTTATAA | GAAGGAACCA | AAGACAAAGC | AAGGGTCCTG | GAAATACATT | GTAAGTATG | 6004 |
| ATCC | | | | | | 6008 |

(2) INFORMATION FOR SEQ ID NO:6:

(i) SEQUENCE CHARACTERISTICS:
        (A) LENGTH: 1264 amino acids
        (B) TYPE: amino acid
        (D) TOPOLOGY: linear (ii) MOLECULE TYPE: protein ( x i ) SEQUENCE DESCRIPTION: SEQ ID NO:6:

| Met | Pro | Asn | Glu | Asp | Asn | Glu | Leu | Gln | Lys | Ala | Ile | Glu | Asn | His | His |
|---|---|---|---|---|---|---|---|---|---|---|---|---|---|---|---|
| 1 | | | | 5 | | | | | 10 | | | | | 15 | |

| Asn | Gln | Leu | Leu | Asn | Gln | Asp | Lys | Glu | Asn | Ala | Asp | Arg | Asn | Gly | Ser |
|---|---|---|---|---|---|---|---|---|---|---|---|---|---|---|---|
| | | | 20 | | | | | 25 | | | | | 30 | | |

| Val | Ile | Glu | Asp | Leu | Pro | Leu | Tyr | Gly | Thr | Ser | Ile | Asn | Gln | Gln | Ser |
|---|---|---|---|---|---|---|---|---|---|---|---|---|---|---|---|
| | | 35 | | | | | 40 | | | | | 45 | | | |

| Thr | Pro | Gly | Asp | Val | Asp | Asp | Gly | Lys | His | Leu | Leu | Tyr | Pro | Asp | Ile |
|---|---|---|---|---|---|---|---|---|---|---|---|---|---|---|---|
| | 50 | | | | | 55 | | | | | 60 | | | | |

| Ala | Thr | Asn | Leu | Pro | Leu | Lys | Thr | Ser | Asp | Arg | Leu | Leu | Asp | Asp | Ile |
|---|---|---|---|---|---|---|---|---|---|---|---|---|---|---|---|
| 65 | | | | | 70 | | | | | 75 | | | | | 80 |

| Leu | Cys | Asp | Thr | Ile | Phe | Leu | Asn | Ser | Thr | Asp | Pro | Lys | Val | Met | Gln |
|---|---|---|---|---|---|---|---|---|---|---|---|---|---|---|---|
| | | | | 85 | | | | | 90 | | | | | 95 | |

| Lys | Gly | Leu | Gln | Ser | Arg | Gly | Ile | Leu | Lys | Glu | Ser | Met | Leu | Ser | Tyr |
|---|---|---|---|---|---|---|---|---|---|---|---|---|---|---|---|
| | | | 100 | | | | | 105 | | | | | 110 | | |

| Ser | Thr | Phe | Arg | Ser | Ser | Ile | Arg | Pro | Asn | Cys | Leu | Gly | Ser | Leu | Thr |
|---|---|---|---|---|---|---|---|---|---|---|---|---|---|---|---|
| | | 115 | | | | | 120 | | | | | 125 | | | |

| Asp | Gln | Val | Val | Phe | Gln | Thr | Lys | Ser | Glu | Tyr | Asp | Ser | Ile | Ser | Cys |
|---|---|---|---|---|---|---|---|---|---|---|---|---|---|---|---|
| | 130 | | | | | 135 | | | | | 140 | | | | |

| Pro | Lys | Tyr | Asn | Lys | Ile | His | Val | Phe | Gln | Ala | Val | Ile | Phe | Asn | Pro |
|---|---|---|---|---|---|---|---|---|---|---|---|---|---|---|---|
| 145 | | | | | 150 | | | | | 155 | | | | | 160 |

| Ser | Leu | Ala | Glu | Gln | Gln | Ile | Ser | Thr | Phe | Asp | Asp | Ile | Val | Lys | Ile |
|---|---|---|---|---|---|---|---|---|---|---|---|---|---|---|---|
| | | | | 165 | | | | | 170 | | | | | 175 | |

| Pro | Ile | Tyr | His | Leu | Lys | Val | Ser | Val | Lys | Val | Arg | Gln | Glu | Leu | Glu |
|---|---|---|---|---|---|---|---|---|---|---|---|---|---|---|---|
| | | | 180 | | | | | 185 | | | | | 190 | | |

| Arg | Leu | Lys | Lys | His | Val | Gly | Val | Thr | Gln | Phe | His | Ser | Leu | Asp | His |
|---|---|---|---|---|---|---|---|---|---|---|---|---|---|---|---|
| | | 195 | | | | | 200 | | | | | 205 | | | |

| Leu | His | Glu | Tyr | Asp | Arg | Val | Asp | Leu | Ser | Thr | Phe | Asp | Ser | Ser | Asp |
|---|---|---|---|---|---|---|---|---|---|---|---|---|---|---|---|
| | 210 | | | | | 215 | | | | | 220 | | | | |

| Pro | Asn | Leu | Leu | Asp | Tyr | Gly | Ile | Tyr | Val | Ser | Asp | Asp | Thr | Asn | Lys |
|---|---|---|---|---|---|---|---|---|---|---|---|---|---|---|---|
| 225 | | | | | 230 | | | | | 235 | | | | | 240 |

| Leu | Ile | Leu | Ile | Glu | Ile | Phe | Lys | Pro | Glu | Phe | Asn | Ser | Pro | Glu | Glu |
|---|---|---|---|---|---|---|---|---|---|---|---|---|---|---|---|
| | | | | 245 | | | | | 250 | | | | | 255 | |

| His | Glu | Ser | Phe | Thr | Ala | Asp | Ala | Ile | Lys | Lys | Arg | Tyr | Asn | Ala | Met |
|---|---|---|---|---|---|---|---|---|---|---|---|---|---|---|---|
| | | | 260 | | | | | 265 | | | | | 270 | | |

| Cys | Val | Lys | Asn | Glu | Ser | Leu | Asp | Lys | Ser | Glu | Thr | Pro | Ser | Gln | Val |
|---|---|---|---|---|---|---|---|---|---|---|---|---|---|---|---|
| | | 275 | | | | | 280 | | | | | 285 | | | |

| Asp | Cys | Phe | Tyr | Thr | Leu | Phe | Lys | Ile | Phe | Lys | Gly | Pro | Leu | Thr | Arg |
|---|---|---|---|---|---|---|---|---|---|---|---|---|---|---|---|
| | 290 | | | | | 295 | | | | | 300 | | | | |

| Lys | Ser | Lys | Ala | Glu | Pro | Thr | Lys | Thr | Ile | Asp | Ser | Gly | Asn | Leu | Ala |
|---|---|---|---|---|---|---|---|---|---|---|---|---|---|---|---|
| 305 | | | | | 310 | | | | | 315 | | | | | 320 |

| Leu | Asn | Thr | His | Leu | Asn | Pro | Glu | Trp | Leu | Thr | Ser | Lys | Tyr | Gly | Phe |
|---|---|---|---|---|---|---|---|---|---|---|---|---|---|---|---|
| | | | | 325 | | | | | 330 | | | | | 335 | |

| Gln | Ala | Ser | Ser | Glu | Ile | Asp | Glu | Glu | Thr | Asn | Glu | Ile | Phe | Thr | Glu |
|---|---|---|---|---|---|---|---|---|---|---|---|---|---|---|---|
| | | | 340 | | | | | 345 | | | | | 350 | | |

| Tyr | Val | Pro | Pro | Asp | Met | Val | Asp | Tyr | Val | Asn | Asp | Leu | Glu | Thr | Arg |
|---|---|---|---|---|---|---|---|---|---|---|---|---|---|---|---|
| | | 355 | | | | | 360 | | | | | 365 | | | |

| Lys | Ile | Arg | Glu | Ser | Phe | Val | Arg | Lys | Cys | Leu | Gln | Leu | Ile | Phe | Trp |
|---|---|---|---|---|---|---|---|---|---|---|---|---|---|---|---|
| | 370 | | | | | 375 | | | | | 380 | | | | |

| Gly | Gln | Leu | Ser | Thr | Ser | Leu | Leu | Ala | Pro | Asn | Ser | Pro | Leu | Lys | Asn |
|---|---|---|---|---|---|---|---|---|---|---|---|---|---|---|---|
| 385 | | | | | 390 | | | | | 395 | | | | | 400 |

| Thr | Lys | Ser | Val | Lys | Gly | Met | Ser | Ser | Leu | Gln | Thr | Ser | Phe | Ser | Thr |
|---|---|---|---|---|---|---|---|---|---|---|---|---|---|---|---|
| | | | | 405 | | | | | 410 | | | | | 415 | |

| | | | | | | | | | | | | | | |
|---|---|---|---|---|---|---|---|---|---|---|---|---|---|---|
| Leu | Pro | Trp | Phe 420 | His | Leu | Leu | Gly | Glu 425 | Ser | Arg | Ala | Arg 430 | Ile | Leu | Leu |
| Asn | Ser | Asn 435 | Glu | Gln | Thr | His | Ser 440 | Pro | Leu | Asp | Ala | Glu 445 | Pro | His | Phe |
| Ile | Asn 450 | Leu | Ser | Val | Ser | His 455 | Tyr | Tyr | Thr | Asp | Arg 460 | Asp | Ile | Ile | Arg |
| Asn 465 | Tyr | Glu | Ser | Leu | Ser 470 | Ser | Leu | Asp | Pro | Glu 475 | Asn | Ile | Gly | Leu | Tyr 480 |
| Phe | Asp | Ala | Leu | Thr 485 | Tyr | Ile | Ala | Asn | Arg 490 | Lys | Gly | Ala | Tyr | Gln 495 | Leu |
| Ile | Ala | Tyr | Cys 500 | Gly | Lys | Gln | Asp | Ile 505 | Ile | Gly | Gln | Glu | Ala 510 | Leu | Glu |
| Asn | Ala | Leu 515 | Leu | Met | Phe | Lys | Ile 520 | Asn | Pro | Lys | Glu | Cys 525 | Asn | Ile | Ser |
| Glu | Leu 530 | Asn | Glu | Ala | Thr | Leu 535 | Leu | Ser | Ile | Tyr | Lys 540 | Tyr | Glu | Thr | Ser |
| Asn 545 | Lys | Ser | Gln | Val | Thr 550 | Ser | Asn | His | Leu | Thr 555 | Asn | Leu | Lys | Asn | Ala 560 |
| Leu | Arg | Leu | Leu | Ala 565 | Lys | Tyr | Thr | Lys | Ser 570 | Asp | Lys | Leu | Lys | Phe 575 | Tyr |
| Val | Asp | His | Glu 580 | Pro | Tyr | Arg | Ala | Leu 585 | Ser | Gln | Ala | Tyr | Asp 590 | Thr | Leu |
| Ser | Ile | Asp 595 | Glu | Ser | Val | Asp | Glu 600 | Asp | Ile | Ile | Lys | Thr 605 | Ala | Tyr | Ser |
| Val | Lys 610 | Ile | Asn | Asp | Ser | Pro 615 | Gly | Leu | Lys | Leu | Asp 620 | Cys | Asp | Arg | Ala |
| Leu 625 | Tyr | Thr | Ile | Ala | Ile 630 | Ser | Lys | Arg | Ser | Leu 635 | Asp | Leu | Phe | Asn | Phe 640 |
| Leu | Thr | Glu | Glu | Cys 645 | Pro | Gln | Phe | Ser | Asn 650 | Tyr | Tyr | Gly | Pro | Glu 655 | Lys |
| Leu | Leu | Gln | Val 660 | Asn | Glu | Asn | Ala | Ser 665 | Asp | Glu | Thr | Ile | Leu 670 | Lys | Ile |
| Phe | Lys | Gln 675 | Lys | Trp | Phe | Asp | Glu 680 | Asn | Val | Tyr | Glu | Pro 685 | Asp | Gln | Phe |
| Leu | Ile 690 | Leu | Arg | Ala | Ala | Leu 695 | Thr | Lys | Ile | Ser | Ile 700 | Glu | Arg | Asn | Ser |
| Thr 705 | Leu | Ile | Thr | Asn | Phe 710 | Leu | Leu | Thr | Gly | Thr 715 | Ile | Asp | Pro | Asn | Ser 720 |
| Leu | Pro | Pro | Glu | Asn 725 | Trp | Pro | Thr | Gly | Ile 730 | Asn | Asn | Ile | Gly | Asn 735 | Thr |
| Cys | Tyr | Leu | Asn 740 | Ser | Leu | Leu | Gln | Tyr 745 | Tyr | Phe | Ser | Ile | Ala 750 | Pro | Leu |
| Arg | Arg | Tyr 755 | Val | Leu | Glu | Tyr | Gln 760 | Lys | Thr | Val | Glu | Asn 765 | Phe | Asn | Asp |
| His | Leu 770 | Ser | Asn | Ser | Gly | His 775 | Ile | Arg | Arg | Ile | Gly 780 | Gly | Arg | Glu | Ile |
| Ser 785 | Arg | Gly | Glu | Val | Glu 790 | Arg | Ser | Ile | Gln | Phe 795 | Ile | Tyr | Gln | Leu | Arg 800 |
| Asn | Leu | Phe | Tyr | Ala 805 | Met | Val | His | Thr | Arg 810 | Glu | Arg | Cys | Val | Thr 815 | Pro |
| Ser | Lys | Glu | Leu 820 | Ala | Tyr | Leu | Ala | Phe 825 | Ala | Pro | Ser | Asn | Val 830 | Glu | Val |
| Glu | Phe | Glu 835 | Val | Glu | Gly | Asn | Lys 840 | Val | Val | Asp | Gln | Thr 845 | Gly | Val | Leu |

```
Ser Asp Ser Lys Lys Glu Thr Thr Asp Asp Ala Phe Thr Thr Lys Ile
850                 855                 860
Lys Asp Thr Ser Leu Ile Asp Leu Glu Met Glu Asp Gly Leu Asn Gly
865                 870                 875                 880
Asp Val Gly Thr Asp Ala Asn Arg Lys Lys Asn Glu Ser Asn Asp Ala
            885                 890                 895
Glu Val Ser Glu Asn Glu Asp Thr Thr Gly Leu Thr Ser Pro Thr Arg
            900                 905                 910
Val Ala Lys Ile Ser Ser Asp Gln Leu Glu Asn Ala Leu Glu Met Gly
        915                 920                 925
Arg Gln Gln Asp Val Thr Glu Cys Ile Gly Asn Val Leu Phe Gln Ile
930                 935                 940
Glu Ser Gly Ser Glu Pro Ile Arg Tyr Asp Glu Asp Asn Glu Gln Tyr
945                 950                 955                 960
Asp Leu Val Lys Gln Leu Phe Tyr Gly Thr Thr Lys Gln Ser Ile Val
            965                 970                 975
Pro Leu Ser Ala Thr Asn Lys Val Arg Thr Lys Val Glu Arg Phe Leu
            980                 985                 990
Ser Leu Leu Ile Asn Ile Gly Asp His Pro Lys Asp Ile Tyr Asp Ala
        995                 1000                1005
Phe Asp Ser Tyr Phe Lys Asp Glu Tyr Leu Thr Met Glu Glu Tyr Gly
1010                1015                1020
Asp Val Ile Arg Thr Val Ala Val Thr Thr Phe Pro Thr Ile Leu Gln
1025                1030                1035                1040
Val Gln Ile Gln Arg Val Tyr Tyr Asp Arg Glu Arg Leu Met Pro Phe
            1045                1050                1055
Lys Ser Ile Glu Pro Leu Pro Phe Lys Glu Val Ile Tyr Met Asp Arg
            1060                1065                1070
Tyr Ala Asp Thr Glu Asn Pro Leu Leu Leu Ala Lys Lys Lys Glu Thr
            1075                1080                1085
Glu Glu Met Lys Gln Lys Leu Lys Val Met Lys Asn Arg Gln Arg Glu
        1090                1095                1100
Leu Leu Ser Arg Asp Asp Ser Gly Leu Thr Arg Lys Asp Ala Phe Leu
1105                1110                1115                1120
Glu Ser Ile Lys Leu Leu Glu Ser Asp Thr Ile Lys Lys Thr Pro Leu
            1125                1130                1135
Lys Ile Glu Ala Ala Asn Asp Val Ile Lys Thr Leu Arg Asn Asn Val
            1140                1145                1150
Gln Asn Ile Asp Asn Glu Leu Met Lys Leu Tyr Asn Asp Ile Asn Ser
        1155                1160                1165
Leu Glu Glu Lys Ile Ser His Gln Phe Asp Asp Phe Lys Glu Tyr Gly
        1170                1175                1180
Tyr Ser Leu Phe Ser Val Phe Ile His Arg Gly Glu Ala Ser Tyr Gly
1185                1190                1195                1200
His Tyr Trp Ile Tyr Ile Lys Asp Arg Asn Arg Asn Gly Ile Trp Arg
            1205                1210                1215
Lys Tyr Asn Asp Glu Thr Ile Ser Glu Val Gln Glu Glu Glu Val Phe
            1220                1225                1230
Asn Phe Asn Glu Gly Asn Thr Ala Thr Pro Tyr Phe Leu Val Tyr Val
        1235                1240                1245
Lys Gln Gly Gln Glu Gly Asp Ile Glu Pro Leu Lys Arg Ile Leu Lys
        1250                1255                1260
```

( 2 ) INFORMATION FOR SEQ ID NO:7:

( i ) SEQUENCE CHARACTERISTICS:
        ( A ) LENGTH: 4887 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1278..4013

( x i ) SEQUENCE DESCRIPTION: SEQ ID NO:7:

```
GCATGCTGAA CATCCTTCTG CAAACAACCT TGCCACATAA CGGGTATACC AGGCAGGCGT      60

TCATCATCAC GCCAACATAT TTCTTGATCA ACAATTGCTT CACAGATGCG GGATTCAAGG     120

GGAAAATGAC CGCCATCAAC GAGCAGGGCC ACGACTCGAT TGATTTCGAG TCGTTGATTT     180

CTGCCCTTGA GCAGCACGAG GCGGAGCCGC AGCCCCATAG TACCACAGAG ATGATTCAGG     240

GGCCAAAGTT GACCAAGAAG GTCTACAGGT ACGTTATGTA CTGCATCCCG ACGTTTGCAA     300

ACCCATCGGG AAACACATAC TCGCTTGAGA CCAGACGCAG ACTTATCGAC ATCGCTCGGA     360

AGTACGACAT GCTGATAATC ACTGATGACG TGTACGATAT TCTAGATTAC ACGACGCCCT     420

CAGATGAGCT GCCCTCTCCG CCCCTAAGGA TGGTGCACAT AGACAGAAGT ACAGCGCCCT     480

CCGGTGAGGA CTCGTTCGGG AATACAGTGT CCAACGCAAC TTTCTCCAAG CTGATCGCCC     540

CTGGGCTCAG ATTTGGATAC CATGAGTCAA TCAACGCGAA TCTCGCCAGA CAGCTATCTA     600

AAGGTGGTGC AAACGTCTCT GGCGGAACTC CCTCACAACT GAACTCCATG ATCGTGGGTG     660

AGATGCTGCG TAGTGGTGCC GCCCAGAGAT GCATTGCACA TCTGAGATCC GTATACTCCG     720

AGAGGGCCAC TGTCTTGACC TCGGCGCTTA AGAAATACAT GCCCCATGGA ACCGAGATTA     780

TGCCATTGAA GGGCGGCTAT TTTACTTGGA TCACTCTCCC ACCAGCGTAC AATGCCATGG     840

AGATATCCAC TATTCTTGCC AAGAAATTTA ATGTCATCCT TGCCGACGGC TCCAATTTCG     900

AGGTCATCGG CGATGAGAAA AACTGGGGTC AGTCATGCTT TAGGCTTTCT ATTAGTTTCT     960

TAGAAGTTGA TGATATCGAC AGGGGCATTG AGCTGTTTGG AGCTGTTTGC AAATCTCAT    1020

CGATCACCAA TAACATAACT ATGTAGAAGG AATACGTATA TAGGTGAACG GTAATAAGA    1080

GGTAATTTTT CTACGGGCAA AGGCAAGGAA GAAAAGAAA AGAAGGAAA AAAATATAA     1140

GTGATAAAAC AAACAAGCAG CGAAAAAGCG AAAGGGAAGA GAAGTGTTCT AGAGAAGAA    1200

GTCATTTTAA TAGTAAGTCA GACTCGTCTG CTACCATCAT CCAGGTACCG CTTTCCTTT    1260

CATCATCATT AAAAAAA ATG AAC ATG CAA GAC GCT AAC AAA GAA GAG TCG     1310
                    Met Asn Met Gln Asp Ala Asn Lys Glu Glu Ser
                     1               5                  10

TAC TCG ATG TAC CCG AAA ACC TCT TCT CCA CCA CCA CCT ACG CCA ACC     1358
Tyr Ser Met Tyr Pro Lys Thr Ser Ser Pro Pro Pro Pro Thr Pro Thr
             15                  20                  25

AAT ATG CAG ATT CCT ATT TAT CAA GCG CCT TTG CAG ATG TAC GGC TAC     1406
Asn Met Gln Ile Pro Ile Tyr Gln Ala Pro Leu Gln Met Tyr Gly Tyr
         30                  35                  40

ACT CAG GCC CCA TAT CTA TAC CCC ACA CAA ATA CCT GCC TAT TCG TTT     1454
Thr Gln Ala Pro Tyr Leu Tyr Pro Thr Gln Ile Pro Ala Tyr Ser Phe
     45                  50                  55

AAT ATG GTC AAC CAA AAC CAG CCA ATC TAC CAT CAA AGT GGC AGC CCA     1502
Asn Met Val Asn Gln Asn Gln Pro Ile Tyr His Gln Ser Gly Ser Pro
 60                  65                  70                  75

CAT CAC TTG CCT CCG CAA AAC AAT ATT AAC GGC GGA AGC ACT ACC AAT     1550
His His Leu Pro Pro Gln Asn Asn Ile Asn Gly Gly Ser Thr Thr Asn
             80                  85                  90
```

| | | | | | | | | | | | | | | | | |
|---|---|---|---|---|---|---|---|---|---|---|---|---|---|---|---|---|
| AAC | AAC | AAC | ATT | AAC | AAG | AAG | AAG | TGG | CAC | TCT | AAT | GGC | ATT | ACC | AAT | 1598 |
| Asn | Asn | Asn | Ile | Asn | Lys | Lys | Lys | Trp | His | Ser | Asn | Gly | Ile | Thr | Asn | |
| | | | 95 | | | | 100 | | | | | 105 | | | | |
| AAC | AAT | GGA | AGC | AGC | GGT | AAT | CAA | GGC | GCC | AAC | TCT | AGC | GGT | AGC | GGC | 1646 |
| Asn | Asn | Gly | Ser | Ser | Gly | Asn | Gln | Gly | Ala | Asn | Ser | Ser | Gly | Ser | Gly | |
| | | 110 | | | | 115 | | | | | 120 | | | | | |
| ATG | AGC | TAC | AAC | AAA | TCC | CAC | ACC | TAC | CAT | CAC | AAT | TAC | TCT | AAC | AAT | 1694 |
| Met | Ser | Tyr | Asn | Lys | Ser | His | Thr | Tyr | His | His | Asn | Tyr | Ser | Asn | Asn | |
| | 125 | | | | 130 | | | | | 135 | | | | | | |
| CAT | ATC | CCC | ATG | ATG | GCC | TCT | CCA | AAC | AGT | GGC | AGC | AAT | GCG | GGC | ATG | 1742 |
| His | Ile | Pro | Met | Met | Ala | Ser | Pro | Asn | Ser | Gly | Ser | Asn | Ala | Gly | Met | |
| 140 | | | | 145 | | | | | 150 | | | | | 155 | | |
| AAA | AAA | CAG | ACC | AAC | TCT | TCC | AAC | GGC | AAC | GGT | TCT | TCG | GCT | ACT | TCA | 1790 |
| Lys | Lys | Gln | Thr | Asn | Ser | Ser | Asn | Gly | Asn | Gly | Ser | Ser | Ala | Thr | Ser | |
| | | | | 160 | | | | | 165 | | | | | 170 | | |
| CCA | TCG | TAC | TCT | TCC | TAC | AAC | TCT | TCT | TCA | CAG | TAT | GAT | TTA | TAC | AAG | 1838 |
| Pro | Ser | Tyr | Ser | Ser | Tyr | Asn | Ser | Ser | Ser | Gln | Tyr | Asp | Leu | Tyr | Lys | |
| | | | 175 | | | | | 180 | | | | | 185 | | | |
| TTT | GAT | GTC | ACT | AAA | TTA | AAG | AAT | CTC | AAG | GAA | AAT | TCA | TCA | AAC | TTG | 1886 |
| Phe | Asp | Val | Thr | Lys | Leu | Lys | Asn | Leu | Lys | Glu | Asn | Ser | Ser | Asn | Leu | |
| | | | 190 | | | | | 195 | | | | | 200 | | | |
| ATT | CAA | TTG | CCA | CTG | TTC | ATA | AAC | ACT | ACG | GAA | GCA | GAA | TTT | GCT | GCG | 1934 |
| Ile | Gln | Leu | Pro | Leu | Phe | Ile | Asn | Thr | Thr | Glu | Ala | Glu | Phe | Ala | Ala | |
| | 205 | | | | | 210 | | | | | 215 | | | | | |
| GCA | AGT | GTC | CAA | AGG | TAC | GAA | TTA | AAC | ATG | AAG | GCT | TTG | AAC | CTA | AAC | 1982 |
| Ala | Ser | Val | Gln | Arg | Tyr | Glu | Leu | Asn | Met | Lys | Ala | Leu | Asn | Leu | Asn | |
| 220 | | | | | 225 | | | | | 230 | | | | | 235 | |
| TCT | GAA | AGC | TTA | GAG | AAC | TCA | TCT | GTA | GAA | AAG | AGC | TCT | GCC | CAT | CAT | 2030 |
| Ser | Glu | Ser | Leu | Glu | Asn | Ser | Ser | Val | Glu | Lys | Ser | Ser | Ala | His | His | |
| | | | | 240 | | | | | 245 | | | | | 250 | | |
| CAC | ACA | AAA | AGC | CAT | AGT | ATA | CCA | AAG | CAT | AAT | GAG | GAA | GTA | AAG | ACA | 2078 |
| His | Thr | Lys | Ser | His | Ser | Ile | Pro | Lys | His | Asn | Glu | Glu | Val | Lys | Thr | |
| | | | 255 | | | | | 260 | | | | | 265 | | | |
| GAA | ACA | CAT | GGG | GAA | GAA | GAA | GAT | GCT | CAT | GAT | AAA | AAA | CCA | CAT | GCG | 2126 |
| Glu | Thr | His | Gly | Glu | Glu | Glu | Asp | Ala | His | Asp | Lys | Lys | Pro | His | Ala | |
| | | 270 | | | | | 275 | | | | | 280 | | | | |
| AGC | AAA | GAT | GCG | CAC | GAG | CTT | AAA | AAG | AAA | ACT | GAA | GTA | AAG | AAA | GAG | 2174 |
| Ser | Lys | Asp | Ala | His | Glu | Leu | Lys | Lys | Lys | Thr | Glu | Val | Lys | Lys | Glu | |
| | 285 | | | | | 290 | | | | | 295 | | | | | |
| GAT | GCT | AAG | CAA | GAC | CGT | AAC | GAA | AAA | GTT | ATA | CAG | GAA | CCT | CAA | GCT | 2222 |
| Asp | Ala | Lys | Gln | Asp | Arg | Asn | Glu | Lys | Val | Ile | Gln | Glu | Pro | Gln | Ala | |
| 300 | | | | | 305 | | | | | 310 | | | | | 315 | |
| ACT | GTT | TTA | CCT | GTA | GTG | GAT | AAG | AAG | GAA | CCA | GAG | GAA | TCT | GTT | GAA | 2270 |
| Thr | Val | Leu | Pro | Val | Val | Asp | Lys | Lys | Glu | Pro | Glu | Glu | Ser | Val | Glu | |
| | | | | 320 | | | | | 325 | | | | | 330 | | |
| GAA | AAT | ACT | TCC | AAG | ACA | TCT | TCA | CCT | TCA | CCA | TCT | CCT | CCA | GCA | GCA | 2318 |
| Glu | Asn | Thr | Ser | Lys | Thr | Ser | Ser | Pro | Ser | Pro | Ser | Pro | Pro | Ala | Ala | |
| | | | 335 | | | | | 340 | | | | | 345 | | | |
| AAA | TCC | TGG | TCC | GCC | ATA | GCA | TCA | GAT | GCG | ATT | AAA | AGT | AGA | CAA | GCT | 2366 |
| Lys | Ser | Trp | Ser | Ala | Ile | Ala | Ser | Asp | Ala | Ile | Lys | Ser | Arg | Gln | Ala | |
| | | 350 | | | | | 355 | | | | | 360 | | | | |
| AGT | AAC | AAA | ACA | GTC | TCC | GGA | TCG | ATG | GTC | ACT | AAA | ACA | CCA | ATT | TCT | 2414 |
| Ser | Asn | Lys | Thr | Val | Ser | Gly | Ser | Met | Val | Thr | Lys | Thr | Pro | Ile | Ser | |
| | 365 | | | | | 370 | | | | | 375 | | | | | |
| GGT | ACG | ACC | GCA | GGC | GTT | TCA | TCA | ACA | AAC | ATG | GCT | GCG | GCG | ACT | ATA | 2462 |
| Gly | Thr | Thr | Ala | Gly | Val | Ser | Ser | Thr | Asn | Met | Ala | Ala | Ala | Thr | Ile | |
| 380 | | | | 385 | | | | | 390 | | | | | 395 | | |
| GGT | AAA | TCC | AGC | TCT | CCC | CTG | TTG | TCC | AAG | CAG | CCT | CAG | AAA | AAG | GAT | 2510 |
| Gly | Lys | Ser | Ser | Ser | Pro | Leu | Leu | Ser | Lys | Gln | Pro | Gln | Lys | Lys | Asp | |
| | | | 400 | | | | | 405 | | | | | 410 | | | |

| | | | | | | | | | | | | | | | | |
|---|---|---|---|---|---|---|---|---|---|---|---|---|---|---|---|---|
| AAA | AAA | TAC | GTT | CCA | CCT | TCT | ACA | AAG | GGT | ATT | GAG | CCA | CTG | GGT | TCG | 2558 |
| Lys | Lys | Tyr | Val 415 | Pro | Pro | Ser | Thr | Lys 420 | Gly | Ile | Glu | Pro 425 | Leu | Gly | Ser | |
| ATT | GCG | TTA | AGA | ATG | TGT | TTT | GAT | CCC | GAT | TTC | ATT | AGT | TAC | GTT | TTA | 2606 |
| Ile | Ala | Leu | Arg 430 | Met | Cys | Phe | Asp | Pro 435 | Asp | Phe | Ile | Ser 440 | Tyr | Val | Leu | |
| CGG | AAT | AAA | GAT | GTT | GAA | AAC | AAA | ATA | CCA | GTC | CAT | TCC | ATT | ATT | CCA | 2654 |
| Arg | Asn 445 | Lys | Asp | Val | Glu | Asn 450 | Lys | Ile | Pro | Val | His 455 | Ser | Ile | Ile | Pro | |
| AGA | GGC | ATA | ATT | AAC | AGA | GCC | AAC | ATT | TGT | TTT | ATG | AGT | TCT | GTG | TTA | 2702 |
| Arg 460 | Gly | Ile | Ile | Asn | Arg 465 | Ala | Asn | Ile | Cys | Phe 470 | Met | Ser | Ser | Val | Leu 475 | |
| CAA | GTG | TTA | CTC | TAC | TGT | AAG | CCA | TTT | ATT | GAT | GTA | ATT | AAC | GTT | CTC | 2750 |
| Gln | Val | Leu | Leu | Tyr 480 | Cys | Lys | Pro | Phe | Ile 485 | Asp | Val | Ile | Asn | Val 490 | Leu | |
| AGT | ACA | CGG | AAT | ACC | AAT | TCA | AGA | GTC | GGC | ACA | TCA | TCC | TGT | AAA | TTA | 2798 |
| Ser | Thr | Arg | Asn 495 | Thr | Asn | Ser | Arg | Val 500 | Gly | Thr | Ser | Ser 505 | Cys | Lys | Leu | |
| TTA | GAT | GCT | TGT | TTG | ACT | ATG | TAT | AAG | CAA | TTC | GAT | AAG | GAA | ACC | TAT | 2846 |
| Leu | Asp | Ala | Cys 510 | Leu | Thr | Met | Tyr | Lys 515 | Gln | Phe | Asp | Lys 520 | Glu | Thr | Tyr | |
| GAG | AAA | AAA | TTC | CTA | GAG | AAT | GCT | GAT | GAT | GCT | GAA | AAA | ACC | ACG | GAA | 2894 |
| Glu | Lys 525 | Lys | Phe | Leu | Glu | Asn 530 | Ala | Asp | Asp | Ala | Glu 535 | Lys | Thr | Thr | Glu | |
| AGT | GAT | GCA | AAA | AAA | TCA | TCA | AAA | TCC | AAG | AGT | TTC | CAA | CAC | TGC | GCC | 2942 |
| Ser 540 | Asp | Ala | Lys | Lys | Ser 545 | Ser | Lys | Ser | Lys | Ser 550 | Phe | Gln | His | Cys | Ala 555 | |
| ACT | GCC | GAT | GCT | GTC | AAA | CCT | GAC | GAA | TTT | TAC | AAA | ACT | TTG | TCT | ACT | 2990 |
| Thr | Ala | Asp | Ala | Val 560 | Lys | Pro | Asp | Glu | Phe 565 | Tyr | Lys | Thr | Leu | Ser 570 | Thr | |
| ATA | CCG | AAG | TTC | AAA | GAC | TTG | CAA | TGG | GGC | CAT | CAG | GAA | GAC | GCA | GAA | 3038 |
| Ile | Pro | Lys | Phe 575 | Lys | Asp | Leu | Gln | Trp 580 | Gly | His | Gln | Glu | Asp 585 | Ala | Glu | |
| GAA | TTT | TTG | ACC | CAC | TTA | TTG | GAC | CAA | TTA | CAC | GAG | GAA | TTA | ATT | TCT | 3086 |
| Glu | Phe | Leu | Thr 590 | His | Leu | Leu | Asp | Gln 595 | Leu | His | Glu | Glu 600 | Leu | Ile | Ser | |
| GCA | ATT | GAT | GGC | TTA | ACC | GAT | AAT | GAA | ATT | CAA | AAT | ATG | CTG | CAA | AGT | 3134 |
| Ala | Ile 605 | Asp | Gly | Leu | Thr | Asp 610 | Asn | Glu | Ile | Gln | Asn 615 | Met | Leu | Gln | Ser | |
| ATT | AAT | GAT | GAA | CAA | TTG | AAA | GTT | TTC | TTT | ATT | AGA | AAT | TTG | TCA | CGT | 3182 |
| Ile | Asn | Asp | Glu 620 | Gln | Leu | Lys | Val | Phe 625 | Phe | Ile | Arg | Asn | Leu 630 | Ser | Arg 635 | |
| TAT | GGA | AAA | GCA | GAG | TTT | ATC | AAA | AAT | GCT | AGT | CCT | AGA | CTG | AAG | GAG | 3230 |
| Tyr | Gly | Lys | Ala | Glu 640 | Phe | Ile | Lys | Asn | Ala 645 | Ser | Pro | Arg | Leu | Lys 650 | Glu | |
| TTG | ATA | GAA | AAA | TAT | GGC | GTG | ATC | AAT | GAT | GAC | TCT | ACC | GAA | GAA | AAT | 3278 |
| Leu | Ile | Glu | Lys 655 | Tyr | Gly | Val | Ile | Asn 640 | Asp | Asp | Ser | Thr 665 | Glu | Glu | Asn | |
| GGT | TGG | CAT | GAA | GTG | AGC | GGA | TCT | AGC | AAA | AGA | GGC | AAG | AAA | ACT | AAG | 3326 |
| Gly | Trp | His | Glu 670 | Val | Ser | Gly | Ser 675 | Ser | Lys | Arg | Gly | Lys 680 | Lys | Thr | Lys | |
| ACC | GCT | GCC | AAG | AGG | ACT | GTC | GAG | ATT | GTT | CCA | TCA | CCA | ATC | TCC | AAA | 3374 |
| Thr | Ala | Ala 685 | Lys | Arg | Thr | Val | Glu 690 | Ile | Val | Pro | Ser | Pro 695 | Ile | Ser | Lys | |
| CTT | TTC | GGT | GGC | CAG | TTC | AGA | TCT | GTG | TTA | GAT | ATA | CCG | AAC | AAT | AAG | 3422 |
| Leu | Phe | Gly 700 | Gly | Gln | Phe | Arg | Ser 705 | Val | Leu | Asp | Ile | Pro 710 | Asn | Asn | Lys 715 | |
| GAA | TCT | CAA | TCG | ATT | ACA | CTC | GAT | CCG | TTC | CAA | ACA | ATT | CAA | TTG | GAC | 3470 |
| Glu | Ser | Gln | Ser | Ile 720 | Thr | Leu | Asp | Pro | Phe 725 | Gln | Thr | Ile | Gln | Leu 730 | Asp | |

| | | | | | | | | | | | | | | | | |
|---|---|---|---|---|---|---|---|---|---|---|---|---|---|---|---|---|
| ATT | TCA | GAT | GCT | GGT | GTG | AAT | GAT | CTA | GAA | ACT | GCA | TTC | AAA | AAA | TTT | 3518 |
| Ile | Ser | Asp | Ala | Gly | Val | Asn | Asp | Leu | Glu | Thr | Ala | Phe | Lys | Lys | Phe | |
| | | | 735 | | | | 740 | | | | | | 745 | | | |
| AGT | GAA | TAC | GAA | TTG | CTA | CCC | TTT | AAG | TCC | TCG | TCA | GGG | AAT | GAT | GTC | 3566 |
| Ser | Glu | Tyr | Glu | Leu | Leu | Pro | Phe | Lys | Ser | Ser | Ser | Gly | Asn | Asp | Val | |
| | | 750 | | | | | 755 | | | | | 760 | | | | |
| GAG | GCC | AAG | AAG | CAG | ACT | TTT | ATT | GAT | AAA | TTG | CCG | CAA | GTT | CTT | TTA | 3614 |
| Glu | Ala | Lys | Lys | Gln | Thr | Phe | Ile | Asp | Lys | Leu | Pro | Gln | Val | Leu | Leu | |
| | 765 | | | | | 770 | | | | | 775 | | | | | |
| ATC | CAA | TTC | AAA | AGA | TTC | TCA | TTC | ATA | AAT | AAT | GTG | AAC | AAA | GAC | AAC | 3662 |
| Ile | Gln | Phe | Lys | Arg | Phe | Ser | Phe | Ile | Asn | Asn | Val | Asn | Lys | Asp | Asn | |
| 780 | | | | | 785 | | | | | 790 | | | | | 795 | |
| GCA | ATG | ACG | AAC | TAT | AAC | GCG | TAC | AAT | GGA | CGT | ATT | GAG | AAG | ATC | AGG | 3710 |
| Ala | Met | Thr | Asn | Tyr | Asn | Ala | Tyr | Asn | Gly | Arg | Ile | Glu | Lys | Ile | Arg | |
| | | | | 800 | | | | | 805 | | | | | 810 | | |
| AAA | AAA | ATT | AAA | TAT | GGT | CAC | GAG | TTA | ATC | ATA | CCT | GAA | GAA | TCA | ATG | 3758 |
| Lys | Lys | Ile | Lys | Tyr | Gly | His | Glu | Leu | Ile | Ile | Pro | Glu | Glu | Ser | Met | |
| | | | 815 | | | | | 820 | | | | | 825 | | | |
| TCT | TCC | ATA | ACA | TTG | AAA | AAC | AAC | ACC | TCA | GGG | ATT | GAT | GAT | AGA | AGA | 3806 |
| Ser | Ser | Ile | Thr | Leu | Lys | Asn | Asn | Thr | Ser | Gly | Ile | Asp | Asp | Arg | Arg | |
| | | 830 | | | | | 835 | | | | | 840 | | | | |
| TAT | AAG | CTA | ACC | GGA | GTT | ATA | TAC | CAT | CAT | GGG | GTA | AGT | TCC | GAT | GGC | 3854 |
| Tyr | Lys | Leu | Thr | Gly | Val | Ile | Tyr | His | His | Gly | Val | Ser | Ser | Asp | Gly | |
| | 845 | | | | | 850 | | | | | 855 | | | | | |
| GGT | CAT | TAC | ACA | GCG | GAT | GTT | TAT | CAT | AGC | GAG | CAC | AAC | AAA | TGG | TAT | 3902 |
| Gly | His | Tyr | Thr | Ala | Asp | Val | Tyr | His | Ser | Glu | His | Asn | Lys | Trp | Tyr | |
| 860 | | | | | 865 | | | | | 870 | | | | | 875 | |
| AGA | ATA | GAT | GAT | GTA | AAT | ATT | ACC | GAA | CTA | GAG | GAC | GAT | GAC | GTT | TTG | 3950 |
| Arg | Ile | Asp | Asp | Val | Asn | Ile | Thr | Glu | Leu | Glu | Asp | Asp | Asp | Val | Leu | |
| | | | | 880 | | | | | 885 | | | | | 890 | | |
| AAA | GGT | GGC | GAA | GAA | GCT | TCT | GAT | TCG | AGG | ACT | GCC | TAT | ATT | TTA | ATG | 3998 |
| Lys | Gly | Gly | Glu | Glu | Ala | Ser | Asp | Ser | Arg | Thr | Ala | Tyr | Ile | Leu | Met | |
| | | | 895 | | | | | 900 | | | | | 905 | | | |
| TAT | CAA | AAG | AGA | AAT | TAAGACGGGG | GGTGGTATTA | TAGACAAAAT | ACATAAAAAA | | | | | | | | 4053 |
| Tyr | Gln | Lys | Arg | Asn | | | | | | | | | | | | |
| | | 910 | | | | | | | | | | | | | | |

| | | | | | |
|---|---|---|---|---|---|
| TAATATAGCA | ATAATACAAT | ACAATACAAT | ACAATACGAT | AGTGAGCACG | ATTTTAAAA | 4113 |
| AGAAATAGAG | ACAGACAGAG | AAACAGAGTT | ACACTTTATG | CTTGGCATAT | TTAAAAAAT | 4173 |
| ATTTCGCCCA | GGATCGAACT | GGGGACGTTC | TGCGTGTTAA | GCAGATGCCA | TAACCGACT | 4233 |
| GACCACGAAA | CCAATTATTT | CTTGGAGATG | AACATTTAAG | AAACAAATAC | CTTGTAGAA | 4293 |
| GAATGTGAAT | TTCAAAATAT | TATGGCCTTT | GGCAACAATG | GAATCACAAC | AATTATCAC | 4353 |
| AAACTCATAC | ATCTCTTAAG | ATTCATTTCT | TACTTTAAGT | AATCATCCAA | ATTTAGCCA | 4413 |
| AGTTTGATTT | TACCTAAAAA | AAGCAGAGGA | TTCCCGATTT | CAATCATATG | TGCACAGAC | 4473 |
| ATGAGTCCAA | CACGTTATCG | TTAACATAGT | GCTCAATATT | GCCACTGCGC | TTCGCAGGA | 4533 |
| CATATTTCGT | ATACGCCAAG | CCCAAGGAGG | GTTTTGTCAT | TAAGCAGCTT | ACGCCAATT | 4593 |
| AGTGCTAACC | TCGAAGCACC | ATACTTATC | TCAGGATTTA | CAAACTCCCT | ATTGCACAA | 4653 |
| GGCAAACAAC | ATAATCATGA | CCAAATGGGT | AAAAAGATG | AGCTGTGAAA | AAGCCAAAA | 4713 |
| AAAAAAGGAA | GAACTAGAAT | TACATTTATT | ATTCTACACA | CAAAAGAAA | AAATAGTTT | 4773 |
| TTTATTTAAA | TGATTTGAAG | AAAAAGAACT | ATAACGACTA | CATCGAAGAA | TACAATATT | 4833 |
| GTAAAAAACA | CATGTCCTGT | TTAAAATAAG | TCTCTAGTTA | AAGACTATTC | GATC | 4887 |

( 2 ) INFORMATION FOR SEQ ID NO:8:

( i ) SEQUENCE CHARACTERISTICS:

(A) LENGTH: 912 amino acids
(B) TYPE: amino acid
(D) TOPOLOGY: linear (ii) MOLECULE TYPE: protein (xi) SEQUENCE DESCRIPTION: SEQ ID NO:8:

```
Met Asn Met Gln Asp Ala Asn Lys Glu Glu Ser Tyr Ser Met Tyr Pro
  1               5                  10                  15
Lys Thr Ser Ser Pro Pro Pro Thr Pro Thr Asn Met Gln Ile Pro
                 20              25                  30
Ile Tyr Gln Ala Pro Leu Gln Met Tyr Gly Tyr Thr Gln Ala Pro Tyr
             35              40                  45
Leu Tyr Pro Thr Gln Ile Pro Ala Tyr Ser Phe Asn Met Val Asn Gln
     50              55                  60
Asn Gln Pro Ile Tyr His Gln Ser Gly Ser Pro His His Leu Pro Pro
 65              70                  75                      80
Gln Asn Asn Ile Asn Gly Gly Ser Thr Thr Asn Asn Asn Asn Ile Asn
                 85              90                      95
Lys Lys Lys Trp His Ser Asn Gly Ile Thr Asn Asn Asn Gly Ser Ser
                100             105                 110
Gly Asn Gln Gly Ala Asn Ser Ser Gly Ser Gly Met Ser Tyr Asn Lys
             115             120                 125
Ser His Thr Tyr His His Asn Tyr Ser Asn Asn His Ile Pro Met Met
    130             135                 140
Ala Ser Pro Asn Ser Gly Ser Asn Ala Gly Met Lys Lys Gln Thr Asn
145                 150                 155                 160
Ser Ser Asn Gly Asn Gly Ser Ser Ala Thr Ser Pro Ser Tyr Ser Ser
                165                 170                 175
Tyr Asn Ser Ser Ser Gln Tyr Asp Leu Tyr Lys Phe Asp Val Thr Lys
                180             185                 190
Leu Lys Asn Leu Lys Glu Asn Ser Asn Leu Ile Gln Leu Pro Leu
        195             200                 205
Phe Ile Asn Thr Thr Glu Ala Glu Phe Ala Ala Ala Ser Val Gln Arg
210                 215                 220
Tyr Glu Leu Asn Met Lys Ala Leu Asn Leu Asn Ser Glu Ser Leu Glu
225                 230                 235                 240
Asn Ser Ser Val Glu Lys Ser Ser Ala His His Thr Lys Ser His
                245                 250                 255
Ser Ile Pro Lys His Asn Glu Glu Val Lys Thr Glu Thr His Gly Glu
            260                 265                 270
Glu Glu Asp Ala His Asp Lys Lys Pro His Ala Ser Lys Asp Ala His
        275                 280                 285
Glu Leu Lys Lys Lys Thr Glu Val Lys Lys Glu Asp Ala Lys Gln Asp
    290                 295                 300
Arg Asn Glu Lys Val Ile Gln Glu Pro Gln Ala Thr Val Leu Pro Val
305                 310                 315                 320
Val Asp Lys Lys Glu Pro Glu Glu Ser Val Glu Glu Asn Thr Ser Lys
                325                 330                 335
Thr Ser Ser Pro Ser Pro Ser Pro Pro Ala Ala Lys Ser Trp Ser Ala
            340                 345                 350
Ile Ala Ser Asp Ala Ile Lys Ser Arg Gln Ala Ser Asn Lys Thr Val
        355                 360                 365
Ser Gly Ser Met Val Thr Lys Thr Pro Ile Ser Gly Thr Thr Ala Gly
    370                 375                 380
```

| | | | | | | | | | | | | | | |
|---|---|---|---|---|---|---|---|---|---|---|---|---|---|---|
| Val | Ser | Ser | Thr | Asn | Met | Ala | Ala | Ala | Thr | Ile | Gly | Lys | Ser | Ser | Ser |
| 385 | | | | 390 | | | | 395 | | | | | 400 | | |
| Pro | Leu | Leu | Ser | Lys | Gln | Pro | Gln | Lys | Lys | Asp | Lys | Lys | Tyr | Val | Pro |
| | | | 405 | | | | 410 | | | | | 415 | | | |
| Pro | Ser | Thr | Lys | Gly | Ile | Glu | Pro | Gly | Ser | Ile | Ala | Leu | Arg | Met |
| | | | 420 | | | | 425 | | | | 430 | | | |
| Cys | Phe | Asp | Pro | Asp | Phe | Ile | Ser | Tyr | Val | Leu | Arg | Asn | Lys | Asp | Val |
| | | 435 | | | | 440 | | | | | 445 | | | | |
| Glu | Asn | Lys | Ile | Pro | Val | His | Ser | Ile | Ile | Pro | Arg | Gly | Ile | Ile | Asn |
| | 450 | | | | 455 | | | | | 460 | | | | | |
| Arg | Ala | Asn | Ile | Cys | Phe | Met | Ser | Ser | Val | Leu | Gln | Val | Leu | Leu | Tyr |
| 465 | | | | 470 | | | | 475 | | | | | 480 | | |
| Cys | Lys | Pro | Phe | Ile | Asp | Val | Ile | Asn | Val | Leu | Ser | Thr | Arg | Asn | Thr |
| | | | 485 | | | | 490 | | | | | 495 | | | |
| Asn | Ser | Arg | Val | Gly | Thr | Ser | Ser | Cys | Lys | Leu | Leu | Asp | Ala | Cys | Leu |
| | | | 500 | | | | 505 | | | | | 510 | | | |
| Thr | Met | Tyr | Lys | Gln | Phe | Asp | Lys | Glu | Thr | Tyr | Glu | Lys | Lys | Phe | Leu |
| | | 515 | | | | 520 | | | | | 525 | | | | |
| Glu | Asn | Ala | Asp | Asp | Ala | Glu | Lys | Thr | Thr | Glu | Ser | Asp | Ala | Lys | Lys |
| | 530 | | | | 535 | | | | | 540 | | | | | |
| Ser | Ser | Lys | Ser | Lys | Ser | Phe | Gln | His | Cys | Ala | Thr | Ala | Asp | Ala | Val |
| 545 | | | | 550 | | | | 555 | | | | | 560 | | |
| Lys | Pro | Asp | Glu | Phe | Tyr | Lys | Thr | Leu | Ser | Thr | Ile | Pro | Lys | Phe | Lys |
| | | | 565 | | | | 570 | | | | | 575 | | | |
| Asp | Leu | Gln | Trp | Gly | His | Gln | Glu | Asp | Ala | Glu | Glu | Phe | Leu | Thr | His |
| | | | 580 | | | | 585 | | | | | 590 | | | |
| Leu | Leu | Asp | Gln | Leu | His | Glu | Glu | Leu | Ile | Ser | Ala | Ile | Asp | Gly | Leu |
| | | 595 | | | | 600 | | | | | 605 | | | | |
| Thr | Asp | Asn | Glu | Ile | Gln | Asn | Met | Leu | Gln | Ser | Ile | Asn | Asp | Glu | Gln |
| 610 | | | | 615 | | | | | 620 | | | | | | |
| Leu | Lys | Val | Phe | Phe | Ile | Arg | Asn | Leu | Ser | Arg | Tyr | Gly | Lys | Ala | Glu |
| 625 | | | | 630 | | | | | 635 | | | | | 640 | |
| Phe | Ile | Lys | Asn | Ala | Ser | Pro | Arg | Leu | Lys | Glu | Leu | Ile | Glu | Lys | Tyr |
| | | | 645 | | | | 650 | | | | | 655 | | | |
| Gly | Val | Ile | Asn | Asp | Asp | Ser | Thr | Glu | Glu | Asn | Gly | Trp | His | Glu | Val |
| | | | 660 | | | | 665 | | | | | 670 | | | |
| Ser | Gly | Ser | Ser | Lys | Arg | Gly | Lys | Thr | Lys | Thr | Ala | Ala | Lys | Arg |
| | | 675 | | | | 680 | | | | | 685 | | | | |
| Thr | Val | Glu | Ile | Val | Pro | Ser | Pro | Ile | Ser | Lys | Leu | Phe | Gly | Gly | Gln |
| | 690 | | | | 695 | | | | | 700 | | | | | |
| Phe | Arg | Ser | Val | Leu | Asp | Ile | Pro | Asn | Asn | Lys | Glu | Ser | Gln | Ser | Ile |
| 705 | | | | | 710 | | | | 715 | | | | | 720 | |
| Thr | Leu | Asp | Pro | Phe | Gln | Thr | Ile | Gln | Leu | Asp | Ile | Ser | Asp | Ala | Gly |
| | | | | 725 | | | | | 730 | | | | | 735 | |
| Val | Asn | Asp | Leu | Glu | Thr | Ala | Phe | Lys | Lys | Phe | Ser | Glu | Tyr | Glu | Leu |
| | | | 740 | | | | | 745 | | | | 750 | | | |
| Leu | Pro | Phe | Lys | Ser | Ser | Ser | Gly | Asn | Asp | Val | Glu | Ala | Lys | Lys | Gln |
| | | 755 | | | | | 760 | | | | | 765 | | | |
| Thr | Phe | Ile | Asp | Lys | Leu | Pro | Gln | Val | Leu | Leu | Ile | Gln | Phe | Lys | Arg |
| | 770 | | | | | 775 | | | | | 780 | | | | |
| Phe | Ser | Phe | Ile | Asn | Asn | Val | Asn | Lys | Asp | Asn | Ala | Met | Thr | Asn | Tyr |
| 785 | | | | | 790 | | | | | 795 | | | | | 800 |
| Asn | Ala | Tyr | Asn | Gly | Arg | Ile | Glu | Lys | Ile | Arg | Lys | Lys | Ile | Lys | Tyr |
| | | | | 805 | | | | 810 | | | | | 815 | | |

| Gly | His | Glu | Leu<br>820 | Ile | Ile | Pro | Glu | Glu<br>825 | Ser | Met | Ser | Ser | Ile<br>830 | Thr | Leu |
| --- | --- | --- | --- | --- | --- | --- | --- | --- | --- | --- | --- | --- | --- | --- | --- |
| Lys | Asn | Asn<br>835 | Thr | Ser | Gly | Ile | Asp<br>840 | Asp | Arg | Arg | Tyr | Lys<br>845 | Leu | Thr | Gly |
| Val | Ile<br>850 | Tyr | His | His | Gly | Val<br>855 | Ser | Ser | Asp | Gly | Gly<br>860 | His | Tyr | Thr | Ala |
| Asp<br>865 | Val | Tyr | His | Ser | Glu<br>870 | His | Asn | Lys | Trp | Tyr<br>875 | Arg | Ile | Asp | Asp | Val<br>880 |
| Asn | Ile | Thr | Glu | Leu<br>885 | Glu | Asp | Asp | Asp | Val<br>890 | Leu | Lys | Gly | Gly | Glu<br>895 | Glu |
| Ala | Ser | Asp | Ser | Arg<br>900 | Thr | Ala | Tyr | Ile | Leu<br>905 | Met | Tyr | Gln | Lys | Arg<br>910 | Asn |

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:9:

| Gly | Gly | Gly | Ser |
| --- | --- | --- | --- |
| 1 | | | |

UBIQUITIN-SPECIFIC PROTEASES

GOVERNMENT FUNDING

This invention was partially supported by the U.S. Government and the government has certain rights to the invention.

This application is a division of application Ser. No. 07/789,915 filed on Nov. 8, 1991, now U.S. Pat. No. 5,212,058, which is a CIP of Ser. No. 07/573,958, filed on Aug. 28, 1990, now abandoned, which is a CIP of Ser. No. 07/521,089, filed May 9, 1990, now abandoned.

BACKGROUND OF THE INVENTION

Ubiquitin (Ub), a highly conserved 76-residue protein, is present in eukaryotic cells either free or covalently joined to a great variety of proteins. The posttranslational coupling of ubiquitin to other proteins is catalyzed by a family of Ub-conjugating (E2) enzymes and involves formation of an isopeptide bond between the C-terminal Gly residue of ubiquitin and the $\epsilon$-amino group of a Lys residue in an acceptor protein. One function of ubiquitin is to mark proteins destined for selective degradation. Ubiquitin was also shown to have a chaperone function, in that its transient (cotranslational) covalent association with specific ribosomal proteins promotes the assembly of ribosomal subunits.

Unlike branched Ub-protein conjugates, which are formed posttranslationally, linear Ub-protein adducts are formed as the translational products of natural or engineered gene fusions. Thus, in the yeast *Saccharomyces cerevisiae* for example, ubiquitin is generated exclusively by proteolytic processing of precursors in which ubiquitin is joined either to itself, as in the linear polyubiquitin protein Ubi4, or to unrelated amino acid sequences, as in the hybrid proteins Ubi1–Ubi3. In growing yeast cells, ubiquitin is generated largely from the Ubi1–Ubi3 precursors whose "tails" are specific ribosomal proteins. The polyubiquitin (UBI4) gene is dispensable in growing cells but becomes essential (as the main supplier of ubiquitin) during stress. The lack of genes encoding mature ubiquitin, and the fusion structure of ubiquitin precursors in yeast are characteristic of other eukaryotes as well.

Ub-specific, ATP-independent proteases capable of cleaving ubiquitin from its linear or branched conjugates have been detected in all eukaryotes examined but not in bacteria such as *Escherichia coli*, which lack ubiquitin and Ub-specific enzymes. Miller et al. (*Biotechnology* 1: 698–704 (1989)) have cloned a *S. cerevisiae* gene, named YUH1, encoding a Ub-specific protease that cleaves ubiquitin from its relatively short C-terminal extensions but is virtually inactive with larger fusions such as Ub-β-galactosidase (Ub-βgal). Wilkinson et al. (*Science* 246: 670–673 (1989)) have also cloned a cDNA encoding a mammalian homolog of the yeast Yuh1 protease. Tobias and Varshavsky (*J. Biol. Chem.* 266: 12021–12028 (1991)) reported the cloning and functional analysis of another yeast gene, named UBP1, which encodes a Ub-specific processing protease whose amino acid sequence is dissimilar to those of the Yuh1 protease and other known proteins. Unlike YUH1 and its known homologues in other species, Ubp1 deubiquitinates ubiquitin fusion proteins irrespective of their size or the presence of an N-terminal ubiquitin extension.

SUMMARY OF THE INVENTION

The subject invention relates to a genetic class of ubiquitin-specific proteases which specifically cleave at the C-terminus of the ubiquitin moiety in a ubiquitin fusion protein irrespective of the size of the ubiquitin fusion protein. More specifically, the invention relates to ubiquitin-specific proteases of this class which have been isolated from a cell. The invention also relates to isolated DNA sequences encoding the proteases of this class.

One useful property of ubiquitin-specific proteases is that they cleave ubiquitin from its C-terminal extensions irrespective of the identity of the extension's residue abutting the cleavage site. This property of the Ubp proteases make possible the in vivo or in vitro generation of proteins or peptides bearing predetermined N-terminal residues, a method with applications in both basic research and biotechnology.

DETAILED DESCRIPTION OF THE INVENTION

Figure 1:
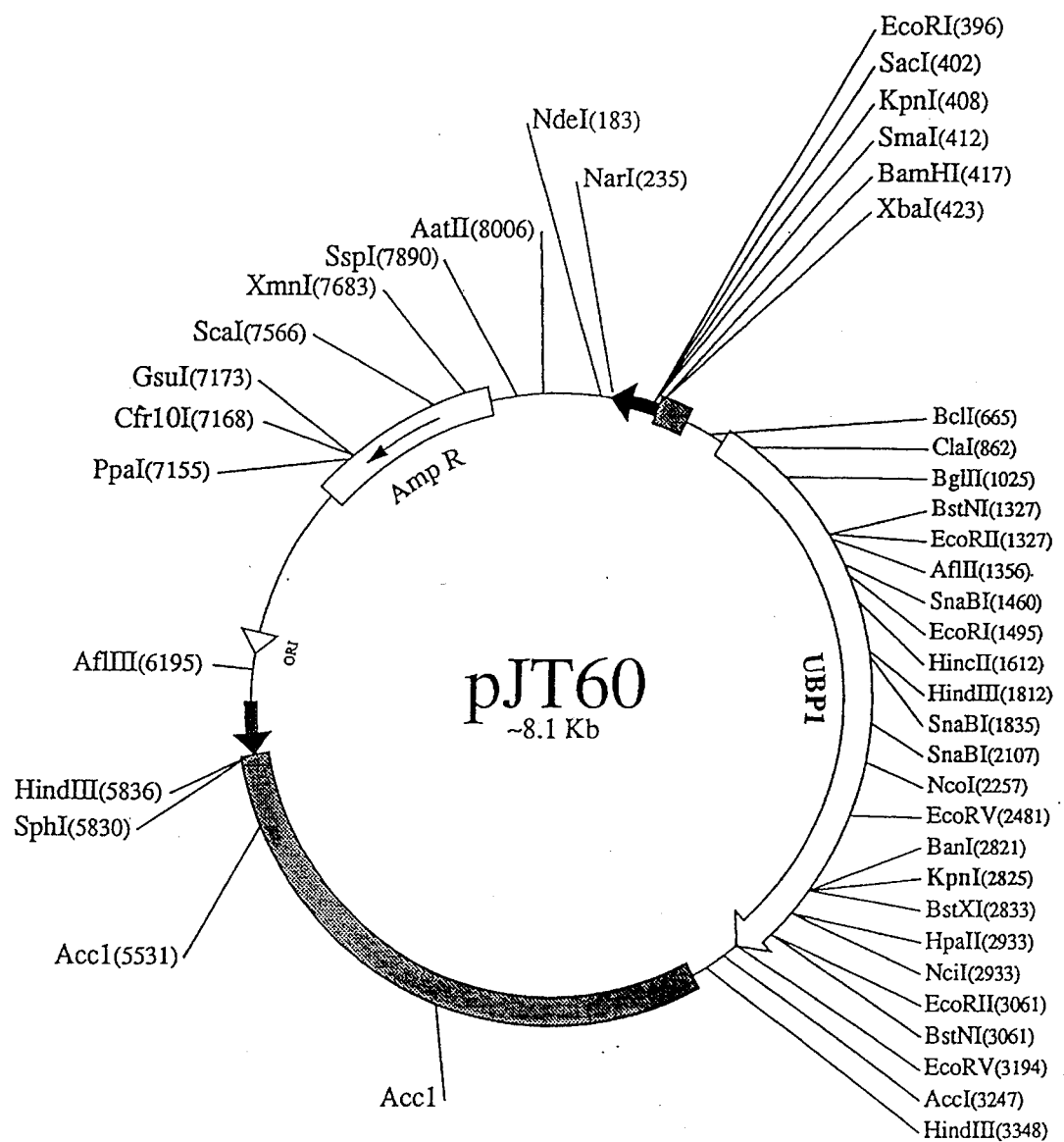
FIG. 1 is a diagram representing the plasmid pJT60.

A ubiquitin fusion protein, as used herein, is defined as a fusion protein comprising ubiquitin or its functional homolog having its C-terminal amino acid residue fused to the N-terminal amino acid residue of a non-ubiquitin protein or peptide. As discussed in the Examples which follow, the ubiquitin fusion protein can be a naturally occurring fusion protein, or a fusion protein produced by recombinant DNA technology. The specific cleavage takes place either in vivo or in vitro, between the C-terminal residue of ubiquitin and the N-terminal residue of the protein or peptide.

In contrast to the class of ubiquitin-specific proteases disclosed herein, the previously isolated YUH1 enzyme cleaves ubiquitin off a ubiquitin fusion protein only if the non-ubiquitin portion of the fusion is relatively short (shorter than about 60 residues). Since, for instance, many of the pharmaceutically important proteins are much longer than 60 residues, the YUH1 protease cannot be used to deubiquitinate fusions of these proteins with ubiquitin. The proteases of the class disclosed herein, however, can be used for this purpose, thereby allowing the generation of desired residues at the N-termini of either large or small proteins, polypeptides or peptides (the terms protein, polypeptide and peptide are often used interchangeably in the art).

Disclosed in the Examples which follow are DNA sequences which encode three of the proteases which are members of the class of ubiquitin-specific proteases to which this invention pertains. These proteases have been designated UBP1, UBP2 and UBP3. The DNA sequences which encode these proteases, and their deduced amino acid sequences, are set forth in Sequence I.D. Numbers 3–4, Sequence I.D. Numbers 5–6 and Sequence I.D. Numbers 7–8, respectively. The DNA sequences which encode the proteases disclosed herein can be isolated by the methods described below, or by using the polymerase chain reaction amplification method. Primer sequences to be used in such an amplification method can be determined by reference to the DNA Sequence Listing below.

The proteases UBP1 and UBP2 demonstrate activity both in vivo and in vitro, whereas the UBP3 protease demonstrates activity only in vivo. Each of these proteases has been shown to specifically cleave a ubiquitin fusion protein having a molecular weight of about 120 kilodaltons (ubiquitin-methionine-β-galactosidase). By contrast, the YUH1 ubiquitin-specific protease is virtually inactive with this ubiquitin fusion either in vitro or in vivo. The DNA sequence encoding this 120 kilodalton fusion protein is represented in Sequence I.D. Number 1. The amino acid sequence is represented in Sequence I.D. Numbers 1–2.

The scope of the invention encompasses an isolated DNA sequence encoding a ubiquitin-specific protease, or a biologically active portion thereof, which is characterized by the ability to hybridize specifically with the DNA sequence represented in Sequence I.D. Number 3, Sequence I.D. Number 5 or Sequence I.D. Number 7, under stringent hybridization conditions. DNA sequences which hybridize to the listed sequences under stringent hybridization conditions are either perfectly complementary, or highly homologous to the listed sequence. Homologous, as used herein, refers to DNA sequences which differ from the listed sequence, but the difference has no substantial effect on the biological activity (i.e., cleavage properties) of the encoded protease. One of the possible sets of stringent hybridization conditions is 50% formamide, 5×SSPE (1×SSPE is 0.15 mNaCl, 1 mM Na-EDTA, 10 mM Na-phosphate, pH 7.0), 5×Denhardt's solution (0.1% polyvinylpyrrolidone, 0.1% Ficoll) at 45° C.

The isolated DNA sequences which fall within the scope of this invention can be used to express the encoded protease in large quantities in either prokaryotic or eukaryotic host cells. For this purpose, the DNA is inserted into a prokaryotic or eukaryotic expression vector, with the appropriate regulatory signals, and used to transform cells. A variety of appropriate vectors and regulatory signals have been previously developed for this purpose and are well known to those skilled in the art.

As discussed in the Examples below, the proteases of this invention have been overexpressed in *E. coli* to the extent that they represent a substantial proportion of the total cellular protein. The purification of a protein which is expressed at such substantial levels, and for which a simple assay system is established, is a straightforward matter to one skilled in the art.

Isolated UBP1 or UBP2, or a cellular extract containing UBP1 or UBP2 produced from a recombinant DNA expression vector can be used to cleave ubiquitin off ubiquitin fusions in vitro. A cellular extract can be prepared from a culture of host cells expressing a recombinant DNA expression vector by simply concentrating and lysing the cell culture. The lysis can be followed, optionally, by various degrees of purification as described above. The range of conditions appropriate for in vitro cleavage can be determined empirically by one skilled in the art, using no more than routine experimentation, from the information provided in the Examples which follow.

In addition, the UBP1, UBP2 and UBP3 proteases can be used to deubiquitinate fusion proteins in vivo. For example, prokaryotic cells harboring an expression vector encoding the protease can be transformed with an expression vector encoding a ubiquitin fusion protein. Such cells will produce a deubiquitinated product having a predetermined N-terminal amino acid residue. There are many well known advantages to producing recombinant proteins in prokaryotic organisms such as *E. coli*.

In some fusions of ubiquitin to a non-ubiquitin protein or peptide, the presence of the ubiquitin moiety may inhibit or modify the functional activity of the non-ubiquitin protein or peptide. In this case, ubiquitin can be used as a temporary inhibitor (or modifier) of the functional activity of the non-ubiquitin protein or peptide, with the ability to restore the original functional activity at any desired time, either in vitro or in vivo, by contacting the corresponding ubiquitin fusion with the ubiquitin-specific protease to remove the ubiquitin moiety.

The invention is further illustrated by the following Examples.

EXAMPLES

Example 1: Cloning and Analysis of UBP1

Preparation of Yeast Genomic DNA Library and Lysate for Screening

*Escherichia coli* (strain HB101) transformed with a *Saccharomyces cerevisiae* genomic library was used for a sib selection strategy. The library, RB237, was produced by partially digesting yeast genomic DNA with SauIIIA and ligating the fragments into the BamH1 site in the Tet™ gene of the yeast/*E. coli* shuttle vector YCp50. Upon initial analysis, the library contained inserts with an average size of ~19 Kb.

*E. coli*, transformed with the above library, were plated on agar containing Luria Broth (LB) and ampicillin (amp) (100 μg/ml) at a density of about 40 viable cells per plate. The plates were incubated at 36° C. for 16 hours. The colonies were then replicated onto LB/amp plates. The original plates were stored at 4° C., and their replicas were grown for 24 hours at 36° C. Each replicate was eluted with 1 ml of LB/amp (50 μg/ml) by repeated washing over the surface of the plate until all of the colonies were loosened into the liquid. The entire eluate was then added to 4 ml of LB/amp, and incubated on a roller drum at 36° C. overnight.

The *E. coli* cells in these overnight (stationary-phase) cultures were then lysed. 1.7 ml of each culture was placed in a microcentrifuge tube on ice, and then centrifuged at 12,000×g for 1 min at 4 ° C. The cell pellet was resuspended, by vortexing at high speed, in 50 μl of 25% sucrose (w/v), 250 mM Tris-HCl (pH 8.0). 10 μl of freshly made lysozyme solution (10 mg/ml chicken egg-white lysozyme (Sigma) in 0.25M Tris-HCl (pH 8.0)) was then added, and mixed by light vortexing. The suspension was incubated on ice for 5 minutes, 150 μl of 75 mM EDTA, 0.33M Tris-HCl (pH 8.0) was then added, mixed by light vortexing, and the tube was incubated on ice for 5 minutes with occasional stirring. 1 μl of 10% Triton X-100 (Pierce) was then added to each tube, and mixed by pipetting. The cell lysate was centrifuged at 12,000×g for 15 minutes at 4° C. The supernatant was retained on ice, and the pellet was discarded.

Preparation of Labeled Substrate

Cell lysates were assayed for the Ub-specific protease activity using a $^{35}$S-labeled substrate. $^{35}$S-labeled ubiquitin-methionine-dihydrofolate reductase (Ub-Met-DHFR) was prepared as follows: Luria Broth (50 ml) supplemented with 50 μg/ml ampicillin was inoculated with 1 ml of a saturated overnight culture of *E. coli* strain JM101 containing a plasmid expressing the Ub-Met-DHFR fusion protein from an IPTG-inducible, highly active derivative of the lac promoter. The cells were grown with shaking at 37° C. until they reached an $A_{600}$ of ~0.9. The culture was chilled on ice for 15 minutes, then centrifuged at 3000×g for 5 minutes and washed 2 times with M9 salts at 0° C. The cells were resuspended after the 10 final wash in 25 ml of M9 salts supplemented with 0.2% glucose, 1.8 μg/ml thiamine, 40 μg/ml ampicillin, 1 mM IPTG, 0.0625% (w/v) methionine assay medium (Difco). The suspension was then shaken for 1 hour at 37° C. and the cells were labeled by the addition of 1 mCi of $^{35}$S-Translabel (ICN), followed by a 5-min incubation, with shaking. Unlabeled L-methionine was then added to a final concentration of 0.0032% (w/v), and the cells were shaken for an additional 10 min. The cells were then harvested (3000×g for 5 minutes) and washed once in cold M9 salts. After the M9 wash, the cell pellet was resuspended in 0.5 ml 25% Sucrose, 50 mM Tris-HCl (pH 8.0), and incubated on ice for 5 minutes. During this time, chicken egg-white lysozyme (Sigma) was dissolved freshly in 250 mM Tris-HCl (pH 8.0) to a concentration of 10 mg/ml. 10 μl of the lysozyme solution was added to the cell suspension, mixed, and incubated for 5 minutes at 0° C. 5 μl of 0.5M EDTA (pH 8.0) was then added, and the suspension left at 0° C. for 5 minutes, with intermittent mixing. The cell suspension was then added to a centrifuge tube containing 0.975 ml of 65 mM EDTA (pH 8.0), 50 mM Tris-HCl (pH 8.0) and protease inhibitors antipain, chymostatin, leupeptin, aprotinin and pepstatin, each at 25 μg/ml. 10 μl 10% Triton X-100 (Pierce) was then added, and dispersed by pipetting. The lysate was centrifuged at 39,000×g for 30 minutes. The supernatant was retained, quickly frozen in liquid nitrogen, and stored at –85° C.

To affinity-purify the $^{35}$S-labeled Ub-Met-DHFR, a methotrexate (MTX)-agarose affinity matrix was prepared according to the method of Kaufman (*Meth. Enzymol.* 34:272–281 (1974)). A 0.5 ml bed volume column was filled with the MTX-agarose, and washed with 10 ml of MTX column buffer (20 mM Hepes (pH 7.5), 1 mM EDTA 200 mM NaCl, 0.2 mM dithiothreitol). The $^{35}$S-labeled supernatant of the preceding step was thawed and applied to the MTX-agarose column. The column was washed with 50 ml of MTX column buffer, 50 ml of MTX column buffer containing 2M urea, and again with 50 ml of MTX column buffer. The labeled Ub-Met-DHFR was eluted from the column with folic acid elution buffer (0.2M potassium borate (pH 9.0), 1M KCl, 1 mM DTT, 1 mM EDTA, 10 mM folic acid). The elution buffer was applied to the column in 1 ml aliquots, and 1 ml fractions were collected. The fractions were assayed for $^{35}$S radioactivity and those fractions that contained the major radioactive peak were pooled. The pooled fractions were dialyzed for ~20 hours against two changes of a storage buffer containing 40 mM Tris-HCl (pH 7.5), 1 mM MgCl$_2$, 0.1 mM EDTA, 50% glycerol. The purified $^{35}$S-labeled Ub-Met-DHFR was assayed by SDS-PAGE, followed by fluorography and found to be greater than 95% pure.

Deubiquianation Assay

The cell lysates were assayed for the Ub-specific protease activity, by combining 9 μl of the cell lysate supernatant with 1 μl of the affinity purified $^{35}$S-labeled Ub-Met-DHFR fusion in a 0.5 ml microcentrifuge tube, and incubated at 36° C. for 3 hr. 5 μl of a 3-fold concentrated electrophoretic sample buffer (30% glycerol, 3% SDS (w/v), 15 mM EDTA, 0.2M 2-mercaptoethanol, 0.3 μg/ml bromophenol blue, 375 mM Tris-HCl (pH 6.8) was then added, and each tube was placed in a boiling water bath for 3 min. The samples were loaded onto a 12% polyacrylamide-SDS gel, and electrophoresed at 50 V until the bromophenol dye reached the bottom of the gel. Positions of the radioactively labeled proteins in the gel were visualized by fluorography. The gel was washed in 10% acetic acid, 25% methanol for 15 minutes, rinsed in H$_2$O for 15 minutes and incubated with Autofluor (National Diagnostics) for 1 hour. The gel was then dried at 80° C. under vacuum, placed in a light-proof cassette against Kodak XAR-5 film and stored at –85 ° C. overnight.

The above deubiquitination assay was repeated with lysates from different pools of *E. coli* transformants until the gel analysis revealed a lysate that displayed proteolytic activity acting at the ubiquitin-DHFR junction. This assay indicated that at least one of the ~40 *E. coli* colonies on the original LB/amp plate (from which the pooled lysate had been derived) contained a YCp50-based plasmid having a yeast DNA insert conferring Ub-specific protcolytic activity.

The next step of this sib selection approach to cloning the UBP1 gene was to carry out a similar Ub-Met-DHFR cleavage assay to determine which of the ~40 colonies in a "positive" pool contained the desired plasmid. To do so, a sample of each individual colony on the plate of interest was inoculated into LB/amp and grown overnight. The Ub-Met-DHFR cleavage assay was then repeated exactly as above, but this time each lysate sample was representative of a single clonal *E. coli* transformant rather than a mixture of ~40 such transformants. This analysis revealed a single colony that contained a plasmid which conferred the ability to specifically cleave at the Ub-DHFR junction.

Cloning and DNA Sequence Analysis of UBP1

Analysis of the initially isolated plasmid (pJT55) revealed a ~15 kb insert of yeast genomic DNA in the YCp50 vector. SphI digestion of this plasmid yielded a ~14 kb fragment, which, upon subcloning into the vector pUC19, conferred the same proteolytic activity. This plasmid was called pJT57. The ~14 kb fragment was subcloned further by cutting with SphI and XhoI, isolating the ~5.5 kb of the insert DNA and subcloning it into the pUC19 vector pre-cut with SphI and SalI. This resulted in ~8.1 kb plasmid pJT60 containing the ~5.5 kb yeast DNA insert that conferred the same Ub-specific proteolytic activity as the original plasmid.

A map showing restriction endonuclease recognition sites in plasmid pJT60 is shown in FIG. 1. In the map, base pair positions are indicated by a number in parentheses following a restriction site. The yeast DNA insert in pJT60 contained a KpnI site near its center that divided the insert into two smaller fragments A and B (bases 423 and 5830). In this fragment, the open arrow indicates the open reading frame (ORF) representing UBP1. The entire ORF, and the thin lines bracketing it, represent the extent of the sequenced DNA shown in Sequence I.D. Number 3. Both fragments were subcloned into pUC19, yielding pJT60A and pJT60B. Fragment A was isolated from pJT57 after cutting with KpnI and SphI. This fragment was subcloned into pUC19 that had been cut with the same restriction endonucleases. Fragment B was isolated from pJT57 that had been cut by KpnI and XhoI; it was subcloned into pUC19 that had been cut by KpnI and SalI. Neither pJT60A nor pJT60B was able to confer Ub-specific proteolytic activity. This result suggested that the gene of interest straddled the KpnI site of the ~5.5 kb insert of pJT60.

To sequence the cloned gene, the inserts of pJT60A and pJT60B were subcloned into the M13mp19 phage vector. Nucleotide sequence was determined (using the chain termination method) in both directions from the internal KpnI site in pJT60. The KpnI site was found to be ensconced within an open reading frame extending from this site in both directions. Unidirectional deletions were then made in the sequencing templates by the methods of Dale et al., (*Plasmid* 13:31–40 (1989)) and the entire open reading frame (ORF) was determined. The 5' end of the ORF was in fragment B and the termination codon was in fragment A.

The ORF was 2427 nucleotides long, and encoded an 809-residue protein, with a molecular mass of 93 kD. The sequenced ORF was then isolated on a 2.8 kb fragment by cutting pJT60 with AccI, filling in the 5' overhangs with Klenow PolI, and ligating SalI linkers to the blunt ends. This construct was digested with SalI and BamHI, the 2.8 kb fragment was electrophoretically purified and ligated into pUC19 that had been digested with BamHI and SalI. The resulting plasmid was called pJT70. This plasmid, when transformed into *E. coli,* was able to confer the Ub-specific proteolytic activity to the same extent as either the original ~15 kb insert in YCp50 or the ~5.5 kb insert of the pJT60 plasmid that includes the ~2.8 kb fragment of pJT70. The plasmid pJT60 has been deposited with the American Type Culture Collection (Rockville, Md.), and has been assigned ATCC designation 68211. The 2.8 kb fragment contained no other ORFs of significant size, indicating that the sequenced ORF shown in Sequence I.D. Number 3 encoded the Ub-specific protease. This new gene has been named UBP1, for Ubiquitin-specific protease.

Substrate Specificity of UBP1

The in vitro substrate specificity of the UBP1 encoded product was examined by testing for cleavage using a variety of substrates. These experiments demonstrated the ability of Ubp1 to deubiquitinate [$^{35}$S]Ub-Met-DHFR and [$^{35}$S]ubiquitin-methionine-β-galactosidase (Ub-Met-βgal). The construction of the [$^{35}$S]Ub-Met-βgal fusion protein has been described previously (Bachmair et al., Science 234: 179–186 (1986)). The labeled substrates were employed in a deubiquitination assay as described above. Both fusion proteins were specifically deubiquitinated. Fluorograms of electrophoretic patterns from these deubiquitination experiments revealed deubiquitination reaction products of the expected molecular mass.

The Ubp1 protease was also shown to deubiquitinate natural ubiquitin fusions to yeast ribosomal proteins (Ubi2 and Ubi3) in vitro. An expression construct encoding Ubi2, a natural ubiquitin-ribosomal protein fusion of *S. cerevisiae,* was used to transform *E. coli.* A cellular extract from a culture of the transformed cells was treated with an *E. coli* extract from cells expressing Ubp1, followed by electrophoresis in a polyacrylamide-SDS-gel, blotting onto polyvinylidene difluoride membrane, and detection using a rabbit anti-ubiquitin antibody, with subsequent application of a secondary goat anti-rabbit antibody linked to alkaline phosphatase, and colorgenic substrates of alkaline phosphatase. These experiments demonstrated that an extract from *E. coli* expressing the Ubp1 gene product effectively deubiquitinated the natural ubiquitin fusion proteins Ubi2 and Ubi3.

To determine whether a sandwich-type ubiquitin fusion protein in which the ubiquitin moiety had an N-terminal extension was a substrate for Ubp1, a plasmid was constructed that encoded a triple fusion protein consisting of an N-terminal dihydrofolate reductase (DHFR) moiety, a flexible linker region of three glycine residues and a serine, followed by ubiquitin and Met-βgal moieties. The mouse DHFR gene was isolated on a BamHI/HindIII fragment from a plasmid encoding Ub-Met-DHFR (Bachmair and Varshavsky, Cell 56:1019–1032 (1989)). This fragment was treated with Klenow PolI to fill in the ends, and KpnI linkers were ligated. The fragment was then cut with KpnI to yield a 678 bp fragment which was cloned into the KpnI site in a modified Ub-Met-βgal expression vector in which the second codon of the ubiquitin moiety was altered to encode a KpnI site (Gonda et al., J. Biol. Chem. 264:16700–16712 (1989)). This procedure yielded a plasmid that encoded DHFR, ubiquitin (without the initial Met codon) and Met-βgal, with the open reading frames for each moiety not yet aligned into a single open reading frame. To effect the alignment of the open reading frames and to position the initiator codon of DHFR correctly with respect to the GAL promoter in the vector, site-directed mutagenesis was performed at two locations in the plasmid.

The plasmid was cut with BamHI and HindIII, and the ~2.76 kb fragment encoding DHFR, ubiquitin and the first few residues of Met-βgal was cloned into M13mp19 that had been cut with the same enzymes. Oligonucleotide-mediated, site-directed mutagenesis was performed using the single-stranded M13 derivative and standard protocols. The first oligodeoxynucleotide was designed to produce a 20 bp deletion that would bring the initiator codon of DHFR to a proper position relative to the GAL5 promoter of the vector. The second oligodeoxynucleotide was designed to bring together the reading frames of DHFR and ubiquitin, and to introduce the 4-residue spacer (-Gly-Gly-Gly-Ser-) SEQ ID NO: 9 between the DHFR and ubiquitin moieties. After mutagenesis, DNA clones were tested for incorporation of both changes by direct nucleotide sequencing using the chain termination method.

Figure 2:
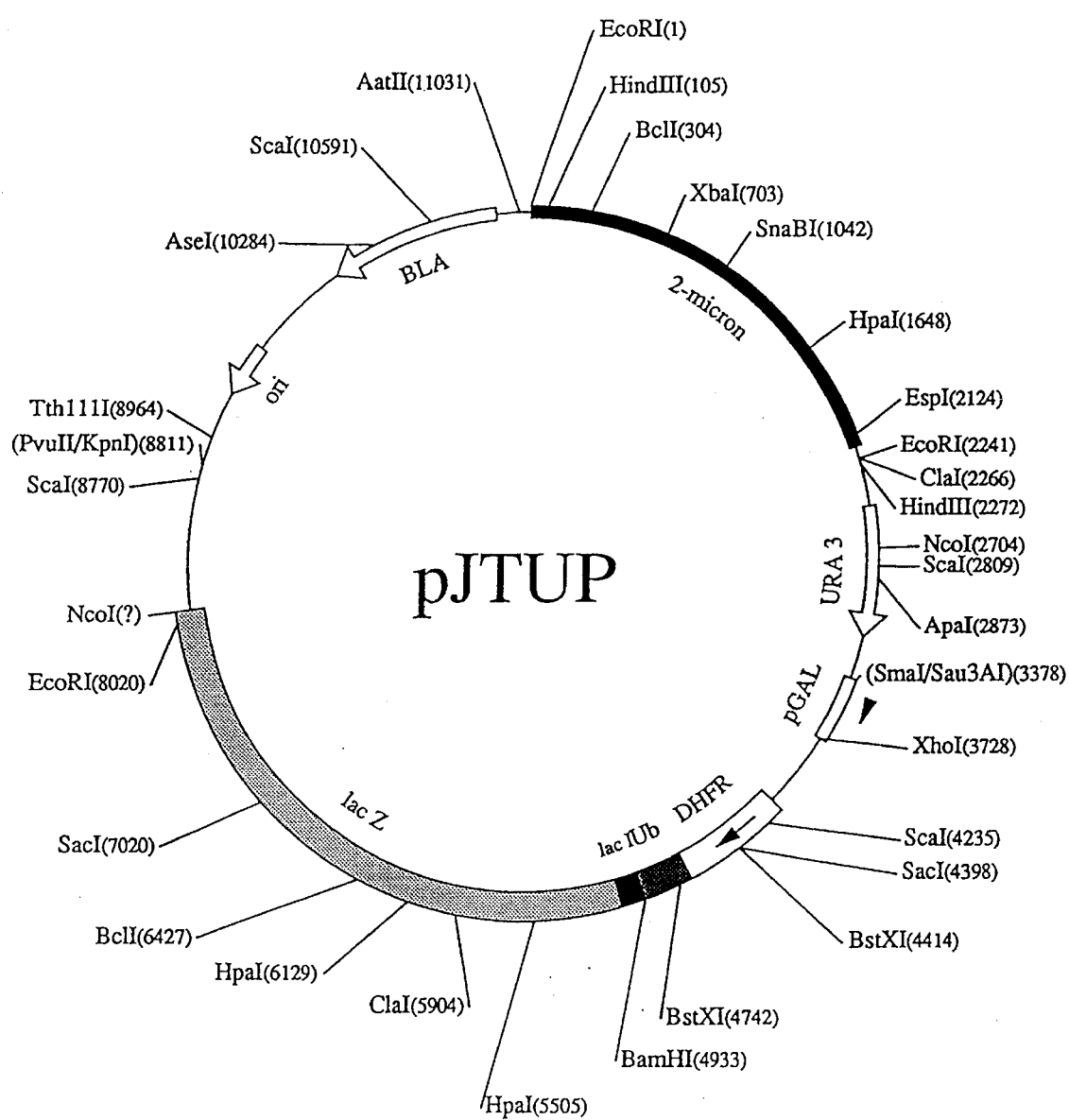
FIG. 2 is a diagram representing the plasmid pJTUP.

Double stranded, replicative form (RF) of the desired M13 clone was isolated and digested with BamHI and XhoI. The resulting ~1.2 kb fragment was cloned into the ~9.87 kb fragment of a Ub-Met-βgal expression vector digested with the same enzymes, replacing the Ub-Met-coding fragment with the DHFR-Ub-Met-coding fragment produced by the site-directed mutagenesis. This last step yielded an expression vector that encoded the triple fusion DHFR-Ub-Met-βgal. The vector was named pJTUP (FIG. 2).

pJTUP was used to test whether a ubiquitin fusion in which the ubiquitin moiety is located between two nonoubiquitin moieties would be a substrate for cleavage by Ubp1. In *E. coli* metabolically labelled with [$^{35}$S]methionine, the fate of expressed DHFR-Ub-Met-βgal was determined in the presence or absence of Ubp1 using immunoprecipitation with a monoclonal antibody to β-galactosidase, followed by polyacrylamide-SDS gel electrophoresis and fluorography. These experiments demonstrated that UBP1 efficiently cleaves the triple fusion protein.

The ability to cleave such a sandwich construct is particularly useful in situations wherein the first non-ubiquitin moiety confers some desirable property on the sandwich ubiquitin fusion. For example, the first non-ubiquitin moiety may facilitate affinity purification of the ubiquitin fusion protein. In such a case, the fusion protein can be expressed in a cell (e.g., *E. coli*) that lacks ubiquitin-specific proteases, and a cellular lysate can be passed over an affinity column specific for the first non-ubiquitin moiety. One example of a protein which is useful for affinity purification is streptavidin. Following affinity purification of the fusion protein, the latter is contacted with the ubiquitin-specific protease. The second non-ubiquitin moiety is thereby liberated from the sandwich ubiquitin fusion construct.

Example 2: Cloning and Analysis of UBP2 and UBP3

Cloning Strategy

The strategy employed to clone the genes encoding Ub-specific proteases of *S. cerevisiae* other than Ubp1 and Yuh1 took advantage of the fact that bacteria such as *E. coli* lack ubiquitin and Ub-specific enzymes, and was also based on the recent demonstration that the N-end rule, a relation between the in vivo half-life of a protein and the identity of its N-terminal residue, operates not only in eukaryotes but in *E. coli* as well. In eukaryotes, ubiquitin fusions to test proteins such as β-galactosidase are deubiquitinated by Ub-specific processing proteases irrespective of the identity of a residue at the Ub-βgal junction, making it possible to expose in vivo different residues at the N-termini of otherwise identical test proteins. This technique, required for detection and analysis of the N-end rule in eukaryotes, has been made applicable in bacteria through the isolation of the yeast UBP1 gene (see Example 1), inasmuch as *E. coli* transformed with UBP1 acquires the ability to deubiquitinate ubiquitin fusions. The finding that an X-βgal test protein such as Arg-βgal is short-lived in *E. coli,* whereas Ub-Arg-βgal is long-lived, made possible a new *E. coli*-based in vivo screen for Ub-specific proteases. *E. coli* expressing the (long-lived) Ub-Arg-βgal fusion protein form blue colonies on plates containing X-Gal, a chromogenic substrate of βgal. However, if a deubiquitinating activity is present in the cells as well, Ub-Arg-βgal is convened into a short-lived Arg-βgal, whose low steady-state level results in white *E. coli* colonies on X-Gal plates.

To be clonable by this strategy using a conventional yeast genomic DNA library, a yeast gene must have a promoter that functions in *E. coli* (a minority of yeast promoters can do so), must lack introns in its coding region (most yeast genes lack introns), and must encode a Ub-specific processing protease that functions as a monomer or a homooligomer. One advantage of this in vivo screen over the previously used in vitro screen that yielded UBP1 is that the former requires a relevant protease to be active in vivo but not necessarily in vitro (in *E. coli* extracts).

Plasmids Expressing Ubiquitin-Containing Test Proteins

The plasmid pACUb-R-βgal, expressing Ub-Arg-βgal, was constructed by subcloning the ~5 kb ScaI fragment of pUB23-R (Bachmair et al., *Science* 234: 179–186 (1986)) that contains the Ub-Arg-βgal coding region downstream from the GAL10 promoter, into HincII-digested pACYC184, whose P15A origin of replication makes this plasmid compatible with pMB1(ColE1)-based *E. coli* vectors such as pUC19 and pBR322. pACUb-R-βgal expressed Ub-Arg-βgal in *E. coli* from the galactose-inducible yeast GAL10 promoter, which functions as a weak constitutive promoter in *E. coli*. The plasmid pACUb-M-βgal, expressing Ub-Met-βgal, was constructed identically to pACUb-R-βgal except that pUB23-M was used instead of pUB23-R. Plasmids pKKUBI2, pKKUBI3 and pUB17 expressed in *E. coli* the natural yeast ubiquitin fusions (ubiquitin precursors) Ubi2, Ubi3 and Ubi4 (polyubiquitin), respectively (Ozkaynak et al., *EMBO J.* 6: 1429–1439 (1987)), using an isopropylthiogalactoside (IPTG)-inducible promoter in the vector pKK223-3 (Ausubel et al., *Current Protocols in Molecular Biology,* J. Wiley & Sons, N.Y. (1989)). The plasmids pKKHUb2 and pKKHUb3 that expressed, respectively, the human diubiquitin and triubiquitin (both of which contain the naturally occurring 1-residue C-terminal extension, cysteine), were constructed as follows. A 1.77 kb BamHI fragment containing the human UbB (triubiquitin) gene from the plasmid pB8.3 was ligated into BamHI-digested pUC19 in the orientation that placed the 3' end of UbB adjacent to the SmaI site of the polylinker in pUC19, yielding pUbB. A 1.04 kb DraI/SmaI fragment of pUbB containing the UbB coding and 3' flanking regions (the DraI site is located 10 bp upstream of the UbB start codon) was subcloned into the SmaI/HincII-digested pUC19, placing the UbB start codon adjacent to the EcoRI site in the polylinker, and yielding pHUb3. This plasmid was partially digested with SalI, which cleaves once within each Ub-coding repeat (the polylinker's SalI site was removed during the construction of pHUb3); the vector-containing fragment that retained two Ub-coding repeats was isolated and self-ligated, yielding pHUb2. The inserts of pHUb2 and pHUb3 were excised with EcoRI and PstI, and subcloned into the EcoRI/Psa-cut pKK223-3, yielding, respectively, pKKHUb2 and pKKHUb3. The start codon of the Ub-coding region in these plasmids is 36 bp downstream of the Shine-Dalgarno sequence in pKK223-3.

Screening Results

*E. coli* carrying a plasmid expressing Ub-Arg-βgal were transformed with the *S. cerevisiae* genomic DNA library RB237 carried in the plasmid YCp50, plated on X-Gal plates containing antibiotics that selected for the presence of both plasmids, and incubated overnight at 37° C. Of ~800 colonies thus screened, six (named pRBW1–pRBW6) were white or pale blue, whereas the other colonies were dark blue (comparable to control colonies of *E. coli* transformed with the YCp50 vector alone). Three of the six candidate colonies were found to be false positives, two contained plasmids (termed pRBW1 and pRBW6) with overlapping inserts of yeast DNA, while the remaining colony contained a plasmid (termed pRBW2) with a distinct yeast DNA insert. Plasmids pRBW1 and pRBW2 were isolated and retransformed into *E. coli* expressing either Ub-Arg-βgal or Ub-Met-βgal. Transformants expressing Ub-Arg-βgal formed white colonies on X-Gal plates, confirming the original results, whereas transformants expressing Ub-Met-βgal formed blue colonies on these plates, indicating that the metabolic destabilization of Ub-Arg-βgal by inserts in pRBW1 and pRBW2 was N-end rule-specific. (Arg and Met are, respectively, destabilizing and stabilizing residues in the *E. coli* N-end rule).

Surprisingly, extracts of *E. coli* carrying pRBW1 or pRBW2 were inactive in an in vitro deubiquitinating assay with Ub-Met-DHFR, suggesting that Ub-specific proteases encoded by pRBW1 and pRBW2 were either inactivated in cell extracts or, alternatively, could deubiquitinate ubiquitin fusions cotranslationally but not posttranslationally. The Ub-specific protease activities conferred by pRBW1 and pRBW2 on *E. coli* were therefore assayed in vivo by pulse-chase analyses with Ub-Met-βgal, using a monoclonal antibody to βgal. The results confirmed that pRBW1 and pRBW2 (but not the YCp50 vector alone) did confer deubiquitinating activity on *E. coli*. Subsequent overexpression of Ub-specific proteases encoded by pRBW1 and pRBW2 made possible their detection in *E. coli* extracts as well.

Figure 3:
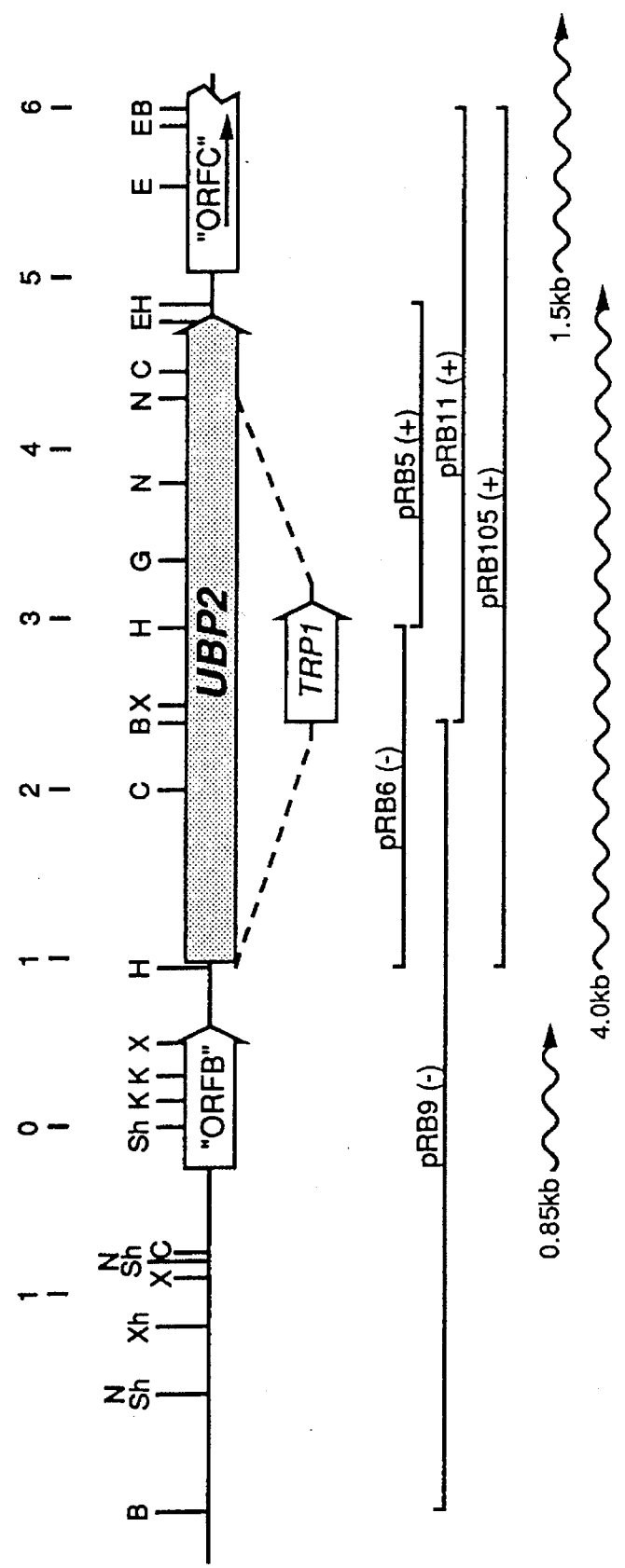
FIG. 3 is a diagram representing a restriction map of UBP2.

The ORF encoding deubiquitinating activity of pRBW2 was identified by subcloning experiments and nucleotide sequencing, and was named the UBP2 gene (FIG. 3 and Sequence I.D. Number 5). The position of the start (ATG) codon in the UBP2 was inferred so as to yield the longest (3715 bp) ORF encoding an acidic (calculated pI of 4.95), 1264-residue (145 kDa) protein.

Figure 4:
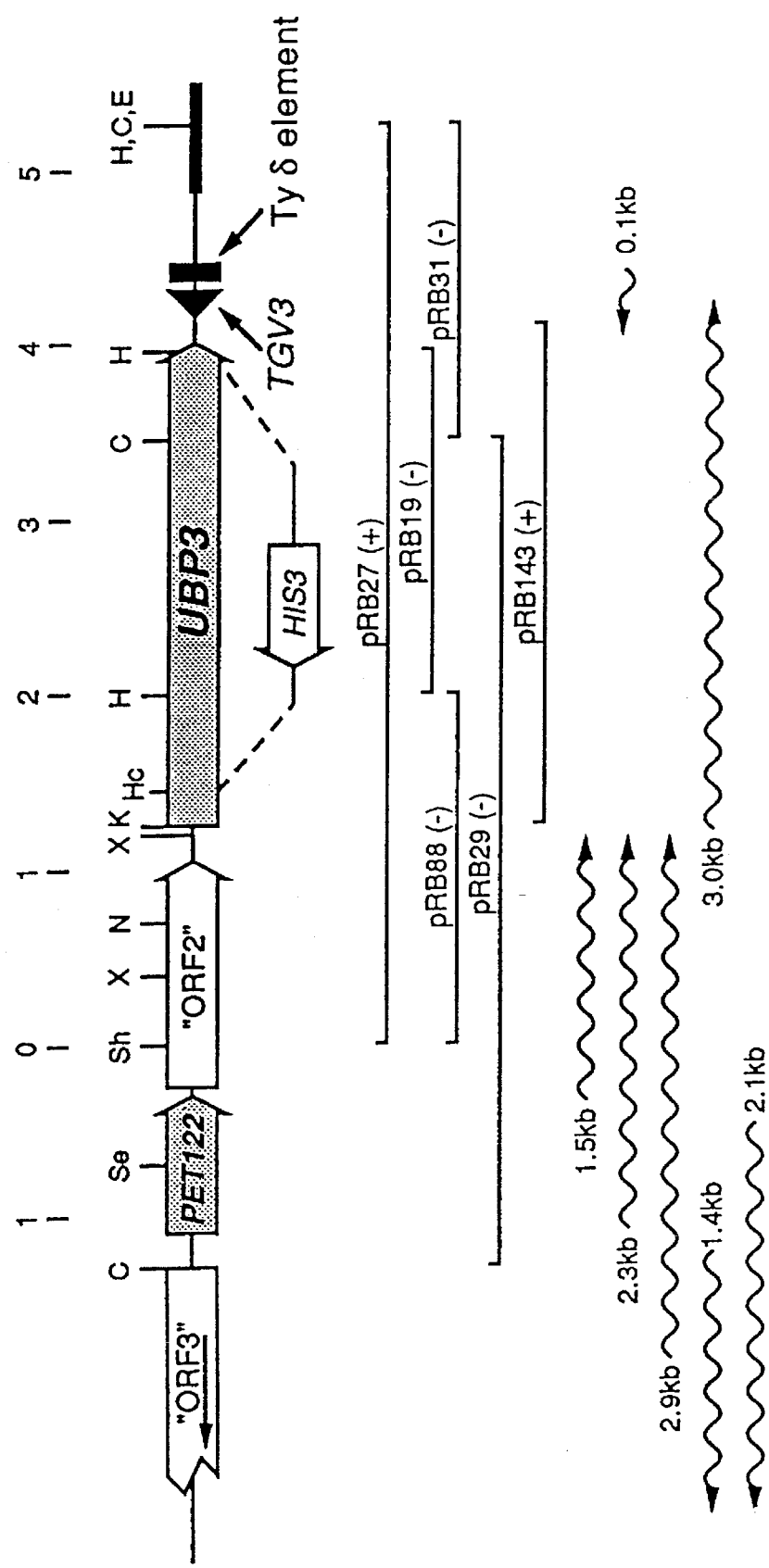
FIG. 4 is a diagram representing a restriction map of UBP3.

The ORF encoding deubiquitinating protease of pRBW1 was identified by subcloning experiments and nucleotide sequencing, and was named the UBP3 gene (FIG. 4 and Sequence I.D. Number 7). The position of the start (ATG) codon was inferred so as to yield the longest (2736 bp) ORF, which encodes a slightly basic (calculated pI of 7.92), 912-residue (102 kDa) protein. A plasmid (pRB143) containing this ORF downstream of an *E. coli* promoter conferred deubiquitinating activity on *E. coli*.

Expression of UBP1, UBP2 and UBP3 in *E. coli*

The previously constructed plasmids pJT70 (pUC19-based) and pJT184 (pACYC184-based) expressed the yeast UBP1 in *E. coli* from the yeast UBP1 promoter, which is weakly active in *E. coli*. Although a 1.9 kb HindIII subclone of pRBW2 conferred deubiquitinating activity on *E. coli*, it contained only the 3' half of the UBP2ORF. Pilot experiments indicated that the truncated Ubp2 protein yielded variable levels of deubiquitinating activity in *E. coli* extracts. To construct a plasmid that expressed the full-length Ubp2 in *E. coli*, a 5' portion of UBP2, isolated as the 1.56 kb HindIII/XbaI fragment of pRB6 (see FIG. 3), was subcloned into pRS316 (Sikorski and Hieter, *Genetics* 122: 19–27 (1989)), which contains a polylinker, placing an EcoRI site close to the HindIII site in UBP2. The resulting insert was then excised as the 1.57 kb EcoRI/XbaI fragment. A 3' portion of UBP2 was isolated as the ~3.4 kb XbaI/BamHI fragment from pRB11 (see FIG. 3), and subcloned into pRS316, placing a PstI site close to the BamHI site in UBP2. The resulting insert was then excised as a ~3.4 kb XbaI/PstI fragment. This fragment and the above 1.57 kb EcoRI/XbaI fragment were ligated into the EcoRI/XbaI-cut pKK223-3, yielding (among other products) the plasmid pRB 105, which contained UBP2 in the correct orientation, 50 bp downstream from the Shine-Dalgarno sequence of pKK223-3. For experiments requiring the simultaneous presence of two distinct plasmids in *E. coli*, the UBP2/rrnB terminator region of pRB105 was excised as the ~6.4 kb SphI/ScaI fragment, and subcloned into the SphI/EcoRV-cut pACYC 184, yielding pRB173.

Since in the initial experiments, the Ub-specific protease activity of Ubp3 could be detected in vivo but not in *E. coli* extracts, a UBP3-overexpressing plasmid was constructed. The ~2.9 kb KpnI/DraI fragment of pRB27 that contained the entire UBP3 gene was subcloned into the KpnI/HincII-cut pUC19, placing the EcoRI and the Psa site of the plasmid near, respectively, the KpnI site and the DraI site of the introduced insert. The insert was then excised with EcoRI/PstI and subcloned into the EcoRI/PstI-cut pKK223-3, yielding pRB143, which contained UBP3 in the correct orientation, 50 bp downstream form the Shine-Dalgarno sequence of pKK223-3. For experiments requiring the simultaneous presence of two distinct plasmids in *E. coli*, the UBP3/rrnB terminator region of pRB 143 was excised as the ~4.2 kb SphI/ScaI fragment and subcloned into the SphI/EcoRV-cut pACYC184, yielding pRB175.

In more recent experiments, UBP1, UBP2 and UBP3 were overexpressed in *E. coli* from a pKK-based expression vector (Ausubel et al., *Current Protocols in Molecular Biology*, J. Wiley & Sons, N.Y. (1989)). Each of the UBP proteins was expressed to a level where it comprises a substantial proportion (1–5%) of the total cellular protein.

Sequence Comparisons of Ub-specific Proteases

Sequence alignment of the 809-residue Ubp1, 1264-residue Ubp2 and 912-residue Ubp3 demonstrated the lack of overall sequence similarity between these proteins, as well as the presence of two short regions of statistically significant similarity that are spaced a few hundred residues apart in each of the Ubp proteases. The two regions of similarity are centered around a Cys and two His residues. As has been seen with Ubp1, neither Ubp2 nor Ubp3 have significant sequence similarities to the fourth Ub-specific protease of yeast, Yuh1 or its mammalian homologs. The region in Yuh1 and its mammalian homologs that contains a putative active-site Cys residue is not similar to the conserved "Cys" region of Ubp1–Ubp3: apart from the Cys residue, only one other residue position is occupied by an identical residue (Ash) in all six proteins. No such identities are seen in an analogous alignment of the two conserved His residues in Yuh1-like proteases with either of the conserved His residues in Ubp1–Ubp3.

In Vitro Properties of Ub-specific Proteases

The previously characterized Ubp1 protease can efficiently deubiquitinate in vitro a variety of linear ubiquitin fusion proteins, including the natural ubiquitin precursors Ubi1–Ubi3 and engineered fusions such as Ub-X-βgal and Ub-X-DHFR. Similar assays, in which an extract of *E. coli* carrying an overexpression vector-based plasmid expressing either Ubp2 (pRB105), Ubp3 (pRB143), or Yuh1 (pKKYUH1) is incubated with Ub-containing test proteins, were used to analyze in vitro the substrate specificity of these proteases. Extracts of *E. coli* carrying the UBP1-expressing plasmid pJT70 or vector alone, were also used in these assays. The cleavage products were fractionated by SDS-PAGE and visualized by immunoblotting, using anti-Ub antibodies or, with purified, $^{35}$S-labeled test proteins, directly by fluorography.

In these in vitro assays, the Ubp2 protease efficiently deubiquitinated Ub-Met-βgal and Ub-Met-DHFR, as well as Ubi2 and Ubi3, the natural precursors of ubiquitin, in which it is fused to specific ribosomal proteins. Both Ubp1 and Ubp2 released the Cys residue from Ub-Ub-Cys (diubiquitin bearing a one-residue C-terminal extension) but were unable to cleave at the Ub-Ub junction in Ub-Ub-Cys. Ubp1 and Ubp2 were also unable to cleave at the Ub-Ub junctions in the yeast polyubiquitin, a natural ubiquitin precursor containing five head-to-tail ubiquitin repeats as was previously reported for Ubp 1. Thus, Ubp1 and Ubp2 efficiently cleaved in vitro after the last (Gly$^{76}$) residue of ubiquitin in all of the tested ubiquitin fusions, the Ub-Ub linkage in polyubiquitins being the single exception. However, as shown below, these proteases are able to cleave polyubiquitin when coexpressed with it *E. coli*.

Although the expression of Ubp3 in *E. coli* from the pKK overexpression vector-based plasmid pRB143 resulted in a substantial overproduction of a protein with the expected molecular mass, extracts of Ubp3-expressing *E. coli* lacked deubiquitinating activity. Since Ubp3 is certainly active in *E. coli* in vivo, it is either inactivated in cell extracts or is able to cleave ubiquitin fusions exclusively during or shortly after their ribosome-mediated synthesis.

In agreement with previously reported findings, extracts of *E. coli* expressing Yuh1 efficiently deubiquitinated short ubiquitin fusions such as Ubi2 and Ubi3. However, Yuh1 was much less active against the larger fusion tro-Met-DHFR (a 229-residue C-terminal extension of ubiquitin), deubiquitinating at most ~50% of the fusion even after a prolonged incubation, and was virtually inactive against Ub-Met-βgal (Sequence I.D. Numbers 1–2).

In Vivo Properatis of Ub-specific Proteases

As expected from their activities in *E. coli* extracts, both Ubp1, Ubp2 and Yuh1 were active in vivo against the natural. ubiquitin fusions Ubi2 and Ubi3. Ubp3, which was inactive in *E. coli* extracts, efficiently deubiquitinated Ubi2 and Ubi3 when coexpressed with them in *E. coli*. While Ubp 1 and Ubp2 were unable to cleave at the Ub-Ub junction in polyubiquitins in vitro, both of them were active against yeast polyubiquitin when coexpressed with it in *E. coli*. In contrast, the Ubp3 protease, while active in vivo against ubiquitin fusions such as Ubi2 and Ubi3, was inactive, under the same conditions, against polyubiquitin. These distinctions among Ub-specific processing proteases indicate subtle differences in their requirements for the conformation of protein domains in the vicinities of Ub-X peptide bonds.

The in vivo deubiquitination of ubiquitin fusions such as Ub-Met-βgal by Ubp2 and Ubp3 was also followed by pulse-chase analysis, in part to confirm the findings of the original X-Gal screen. As expected, both proteases deubiquitinated Ub-Met-βgal in vivo, except that the cleavage by Ubp3 was incomplete, and a significant proportion of pulse-labeled Ub-Met-βgal remained intact 15 min after the pulse. These results are consistent with the pattern of deubiquitination by Ubp3 that is more strictly cotranslational than that by Ubp2. In a similar pulse-chase assay, Yuh1 was unable to deubiquitinate Ub-Met-βgal in vivo, indicating that an apparently greater susceptibility of the Ub-Met peptide bond in a nascent (as distinguished from mature) Ub-Met-βgal is insufficient to allow its deubiquitination by Yuh1. By contrast, this difference is sufficient to allow a cotranslational (but apparently not posttranslational) deubiquitination of Ub-Met-βgal by Ubp3.

EQUIVALENTS

Those skilled in the art will recognize or be able to ascertain, using no more than routine experimentation, many equivalents to the specific embodiments of the invention described herein. Such equivalents are intended to be encompassed by the claims which follow the Sequence Listing.

---

We claim:

1. An isolated ubiquitin-specific protease which specifically cleaves a ubiquitin fusion protein having a molecular weight of about 120 kilodaltons, the specific cleavage taking place in vitro between the C-terminal residue of ubiquitin and the N-terminal residue of the protein or peptide, the fusion protein being encoded by the DNA represented in Sequence ID Number 1.

2. An isolated protease of claim 1 which is encoded by the DNA represented in Sequence I.D. Number 5.

3. An isolated ubiquitin-specific protease which specifically cleaves a ubiquitin fusion protein having a molecular weight of about 120 kilodaltons, the specific cleavage taking place in a prokaryotic cell between the C-terminal residue of ubiquitin and the N-terminal residue of the protein or peptide, the fusion protein being encoded by the DNA represented in Sequence I.D. Number 1.

4. An isolated protease of claim 3 which is encoded by the DNA represented in Sequence I.D. Number 5.

5. An isolated protease of claim 3 which is encoded by the DNA represented in Sequence I.D. Number 7.

* * * * *